(12) United States Patent
Miele et al.

(10) Patent No.: US 8,328,727 B2
(45) Date of Patent: Dec. 11, 2012

(54) METHOD AND APPARATUS FOR ASSESSING HEMODYNAMIC PARAMETERS WITHIN THE CIRCULATORY SYSTEM OF A LIVING SUBJECT

(75) Inventors: Frank R. Miele, San Diego, CA (US); Ronald Mucci, Westwood, MA (US); Stuart L. Gallant, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 1928 days.

(21) Appl. No.: 11/437,197

(22) Filed: May 18, 2006

(65) Prior Publication Data

US 2006/0206032 A1 Sep. 14, 2006

Related U.S. Application Data

(62) Division of application No. 09/815,080, filed on Mar. 22, 2001, now Pat. No. 7,048,691.

(51) Int. Cl.
*A61B 5/02* (2006.01)
*A61B 8/00* (2006.01)

(52) U.S. Cl. ......... 600/481; 600/483; 600/437; 600/449

(58) Field of Classification Search .................. 600/481, 600/483, 437, 449
See application file for complete search history.

(56) References Cited

U.S. PATENT DOCUMENTS

| | | | |
|---|---|---|---|
| 3,527,197 A | 9/1970 | Ware et al. | |
| 3,601,120 A | 8/1971 | Massie et al. | |
| 3,617,993 A | 11/1971 | Massie et al. | |
| 3,663,932 A | 5/1972 | Mount et al. | |
| 3,791,378 A | 2/1974 | Hochberg et al. | |
| 3,885,551 A | 5/1975 | Massie | |
| 4,109,647 A | 8/1978 | Stern et al. | |
| 4,127,114 A | 11/1978 | Bretscher | |
| 4,154,231 A | 5/1979 | Russell | |
| 4,239,047 A | 12/1980 | Griggs, III et al. | |
| 4,249,540 A | 2/1981 | Koyama et al. | |
| 4,349,034 A | 9/1982 | Ramsey, III | |

(Continued)

FOREIGN PATENT DOCUMENTS

DE 4218319 6/1992

(Continued)

OTHER PUBLICATIONS

Drzewiecki, G. (1995) "Noninvasive Assessment of Arterial Blood Pressure and Mechanics," The Biomedical Engineering Handbook CRC Press, Boca Raton, FL, pp. 1196-1211.

(Continued)

*Primary Examiner* — Navin Natnithithadha
(74) *Attorney, Agent, or Firm* — Gazdzinski & Associates, PC

(57) ABSTRACT

An improved method and apparatus for non-invasively assessing one or more hemodynamic parameters associated with the circulatory system of a living organism. In one aspect, the invention comprises a method of measuring a hemodynamic parameter by measuring a non-calibrated value of the parameter non-invasively, and inducing a stress of the circulatory system while measuring a second parameter. The response of the circulatory system to the stress is determined directly from the subject, and a calibration function is derived from the response and applied to the non-calibrated measured value to produce a calibrated measure of the actual value of the hemodynamic parameter. Methods of using backscattered acoustic energy for determination of hemodynamic markers are also disclosed.

19 Claims, 53 Drawing Sheets

U.S. PATENT DOCUMENTS

| | | | |
|---|---|---|---|
| 4,476,875 A | | 10/1984 | Nilsson et al. |
| 4,566,462 A | | 1/1986 | Janssen |
| 4,590,948 A | | 5/1986 | Nilsson |
| 4,596,254 A | | 6/1986 | Adrian et al. |
| 4,630,612 A | * | 12/1986 | Uchida et al. ............ 600/441 |
| 4,651,747 A | | 3/1987 | Link |
| 4,660,564 A | * | 4/1987 | Benthin et al. ............ 600/449 |
| 4,719,923 A | | 1/1988 | Hartwell et al. |
| 4,721,113 A | * | 1/1988 | Stewart et al. ............ 600/449 |
| 4,754,761 A | | 7/1988 | Ramsey, III et al. |
| 4,771,792 A | | 9/1988 | Seale |
| 4,867,170 A | | 9/1989 | Takahashi |
| 4,869,261 A | | 9/1989 | Penaz |
| 4,901,733 A | | 2/1990 | Kaida et al. |
| 4,924,871 A | | 5/1990 | Honeyager |
| 4,960,128 A | | 10/1990 | Gordon et al. |
| 5,030,956 A | | 7/1991 | Murphy |
| 5,094,244 A | | 3/1992 | Callahan et al. |
| 5,119,822 A | | 6/1992 | Niwa |
| 5,152,297 A | | 10/1992 | Meister et al. |
| 5,158,091 A | | 10/1992 | Butterfield et al. |
| 5,163,438 A | | 11/1992 | Gordon et al. |
| 5,170,796 A | | 12/1992 | Kobayashi |
| 5,238,000 A | | 8/1993 | Niwa |
| 5,240,007 A | | 8/1993 | Pytel et al. |
| 5,243,987 A | * | 9/1993 | Shiba ............ 600/463 |
| 5,261,412 A | | 11/1993 | Butterfield et al. |
| 5,273,046 A | | 12/1993 | Butterfield et al. |
| 5,280,787 A | * | 1/1994 | Wilson et al. ............ 600/456 |
| 5,327,893 A | | 7/1994 | Savic |
| 5,363,850 A | * | 11/1994 | Soni et al. ............ 600/454 |
| 5,368,039 A | | 11/1994 | Moses |
| 5,379,770 A | * | 1/1995 | Van Veen ............ 600/455 |
| 5,409,010 A | | 4/1995 | Beach et al. |
| 5,439,001 A | | 8/1995 | Butterfield et al. |
| 5,450,852 A | | 9/1995 | Archibald et al. |
| 5,467,771 A | | 11/1995 | Narimatsu et al. |
| 5,479,928 A | | 1/1996 | Cathignol et al. |
| 5,494,043 A | | 2/1996 | O'Sullivan et al. |
| 5,495,852 A | | 3/1996 | Stadler et al. |
| 5,551,434 A | | 9/1996 | Iinuma |
| 5,590,649 A | | 1/1997 | Caro et al. |
| 5,617,867 A | | 4/1997 | Butterfield et al. |
| 5,634,467 A | | 6/1997 | Nevo |
| 5,642,733 A | | 7/1997 | Archibald et al. |
| 5,649,542 A | | 7/1997 | Archibald et al. |
| 5,649,543 A | | 7/1997 | Hosaka et al. |
| 5,701,898 A | * | 12/1997 | Adam et al. ............ 600/454 |
| 5,749,364 A | | 5/1998 | Sliwa et al. |
| 5,785,654 A | | 7/1998 | Iinuma et al. |
| 5,832,924 A | | 11/1998 | Archibald et al. |
| 5,833,618 A | | 11/1998 | Caro et al. |
| 5,848,970 A | | 12/1998 | Voss et al. |
| 5,855,557 A | | 1/1999 | Lazenby |
| 5,876,343 A | | 3/1999 | Teo |
| 5,876,346 A | | 3/1999 | Corso |
| 5,882,311 A | | 3/1999 | O'Rourke |
| 5,895,359 A | | 4/1999 | Peel, III |
| 5,904,654 A | | 5/1999 | Wohltmann et al. |
| 5,908,027 A | | 6/1999 | Butterfield et al. |
| 5,964,710 A | * | 10/1999 | Ganguly et al. ............ 600/449 |
| 5,964,711 A | | 10/1999 | Voss et al. |
| 6,010,457 A | | 1/2000 | O'Rourke |
| 6,027,452 A | | 2/2000 | Flaherty et al. |
| 6,056,692 A | * | 5/2000 | Schwartz ............ 600/443 |
| 6,176,831 B1 | | 1/2001 | Voss et al. |
| 6,200,268 B1 | * | 3/2001 | Vince et al. ............ 600/443 |
| 6,213,949 B1 | * | 4/2001 | Ganguly et al. ............ 600/449 |
| 6,228,034 B1 | * | 5/2001 | Voss et al. ............ 600/485 |
| 6,258,031 B1 | | 7/2001 | Sunagawa et al. |
| 6,267,728 B1 | | 7/2001 | Hayden |
| 6,554,774 B1 | * | 4/2003 | Miele ............ 600/485 |
| 6,565,512 B1 | * | 5/2003 | Ganguly et al. ............ 600/449 |
| 6,612,989 B1 | * | 9/2003 | Brock-Fisher ............ 600/447 |
| 6,723,051 B2 | * | 4/2004 | Davidson et al. ............ 600/454 |
| 6,740,038 B2 | * | 5/2004 | Davidson et al. ............ 600/438 |
| 6,802,813 B2 | * | 10/2004 | Schutt ............ 600/454 |
| 6,846,288 B2 | * | 1/2005 | Nagar et al. ............ 600/437 |
| 6,875,176 B2 | * | 4/2005 | Mourad et al. ............ 600/442 |
| 7,048,691 B2 | * | 5/2006 | Miele et al. ............ 600/504 |
| 7,238,158 B2 | * | 7/2007 | Abend ............ 600/454 |
| 7,399,279 B2 | * | 7/2008 | Abend et al. ............ 600/450 |
| 7,503,896 B2 | * | 3/2009 | Miele et al. ............ 600/454 |
| 7,534,209 B2 | * | 5/2009 | Abend et al. ............ 600/454 |
| 2002/0055680 A1 | | 5/2002 | Miele |

FOREIGN PATENT DOCUMENTS

| | | |
|---|---|---|
| EP | 284 096 | 3/1988 |
| EP | 0 342 249 | 5/1988 |
| EP | 0299 827 | 6/1988 |
| EP | 0595 668 | 9/1993 |
| EP | 0 603 666 | 12/1993 |
| EP | 0818 176 | 7/1996 |
| WO | WO 84 00290 | 2/1984 |
| WO | WO 92 07508 | 5/1992 |
| WO | WO 95/00074 | 1/1995 |
| WO | WO 95 13014 | 5/1995 |
| WO | WO 98 25511 | 6/1998 |

OTHER PUBLICATIONS

Drzewiecki, G.M., et al. (1985) Generalization of the Transmural Pressure-Area Relation for the Femoral Artery, 7.sup.th Annual IEEE EMBS Conference 507.

Hoeks, A.P.G., et al. (1985) Transcutaneous Detection of Relative Changes in Artery Diameter, Ultrasound in Med and Bio 11:51-59.

Carson, E.R., et al. (1983) "The Mathematical Modeling of Metabolic and Endocrine Systems: Model Formulation, Identification, and Validat on," John Wiley & Sons. NY. pp. 185-189.

Anderson, E.A., et al. (1989) "Flow-Mediated and Reflex Changes in Large Peripheral Artery Tone in Humans," Circulation 79:93-100.

Hartley, C.J., et al. (1991) "An Ultrasonic Method for Measuring Tissue Displacement: Technical Details and Validation for Measuring Myocardial Thickening," IEEE Trans Blomed. 38:735-747.

Cariou, Alain, et al. (1998) "Noninvasive Cardiac Output Monitoring by Aortic Blood Flow Determination: Evaluation of the Sometec Cynemo 3000 System," Critical Care Medicine, vol. 26, No. 12, pp. 2066-2072.

* cited by examiner

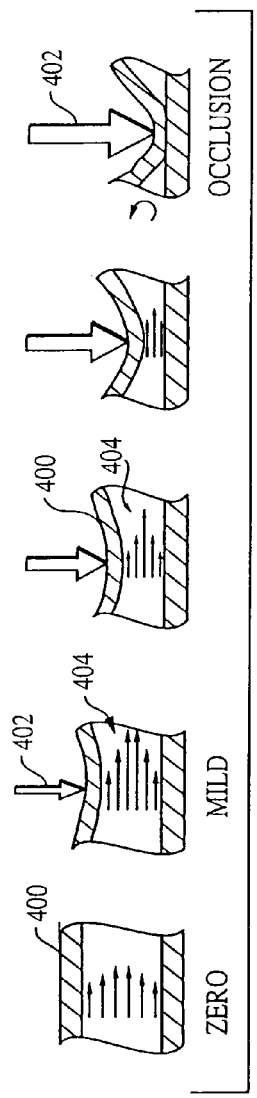
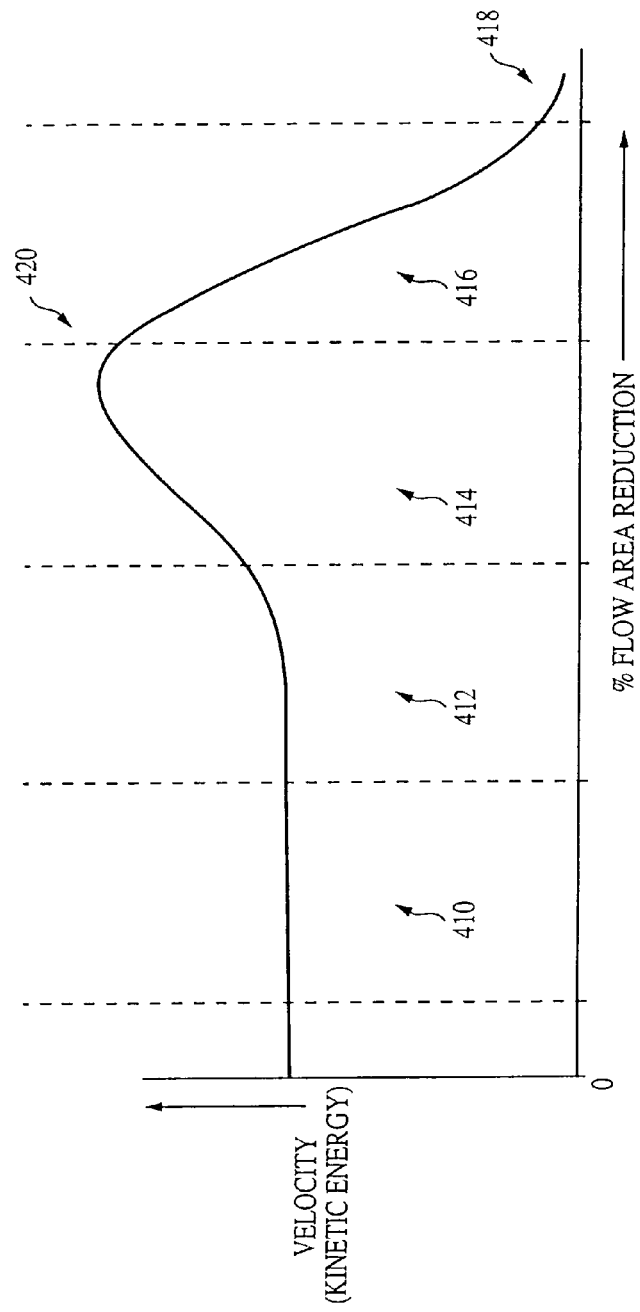
FIG. 4a
FIG. 4b

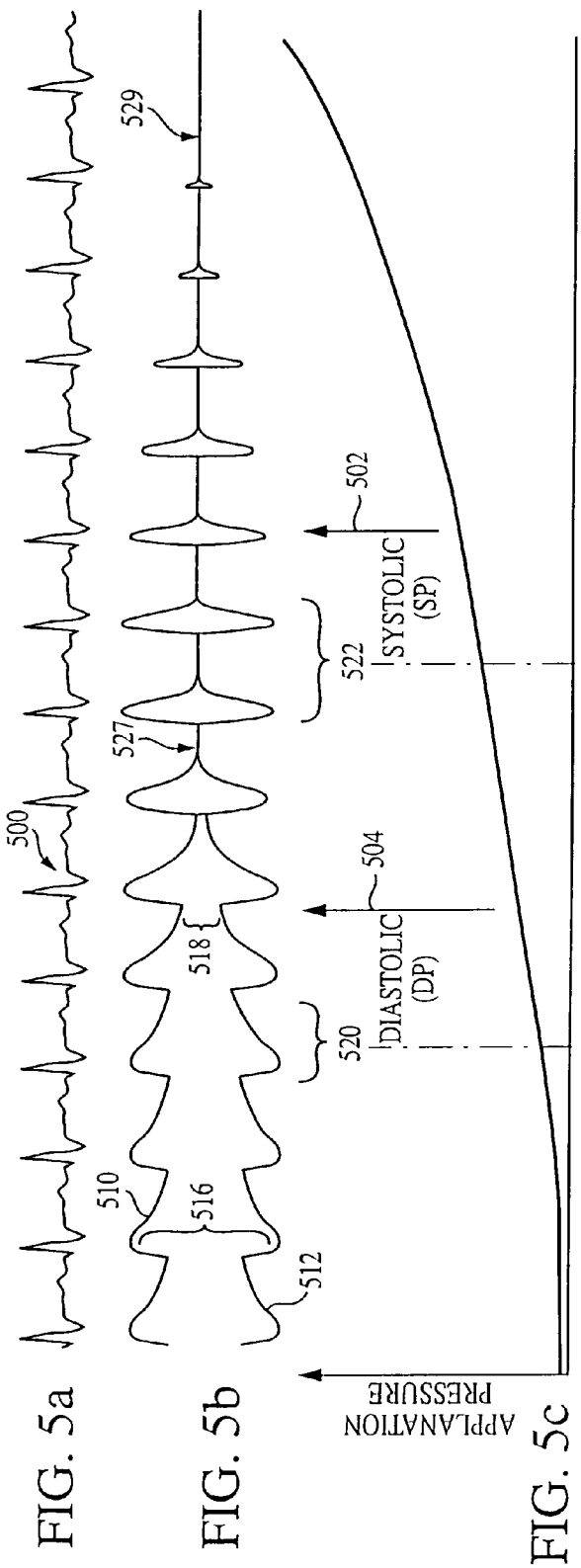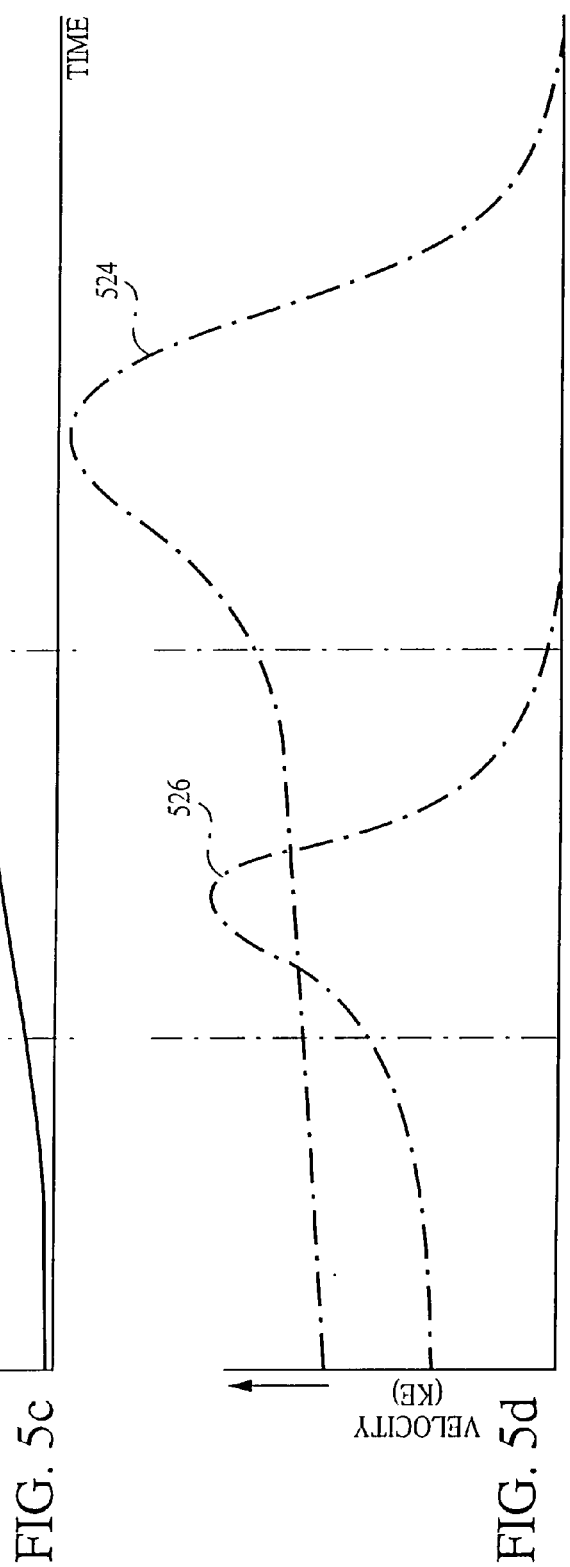
FIG. 5a  FIG. 5b  FIG. 5c  FIG. 5d

| |
|---|
| -1 |
| -1 |
| 0 |
| 2 |
| 4 |
| 6 |
| 6 |
| 2 |
| -6 |
| -16 |
| -25 |
| -26 |
| -16 |
| 10 |
| 50 |
| 98 |
| 143 |
| 176 |
| 188 |
| 176 |
| 143 |
| 98 |
| 50 |
| 10 |
| -16 |
| -26 |
| -25 |
| -16 |
| -6 |
| 6 |
| 6 |
| 6 |
| 4 |
| 2 |
| 0 |
| -1 |
| -1 |

FIG. 23

METHOD AND APPARATUS FOR ASSESSING HEMODYNAMIC PARAMETERS WITHIN THE CIRCULATORY SYSTEM OF A LIVING SUBJECT

This application is a divisional of and claims priority to U.S. patent application Ser. No. 09/815,080 of the same title, filed Mar. 22, 2001, now U.S. Pat. No. 7,048,691 issued May 23, 2006 and incorporated herein by reference in its entirety. This application is related to U.S. patent application Ser. No. 09/534,900 entitled "Method And Apparatus For Assessing Hemodynamic Properties within the Circulatory System of a Living Subject" filed Mar. 23, 2000, now U.S. Pat. No. 6,554,774 issued Apr. 29, 2003, also incorporated by reference herein in its entirety.

RELATED APPLICATIONS

This application is related to U.S. patent application Ser. No. 09/815,982 entitled "Method And Apparatus For The Noninvasive Assessment Of Hemodynamic Parameters Including Blood Vessel Location" filed contemporaneously herewith, assigned to the Assignee hereof.

BACKGROUND OF THE INVENTION

1. Field of the Invention

This invention relates generally to methods and apparatus for monitoring parameters associated with the circulatory system of a living subject, and specifically to the non-invasive monitoring of arterial blood pressure.

2. Description of Related Technology

Arterial Blood Pressure Measurement

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. This theory is illustrated graphically in FIG. 1. Note that in FIG. 1, bone or another rigid member is assumed to lie under the artery.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement.

Tonometry systems are also commonly quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches to lateral sensor positioning similarly suffer from not being able to maintain a constant angular relationship with the artery regardless of lateral position, due in many cases to positioning mechanisms which are not adapted to account for the anatomic features of the subject, such as curvature of the wrist surface.

Another significant drawback to arterial tonometry systems in general is their inability to continuously monitor and adjust the level of arterial wall compression to an optimum level of zero transmural pressure. Generally, optimization of arterial wall compression has been achieved only by periodic recalibration. This has required an interruption of the subject monitoring function, which sometimes can occur during critical periods. This disability severely limits acceptance of tonometers in the clinical environment.

A further limitation of the tonometry approach relates to incomplete pressure pulse transfer from the interior of the blood vessel to the point of measurement on the surface of the skin above the blood vessel. Specifically, even when the optimum level of arterial compression is achieved, there is incomplete and complex coupling of the arterial blood pressure through the vessel wall and through the tissue, to the surface of the skin, such that the magnitude of pressure variations occurring within the blood vessel is different than that measured by a tonometric sensor (pressure transducer) placed on the skin. Hence, any pressure signal or waveform measured at the skin necessarily differs from the true pressure within the artery. Modeling the physical response of the arterial wall, tissue, musculature, tendons, bone, skin of the wrist is no small feat, and inherently includes uncertainties and anomalies for each separate individual. These uncertainties and anomalies introduce unpredictable error into any measurement of blood pressure made via a tonometric sensor.

One prior art method of calibrating tonometric pressure measurements utilizes an oscillometric device (i.e., a pressure cuff or similar) to periodically obtain "actual" pressure information which is then used to calibrate the tonometric measurements. This approach suffers from the need to perform ongoing calibration events, specifically inflations/deflations of the cuff, in order to maintain device calibration. Such calibration events are distracting, uncomfortable, and can practically only be performed with a comparatively long periodicity. Furthermore, this technique does not calibrate based on measurement of actual hemodynamic changes occurring within the circulatory system, but rather based on external measurements which may or may not be representative of the actual changes. No mechanism for correcting for incomplete pulse transfer from the blood vessel to the sensor(s) due to interposed tissue, etc. is provided either.

Other prior art calibration techniques have attempted to transmit or induce a perturbation within the blood flowing in the blood vessel, and subsequently sense the component of that signal within the measured hemodynamic parameter (e.g., blood pressure waveform) to generate an offset or correction for the measured parameter. See, for example, U.S. Pat. No. 5,590,649 entitled "Apparatus and Method for Measuring an Induced Perturbation to Determine Blood Pressure" assigned to Vital Insite, Inc. ('649 patent). Under the approach of the '649 patent, changes in a variety of hemodynamic parameters resulting ostensibly from changes in blood pressure are modeled and stored within the device, and compared to data obtained from a tonometric sensor This approach, however, has a profound disability in that the calibration offset is determined not by direct measurement of the hemodynamic parameters of the subject under evaluation, but by modeling the relationship between blood pressure and perturbation wave velocity; i.e., velocity and phase are modeled to have a certain relationship to changes in blood pressure; therefore, in theory, observed changes in velocity/phase of the perturbation wave can be used to generate estimations of actual blood pressure within the subject being evaluated. The limits of this system are clearly dictated by the ability to accurately model many complex, non-linear, interdependent parameters, as well as predict the time variance of these many parameters.

Hemodynamics and Diseases of the Circulatory System

The science of hemodynamics, or the analysis of fluid (blood) flow within the body, is presently used effectively to detect and/or diagnose diseases of or defects within the circulatory system. For example, valvular disease, cardiac structural defects, venous disease, reduced cardiac function, and arterial disease may be assessed by studying how the blood flows through various portions of the circulatory system. Of particular interest is the analysis of arterial diseases such as stenosis (i.e. blockage or reduction in effective cross-sectional area due to arterial plaque, etc.). It is known that as the degree of stenosis within the blood vessel of a living subject varies, certain changes in the parameters of the circulatory system and in the overall health of the subject occur. As illustrated in FIG. 2, varying degrees of stenosis within a hypothetical blood vessel will occlude that blood vessel to a generally proportional degree; i.e., no stenosis results in no occlusion and no attendant symptoms, while complete stenosis results in complete occlusion, with no flow of blood through the vessel and very dire symptoms in the subject. At levels of stenosis falling somewhere there between, the response can be somewhat more complex. For example, the subject may suffer stenosis which very significantly reduces the effective cross-sectional area of a given blood vessel, yet manifests itself in very few if any symptoms under normal levels of exercise. However, the same subject can exhibit dramatic symptoms with an increase in exercise as the patient exerts more effort, the tissue under exertion has a higher metabolic demand requiring an increase in perfusion. Normally, vasodilation and collateralized blood flow provide the compensatory mechanism to increase the volumetric flow to meet the higher volumetric demand. However, since the vessel is significantly stenosed, the compensatory mechanism has already been utilized to meet the normal, non-exercise demand. As a result, the body is unable to increase the volumetric demand since it has no way of minimizing the energy loss associated with overcoming the resistance of the stenosed (decreased) area of the vessel. If volumetric flow does not increase, the increased metabolic demand is not met and the distal tissue becomes ischemic.

By modeling the stenotic artery as a fluid system having an internal pressure (P) and blood mass flow rate (Q) or blood velocity (v), a modified version of the well known Bernoulli equation may be applied to describe the flow of blood within the artery as follows:

$$\Delta P \propto 4 \cdot v^2 \qquad \text{Eqn. (1)}$$

Hence, the foregoing relationship may be used to assess one hemodynamic parameter when another is known. For example, the pressure gradient ($\Delta P$) across a stenosis within the artery may be estimated by obtaining data on the velocity of blood flowing through the stenosis, and then using this velocity data within Eqn. (1). The velocity data may be obtained by any number of well-known techniques, such as spectral Doppler ultrasound.

However, despite their utility in assessing the severity of stenoses present in the artery and other such diseases, prior art hemodynamic evaluation techniques are effectively incapable of assessing the absolute blood pressure within the artery at any given time. In theory, an accurate model of the response of the circulatory system could be used to estimate the value of parameters within the system (such as true arterial pressure) based on known or measured values of other parameters. As can be appreciated, however, the circulatory system of a living organism, and especially a human being, is extremely complex, with literally thousands of interconnected blood vessels. This system includes, inter alia, scores of capillaries, veins, and arteries, each having their own unique physical properties. Furthermore, within each of the aforementioned categories of blood vessel, individual constituents may have markedly different properties and response within the circulatory system. For example, two arteries within the human body may (i) have different diameters at different points along their length; (ii) supply more or less veins and capillaries than the other; (iii) have more or less elasticity; and (iv) have more or less stenosis associated therewith.

The properties and response of each of the blood vessels also may be affected differently by various internal and/or external stimuli, such as the introduction of an anesthetic into the body. Even common autonomic responses within the body such as respiration affect the pressure in the circulatory system, and therefore may need to be considered.

Considering these limitations, it becomes exceedingly difficult if not impossible to accurately model the circulatory system of the human being in terms of its fluid dynamic properties for use in blood pressure estimation. Even if a hypothetical circulatory system could be accurately modeled, the application of such a model would be susceptible to significant variability from subject to subject due to each subject's particular physical properties and responses. Hence, such approaches can at best only hope to form gross approximations of the behavior of the circulatory system, and accordingly have heretofore proven ineffective at accurately determining the blood pressure within a living subject.

Based on the foregoing, what is needed is an improved method and apparatus for assessing hemodynamic parameters, including blood pressure, within a living subject. Such method and apparatus would ideally be non-invasive, would be continuously or near-continuously self-calibrating, and would be both useful and produce reliable results under a variety of different subject physiological circumstances, such as when the subject is both conscious and anesthetized. Lastly, such improved method and apparatus would be based primarily on parameters measured from each particular subject being assessed, thereby allowing for calibration unique to each individual.

SUMMARY OF THE INVENTION

The present invention satisfies the aforementioned needs by an improved method and apparatus for assessing hemodynamic properties, including blood pressure, within a living subject.

In a first aspect of the invention, a method of assessing hemodynamic properties including blood pressure within the circulatory system is disclosed. The method generally comprises the steps of: measuring a first parameter from the blood vessel of a subject; measuring a second parameter from the blood vessel; deriving a calibration function based on the second parameter; and correcting the first parameter using the derived calibration function. Once calibrated, the second parameter is monitored continuously or periodically; changes in that parameter are used to indicate changes in the hemodynamic property of interest. In a first exemplary embodiment, the first parameter comprises a pressure waveform, and the second parameter comprises the total flow kinetic energy of blood within the blood vessel. During measurement of the pressure waveform, the blood vessel is applanated (compressed) so as to induce changes in the hemodynamic properties within the blood vessel and circulatory system; the kinetic energy during such applanation is then measured and used to identify one or more artifacts within the pressure waveform. A correction function is then generated based on these artifacts, and applied to the measured pressure waveform to generate a corrected or calibrated waveform representative of the actual pressure within the blood vessel. In a second exemplary embodiment, the maximal velocity of the blood flowing within the blood vessel is determined using an acoustic signal and used to derive a calibration function.

In a second aspect of the invention, an improved method of calibrating a pressure signal obtained from a blood vessel of a living subject using one or more measured parameters is disclosed. Generally, the method comprises: measuring a pressure waveform from the blood vessel; measuring a second parameter at least periodically from the blood vessel; deriving a calibration function based on the second parameter; and correcting the first parameter using the derived calibration function. In one exemplary embodiment, the method comprises measuring the pressure waveform from a blood vessel of the subject; measuring a second parameter from the same blood vessel at least once; identifying at least one artifact within the pressure waveform based on the second parameter; deriving a calibration function based on the measured second parameter and at least one property associated with the at least one artifact; applying the calibration function at least once to the pressure waveform to generate a calibrated representation of pressure within the blood vessel; and continuously monitoring the second parameter to identify variations in blood pressure with time.

In a third aspect of the invention, an improved method of characterizing the hemodynamic response of the circulatory system of a living subject is disclosed. The method generally comprises the steps of: deriving a first functional relationship between first and second parameters associated with a blood vessel under certain conditions; measuring the first and second parameters non-invasively under those certain conditions; identifying at least one artifact within at least one of the measured parameters; and scaling the measurement of the first parameter based on at least the first functional relationship and the at least one artifact.

In a fourth aspect of the invention, an improved method of calibrating a hemodynamic parametric measurement having an error component is disclosed. Generally, the method comprises measuring a hemodynamic parameter associated with a blood vessel; identifying an error source associated with the first parameter; generating a calibration function based on the error source; and correcting the measured hemodynamic parameter using the calibration function. In one exemplary embodiment, the method comprises measuring a pressure waveform from the blood vessel; identifying a periodic variation associated with the kinetic energy (or maximal velocity) of the blood within the blood vessel over time due to respiratory effects; generating a calibration function based on synchronization with the variation in kinetic energy over time; and applying the calibration function to the pressure waveform to correct the waveform for the periodic variation. This respiratory effect is also detectable from the pressure signal, and potentially other signals as well.

In a fifth aspect of the invention, an improved apparatus for measuring hemodynamic properties within the blood vessel of a living subject is disclosed. The apparatus generally a first transducer for measuring a first hemodynamic parameter associated with the blood vessel; a second transducer for measuring a second hemodynamic parameter associated with the blood vessel; and a signal processor operatively connected to the first and second transducers for generating a calibration function based on the signal produced by the second transducer, and applying the correction function to the signal produced by the first transducer. In one exemplary embodiment, the blood vessel comprises the radial artery of a human being, and the apparatus comprises a pressure transducer disposed non-invasively in proximity thereto; an acoustic transducer also disposed in proximity thereto; an applanation device used to applanate the blood vessel; and a processor for processing signals from the pressure and acoustic transducers during applanation of the blood vessel. The acoustic transducer transmits an acoustic emission into the blood vessel and receives an echo therefrom; information regarding the blood's velocity and/or kinetic energy during the applanation is derived from the echo and used to generate a correction function which is then applied to the measured pressure waveform to calibrate the latter.

In a sixth aspect of the invention, an improved computer program for implementing the aforementioned methods of hemodynamic assessment, modeling, and calibration is disclosed. In one exemplary embodiment, the computer program comprises an object code representation of a $C^{++}$ source code listing, the object code representation is disposed on the storage device of a microcomputer system and is adapted to run on the microprocessor of the microcomputer system. The computer program further comprises a graphical user interface (GUI) operatively coupled to the display and input device of the microcomputer. One or more subroutines or algorithms for implementing the hemodynamic assessment, modeling, and calibration methodology described herein based on measured parametric data provided to the microcomputer are included within the program. In a second exemplary embodiment, the computer program comprises an instruction set disposed within the storage device (such as the embedded program memory) of a digital signal processor (DSP) associated with the foregoing hemodynamic measurement apparatus.

In an seventh aspect of the invention, an improved apparatus for analyzing parametric data obtained according to the foregoing methods and utilizing the aforementioned computer program is disclosed. In one exemplary embodiment, the apparatus comprises a microcomputer having a processor, non-volatile storage device, random access memory, input device, display device, and serial/parallel data ports operatively coupled to one or more sensing devices. Data obtained from a subject under analysis is input to the microcomputer via the serial or parallel data port; the object code representation of the computer program stored on the storage device is loaded into the random access memory of the microcomputer and executed on the processor as required to analyze the input data in conjunction with commands input by the user via the input device.

In a eighth aspect of the invention, an improved method of providing treatment to a subject using the aforementioned method is disclosed. The method generally comprises the steps of: selecting a blood vessel of the subject useful for measuring pressure data; measuring the pressure data of the subject non-invasively; generating a calibration function; applying the calibration function to the measured pressure data to produce a calibrated representation of blood pressure within the blood vessel; and providing treatment to the subject based on the calibrated estimate. In one exemplary embodiment, the blood vessel comprises the radial artery of the human being, and the method comprises measuring a pressure waveform from the radial artery via a pressure transducer; using an acoustic wave to measure at least one hemodynamic parameter; deriving a calibration function based at least in part on the measured hemodynamic parameter; calibrating the pressure waveform using the calibration function to derive a calibrated representation of blood pressure useful for diagnosing one or more medical conditions within the subject; and providing a course of treatment to the subject based at least in part on the calibrated representation.

In a ninth aspect of the invention, an improved method for detection of the lumen disposed within a blood vessel is disclosed. The method generally comprises transmitting acoustic energy into the blood vessel; evaluating the signal level of reflections of the acoustic energy as a function of propagation of the energy within the blood vessel, and identifying at least one region of reduced signal level within the reflections. In one exemplary embodiment, a power metric is derived from the A-mode envelope. The integral of the backscattered power as a function of depth is utilized to identify artifacts (e.g., "plateaus") which are used, with appropriate constraints, to detect the depth of the lumen. In a second embodiment, backscattered energy (e.g., A-mode signals) are analyzed using a power calculation performed over pre-selected depth intervals to identify regions of reduced signal level therein.

In a tenth aspect of the invention, an improved method of detecting at least one wall of a blood vessel is disclosed. The method generally comprises transmitting acoustic energy into the blood vessel; detecting at least one region associated with the lumen in the blood vessel; and detecting the location of at least one wall of the blood vessel relative to the lumen; wherein detecting the location comprises analyzing A-mode data derived from the transmitted acoustic energy. In one embodiment, the wall is detected by comparing the integrated power at a given depth with the average lumen power. In another embodiment, the level (amplitude) of the envelope-squared signal is compared to that of the lumen.

In an eleventh aspect of the invention, an improved method of determining the diameter of a blood vessel is disclosed. The method generally comprises transmitting acoustic energy into the blood vessel; detecting the region associated with the lumen in the blood vessel; detecting the location of a first wall of the blood vessel relative to the lumen; detecting the location of a second wall of the blood vessel relative to the lumen; and determining the diameter of at least a portion of the blood vessel based at least in part on the locations of the first and second walls.

In a twelfth aspect of the invention, an improved method of assessing one or more hemodynamic parameters associated with a living subject using lumen detection is disclosed. The method generally comprises transmitting acoustic energy into a blood vessel; detecting the lumenal region associated with the blood vessel; detecting at least one wall associated with the blood vessel based on the detection of the lumen; and analyzing changes in the position of the at least one wall as a function of an applied stress to estimate the hemodynamic parameter(s) of interest. In one exemplary embodiment, the method comprises analyzing A-mode signals to detect the front and back arterial walls (via the lumen), and mapping variations in arterial diameter as a function of applanation pressure onto a pressure waveform to determine arterial diastolic blood pressure.

In a thirteenth aspect, an apparatus for locating a blood vessel having a lumen is disclosed. In one embodiment, the apparatus comprises: a transducer element adapted to transmit acoustic energy into the blood vessel, and a processor element adapted to: (i) determine a power of backscatter energy from the transmitted energy as a function of depth within the blood vessel, (ii) identify at least one artifact associated with a location of the lumen, (iii) compute a power function in a first dimension relative to the location, and (iv) compute a power function in a second dimension relative to the location. The computations substantially determine a location of the blood vessel.

In a fourteenth aspect, a method of locating a blood vessel having a lumen is disclosed. In one embodiment, the method comprises: (i) transmitting acoustic energy into the blood vessel via a transducer, (ii) receiving a signal related to backscattered energy derived from the transmitted acoustic energy at the transducer, and (iii) processing the backscattered energy to identify at least one artifact associated with the lumen at a processor associated with the transducer, the at least one artifact comprising a substantially flat portion of a power profile corresponding to the lumen.

In a fifteenth aspect, an apparatus adapted to detect the location of a blood vessel is disclosed. In one embodiment, the apparatus comprises: (i) an acoustic transducer, (ii) a signal transceiver operatively coupled to the acoustic transducer, and (iii) a processor operatively coupled to the signal transceiver, the processor adapted to perform computations on data received by the signal transceiver in order to compute the location of the blood vessel. The processor is further adapted to: (i)baseband the received acoustic energy data, and (ii) square the basebanded data to produce envelope-squared data.

In a sixteenth aspect, an apparatus for locating a position of a blood vessel having a lumen is disclosed. In one embodiment, the apparatus comprises: (i) a means for transmitting acoustic energy into the blood vessel, (ii) a means for determining power of backscatter energy from the transmitted energy as a function of depth within the blood vessel, (iii) a means for identifying at least one artifact associated with a location of the lumen, and (iv) a means for calculating: a power function in a first dimension relative to the location and a power function in a second dimension relative to the location. The means for calculating are utilized to substantially determine a location of the blood vessel.

In a seventeenth aspect, a method of locating a blood vessel having a lumen is disclosed. In one embodiment, the method comprises: (i) transmitting acoustic energy into the blood vessel via a transducer, (ii) receiving, at the transducer, backscattered energy produced from the transmitted acoustic energy, and (iii) processing, at a processor in signal communication with the transducer, the received backscattered energy to identify at least one artifact associated with the lumen. The identification of the at least one artifact comprises identification of a substantially flat portion of a power profile corresponding to the lumen.

BRIEF DESCRIPTION OF THE DRAWINGS

FIGS. 4a and 4b are graphs illustrating the relationship between blood velocity and reduction of the effective cross-sectional flow area of a blood vessel.

FIGS. 5a-5c are graphs illustrating the relationship between applanation pressure, cardiac sinus rhythm, and arterial wall displacement according to the invention.

FIG. 5d is a graph illustrating the relationship between maximum blood velocity and percentage reduction in flow area (applanation pressure) for both diastolic and systolic pressures.

FIG. 23 is a table listing an exemplary set of (FIR) coefficients used in the quadrature demodulation and filtering method of the present invention.

FIG. 27c is a graphical representation of the normalized integrated power function according to the plateau method of FIG. 27a.

FIG. 27d is a graphical representation of the plateau detection metric used in conjunction with the method of FIG. 27a.

FIG. 32b is a graphical representation of the pressure profile measured by the applanating pressure transducer as a function of time during according to FIG. 32a.

FIG. 36a is a histogram plot of an exemplary end-diastolic "flat spot" detection algorithm according to the invention.

DETAILED DESCRIPTION OF THE INVENTION

Reference is now made to the drawings wherein like numerals refer to like parts throughout.

It is noted that while the invention is described herein in terms of a method and apparatus for assessing the hemodynamic parameters of the circulatory system via the radial artery (i.e., wrist) of a human subject, the invention may also be embodied or adapted to monitor such parameters at other locations on the human body, as well as monitoring these parameters on other warm-blooded species. All such adaptations and alternate embodiments are considered to fall within the scope of the claims appended hereto.

Overview

In one fundamental aspect, the present invention comprises a method of assessing hemodynamic parameters within a living subject by artificially inducing "stresses" on the subject's circulatory system. The response of the circulatory system to these stresses is known or determinable, and useful in identifying artifacts or markers with the observed data. These markers are subsequently used to calibrate measurements of the aforementioned hemodynamic parameters.

For example, as will be described in greater detail below, the present invention is useful at calibrating the blood pressure waveform obtained from a tonometric or surface pressure sensor disposed over the radial artery of a human being, the non-calibrated pressure waveform potentially varying substantially from that actually experienced within the radial artery itself. In one embodiment, the "stress" placed on the artery is applanation (i.e., compression), and the velocity of blood flowing through the area of applanation is monitored to identify markers within the velocity profile. These markers correspond to, inter alia, a state of near zero transmural pressure across the artery wall. In this fashion, an accurate measure of true arterial pressure may be obtained non-invasively. It will be recognized, however, that the invention as described herein may also be readily used in assessing other hemodynamic properties, such as the pressure differential between two locations within a blood vessel, venous or arterial wall compliance, variations in the strength of ventricular contraction, and the like, and accordingly is not limited to the measurement of arterial blood pressure.

Method of Assessing Hemodynamic Properties

Figure 1:
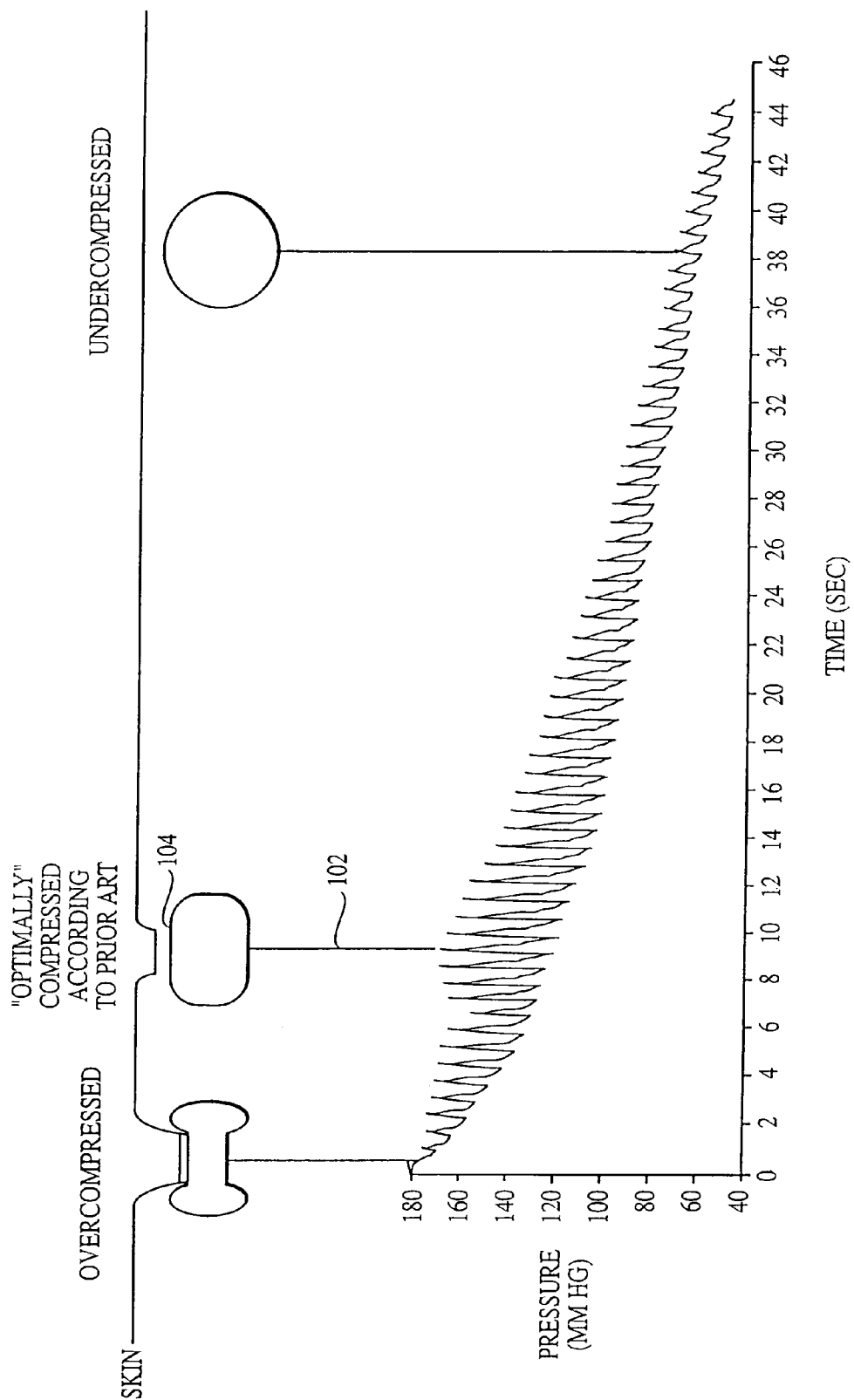
FIG. 1 is a composite graph illustrating the cross-sectional shape of an artery as a function of applied pressure and time according to the prior art "maximum pulsatile" theory.
Figure 2:
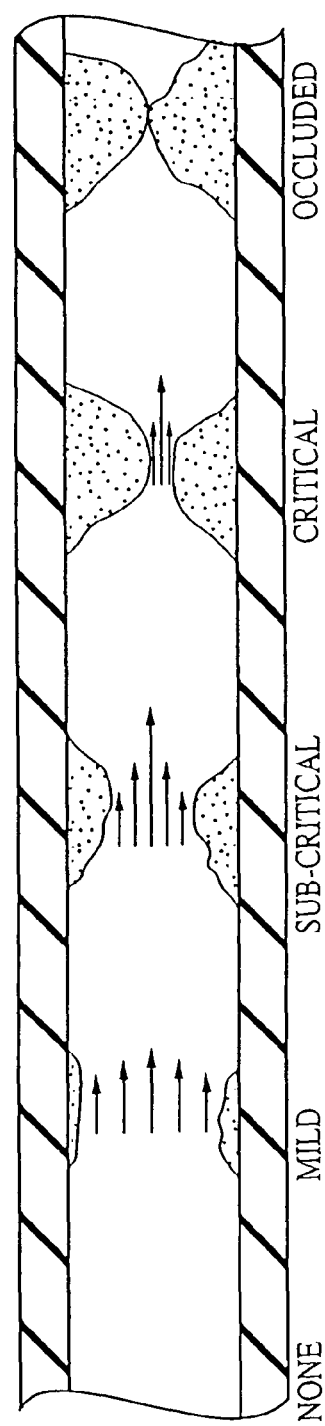
FIG. 2 illustrates a blood vessel with varying levels of stenosis formed on the walls thereof.
Figure 3:
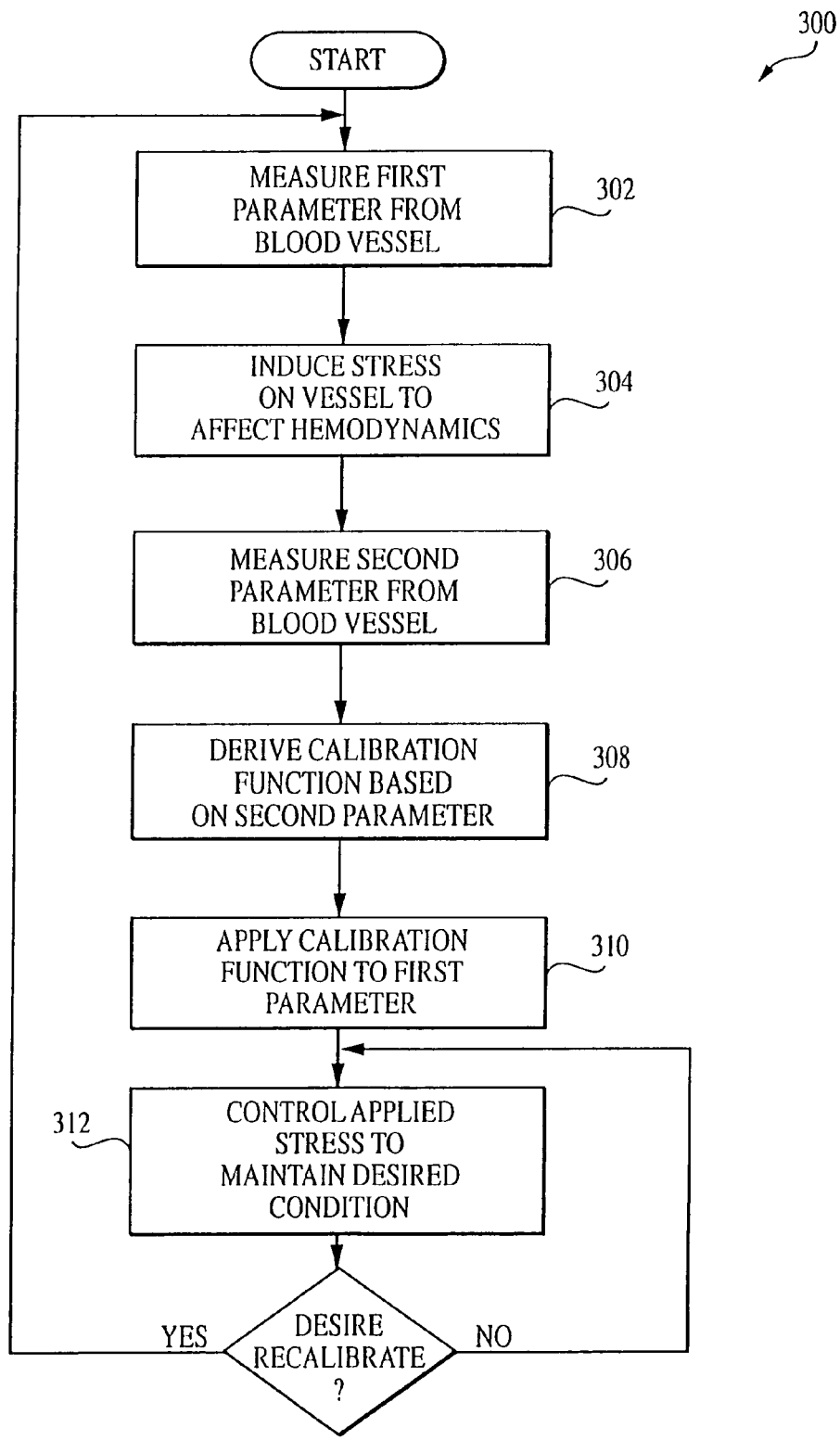
FIGS. 3-3e are a logical flow diagrams illustrating one exemplary embodiment of the method of assessing hemodynamic parameters within the circulatory system of a living subject according to the invention.

Referring now to FIG. 3, the method of assessing hemodynamic properties including blood pressure within the circulatory system according to the invention is described. As shown in FIG. 3, the first step 302 of the method 300 comprises measuring a first parameter from the blood vessel of a subject. In the present context, the parameter measured will be a blood pressure waveform derived from a pressure sensor or transducer disposed in proximity to the radial artery of the subject, as described in greater detail with respect to FIG. 3a herein. It will be recognized, however, that other hemodynamic parameters may be measured as previously noted. Implicit in the measurement of the first parameter is the existence of one or more error sources; i.e., the measured value of the parameter is not wholly representative of, or differs from, the actual value of the parameter existing in the circulatory system of the subject. In the instance of arterial blood pressure, the actual value is that existing within the artery itself, as may be measured by the A-line or "gold standard" technique of invasive arterial catheterization. Reasons for such errors or differences are discussed in more detail below with reference to FIG. 3a.

Next, in step 304 of FIG. 3, a stress is induced on the blood vessel which alters its hemodynamic properties (at least locally), thereby inducing changes in other parameters associated with the vessel or circulatory system as a whole. As discussed with respect to FIG. 3b, this stress comprises in one embodiment applanating or variably compressing the blood vessel as a function of time, thereby inducing changes in, inter alia, the mass flow rate (Q), velocity (v) or velocity gradient, and kinetic energy (KE) of the blood in the region of the applanation. It is noted, however, that stressors other than the applanation stress previously described may be applied to the subject to affect similar or other hemodynamic properties, such as, for example, circumferential occlusion (as would occur with a cuff-like device) to affect arterial cross-sectional area, or the localized introduction of chemical substances into the subject to affect the compliance of the artery. Many such stressor/hemodynamic parameter combinations may be used consistent with the invention.

Next, in step 306, a second parameter associated with the blood vessel is measured in order to facilitate derivation of a calibration function in step 308 below. As discussed in greater detail with respect to FIG. 3c herein, the second parameter in one embodiment comprises total blood flow kinetic energy, since this parameter exhibits certain easily identified "artifacts" as a function of the application of the stressor in step 304. As used herein, the terms "artifact" and marker are used synonymously, and refer to any identifiable feature or relationship existing within a data set. Other parameters which exhibit the same or other artifacts may be used to derive the calibration function however, including, for example, maximum blood velocity, blood vessel cross-sectional area, and blood mass flow rate.

In step 308 of FIG. 3, a calibration metric or function is next derived based on the parametric information derived in step 306. Specifically, one or more artifacts or markers are identified within the parametric data, these artifacts indicating when certain relationships between the actual and measured values of the first parameter of step 302 above exist. As will be discussed with reference to FIG. 3d herein, one embodiment of the process of deriving a calibration function comprises measuring total blood flow kinetic energy within the region of the applied stressor (applanation), and identifying changes within the systolic and/or diastolic velocity profiles as a function of the applanation (correlated to percentage reduction of cross-sectional area of the blood vessel).

In step 310 of the method of FIG. 3, the calibration function derived in step 308 is applied to the measurement of the first parameter of step 302 to generate a corrected or calibrated measurement. Note that if the first parameter is measured continuously (or periodically) as a function of time, the correction function of step 308 may be continuously or periodically applied as appropriate, thereby generating a calibrated measurement of the first parameter in an ongoing or continuous fashion. However, due to a variety of different factors, both the actual "A-line" arterial pressure and the scale or magnitude of the required calibration function may vary as a function of time; hence, any "calibrated" measurement based on the previously calculated calibration function will be in error. In one alternative, the user may simply periodically recalibrate by reapplying the stressor (e.g., performing another applanation sweep), generating an updated correction function, and applying this to the measured value of the first parameter.

However, as is described in greater detail herein below, the present invention advantageously provides the ability to generate a calibration function at a first time $t_1$, and then monitor the second hemodynamic parameter (e.g., maximum velocity, kinetic energy, area, or flow) continuously for indications of variation of the measured parameter. This is accomplished in step 312 of the method 300 by controlling the external pressure applied to the artery so as to establish a predetermined relationship between true arterial and external pressure, as described further below.

In step 312, the pressure applied to the artery is controlled to selected value of the first parameter so as to maintain the pressure across the artery wall (i.e., "transmural pressure") within the artery at or near a desired value. This process is referred to herein as "servoing" to a particular value. As discussed in detail with reference to FIGS. 5a-5d herein, this servoing generates a particular blood flow kinetic energy in the area of the applanation; changes in this kinetic energy are then used to identify changes in the true arterial pressure. This "continuous calibration" is a desirable attribute of the present invention, since the continued, accurate measurement of hemodynamic parameters with the blood vessel of a subject is of critical importance, especially in the context of surgery or other such life-threatening evolutions where arterial blood pressure is used as the basis for moment-to-moment decisions on treatment of the subject.

Figure 3A:
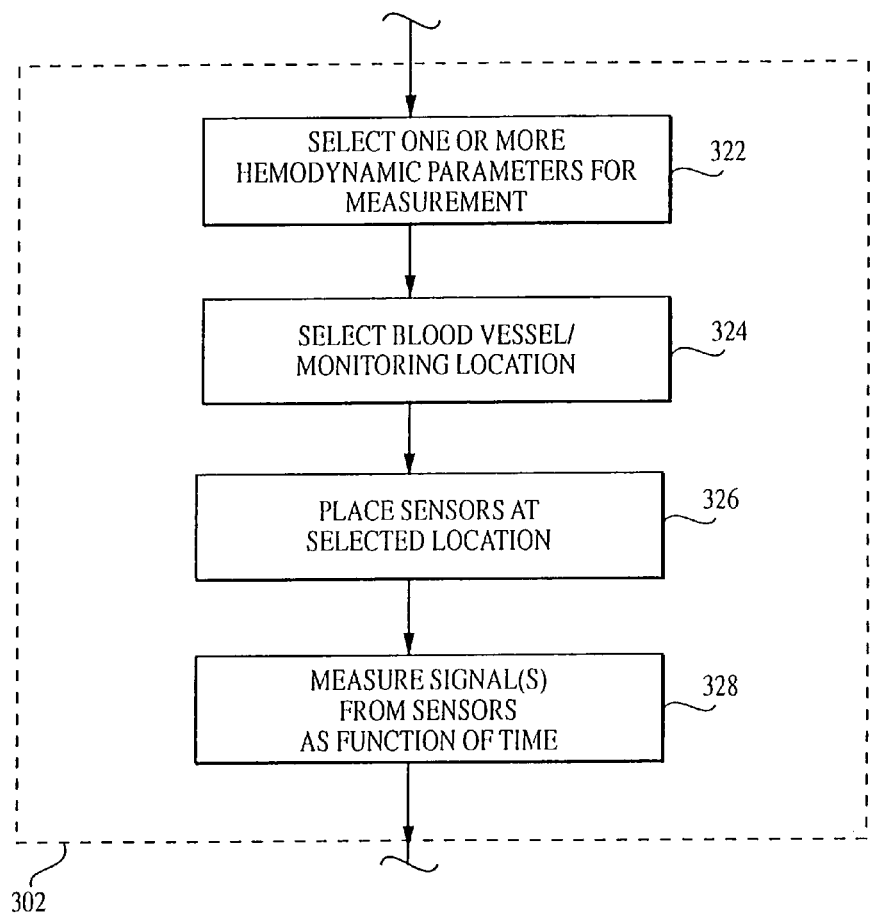

Referring now to FIG. 3a, one embodiment of the method of measuring one or more hemodynamic parameters within a living subject (step 302 of FIG. 3) is described. The first step 322 of the method 320 of FIG. 3a comprises selecting one or more hemodynamic parameters for measurement. Selection of the parameter(s) to be measured is a function not only of the condition to be assessed, such as the subject's blood pressure or severity of stenosis with an artery, but also on the monitoring location selected in step 324 below (i.e., certain parameters may only be measured at certain locations due to physical or other limitations, as in the case of a localized stenosis within an artery which is physically located at a discrete point).

Next, in step 324, a blood vessel within the body of the subject is selected for monitoring. Due to its accessibility and relative proximity to the surface of the skin, the radial artery of the human being is an excellent location for monitoring hemodynamic parameters within the circulatory system, although it will be appreciated that other locations on the human being (or other species) may be used for this purpose. As noted above, the location of monitoring also may be related to or determined by the type of condition to be assessed or monitoring to be performed. Of course, multiple monitoring locations may be employed, whether sequentially or in parallel, with the methods of the present invention.

With respect to the radial artery of the human being, it is further noted that anecdotal evidence suggests that the radial artery is only minimally affected by arterial diseases, including stenosis and calcification due to diabetes. The reasons for this observed behavior are beyond the scope of this discussion; however, this behavior is of some significance to the discussion of applanation stress provided herein with respect to FIG. 3b, since the presence of pre-existing arterial disease such as medial calcification could impact the ability to accurately measure arterial blood pressure. By selecting the radial artery when performing blood pressure measurements, which utilize controlled applanation as the applied stress, the user is effectively insulated from many potential error sources relating to pre-existing stenosis or calcification.

Next, in step 326 of FIG. 3a, one or more parametric sensors capable of measuring or sensing the selected parameter(s) is/are disposed in proximity to the selected blood vessel. In the case of measuring blood pressure on the radial artery of the human, a pressure sensor (transducer) is disposed physically in contact with the skin on the interior surface of the wrist, so as to be atop the radial artery. The transducer may be one of the well understood silicon strain gauge type, piezoelectric type, or any other type capable of producing a pressure signal in a known relation to the pressure applied to the surface thereof. Methods and apparatus for positioning the transducer(s) such that optimal signal coupling and sensing are achieved are also well known in the blood pressure measuring arts, and accordingly will not be described further herein. Note that while in contact with the skin of the wrist, the transducer(s) are initially maintained in a state of low or zero compression of the underlying tissue/artery, for reasons to be more fully explained herein.

In step 328, a signal is measured from the transducer(s) as a function of time. The signal may be measured discretely (e.g., at a predetermined interval) or continuously, depending on the desired frequency of monitoring. In the case of the exemplary pressure transducer previously described, the output signal for a continuous measurement will comprise a time variant waveform. In the case of arterial blood pressure, the waveform will generally track the actual "gold standard" arterial pressure, yet will include error or offset which varies with the pressure changes according to the various phases of the cardiac cycle. This time variant, non-linear error, or "variable error" between the measured and actual pressure waveform presents an additional complexity in the measurement process, one which the present invention is particularly well adapted to overcome as will be described in greater detail below.

Figure 3B:
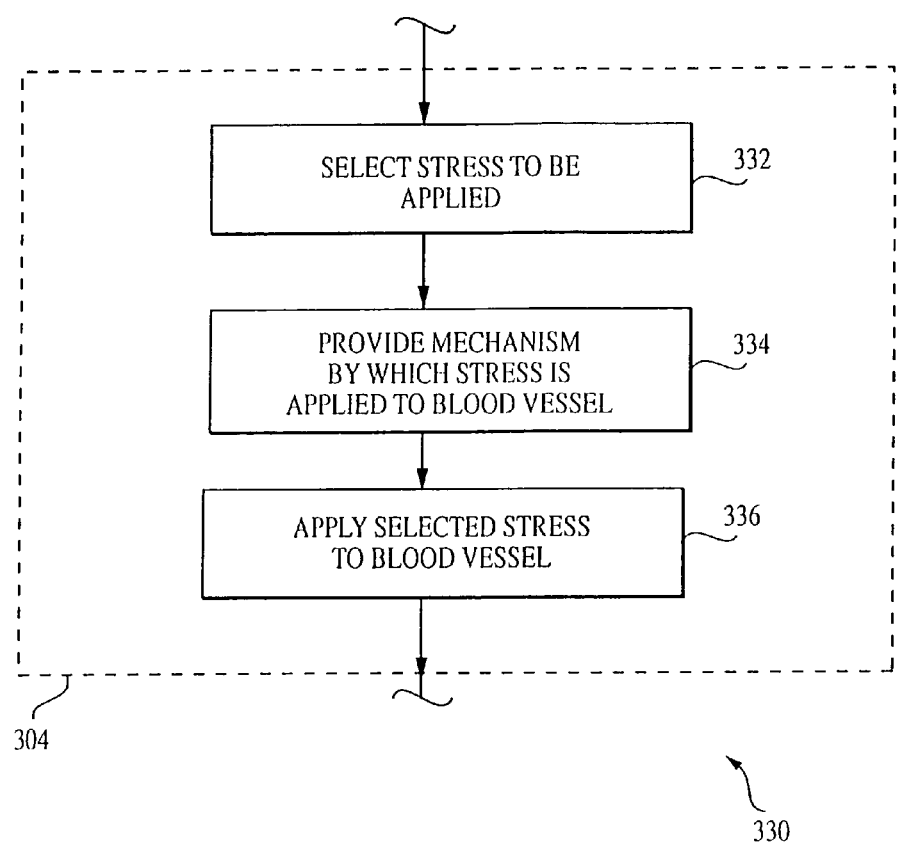

Referring now to FIG. 3b, one embodiment of the method of inducing one or more stresses on the circulatory system of the subject (step 304 of FIG. 3) is described in detail. In the first step 332 of the method 330, a stress to be applied is selected. As used herein, the term "stress" (or "stressor") refers to any physical or physiological change within the circulatory system of the subject which is artificially induced. In the present embodiment, the stress to be applied comprises applanation, or physical compression of the selected (radial) artery as a function of time. An applanation "sweep", as used herein, generally refers to the steady application of increasing or decreasing pressure to the artery in a direction generally normal to the surface of the skin overlying the artery. The concept of applanation is simply illustrated by one placing one wrist between the thumb and forefinger of the other hand, thumb atop the interior portion of the wrist, and slowly increasing pressure on the radial artery until the artery is occluded. It will be recognized, however, that as a general proposition, applanation as used herein may take on any variety of different forms, such as (i) a continuous linear rate of increasing or decreasing compression over time; (ii) a continuous non-linear (e.g., logarithmic) increasing or decreasing compression over time; (iii) a non-continuous or piece-wise continuous linear or non-linear compression; (iv) alternating compression and relaxation; (vi) sinusoidal or triangular waves functions; or (vi) random motion (such as a "random walk"). All such forms are considered to be encompassed by the term "applanation."

Referring to FIGS. 4a and 4b, the hemodynamic effects of applanation are described in detail. As will be readily recognized, the increasing applanation of an artery 400 such as the radial artery of the human results in a reduction in the effective cross-section of the artery. Similar to the arterial stenosis previously described, the applanation 402 reduces the flow area within the artery, thereby resulting in increased blood velocity (v) through the restriction to maintain a constant volumetric flow. This relationship is well understood in the fluid dynamics art. The profile of velocity across the reducing flow area is altered as well, as illustrated by the velocity gradient 404 of FIG. 4a. Hence, a higher maximum velocity, a higher velocity gradient, and a greater energy or pressure gradient across the restricted flow area result from applanation.

FIG. 4b illustrates the peak or maximum flow velocity within the artery as a function of percent reduction of the flow area of the artery. Total blood flow kinetic energy is similarly related to area due in part to its relationship to velocity, albeit somewhat more difficult to derive as described in greater detail below. Note that for the purposes of simplicity in the present discussion, the percent reduction of flow area is assumed to be directly proportional to the applanation pressure applied at the tissue (skin) surface, although in reality this relationship is substantially more complex as described further below. Further, FIG. 4b is generally illustrative of "steady state" operation, and does not examine the effects of variation in pressure due to, for example, the normal cardiac cycle, also discussed in greater detail below.

As illustrated in FIG. 4b, in the region of low applanation pressure 410, the percentage reduction of the flow area is small, and the effects on flow velocity and gradient are minimal. Volumetric blood flow (Q) is unaffected. As applanation pressure increases (region 412), the flow area is further reduced, and while the volumetric flow is maintained, the blood velocity, velocity gradient, pressure gradient, and kinetic energy begin to increase correspondingly. As applanation pressure further increases, the flow area is substantially reduced, and velocity, velocity gradient, pressure gradient, and kinetic energy increase substantially, while still maintaining volumetric flow under normal metabolic demand. In the stenotic artery, this region 414 corresponds to "sub-critical" stenosis, i.e., the level of stenosis where the subject's excess volumetric capacity is significantly reduced, generally with few or no attendant symptoms. The appellation of "sub-critical" refers to the fact that the patient is asymptomatic with adequate tissue perfusion under normal metabolic demand, and only becomes symptomatic when the demand increases as occurs with exercise.

A further reductions in flow area produces a transition through what is known as the "critical" region 416; in the critical region, the flow area is so reduced so that there is inadequate energy to overcome the increased flow resistance, and volumetric flow is no longer maintained. Between these regions 414, 416, a velocity "peak" 420 is formed. Anecdotal evidence suggests that this peak 420 occurs roughly at point of 50% reduction in arterial diameter (corresponding roughly to 75% reduction in flow area). As a result, the blood velocity and the volumetric flow, and the flow kinetic energy distal to the stenosed area drop precipitously with further reduction in flow area. As the artery becomes fully occluded and flow area approaches zero (region 418), the volumetric flow Q approaches zero, as does blood velocity and flow kinetic energy.

Examination of FIG. 4b yields important information in terms of characterizing one response of the circulatory system to one applied stress. Specifically, the behavior of velocity as a function of applanation, and most notably the increase in maximum velocity within the velocity profile, allow the identification of the point where the pressure within the artery is effectively equal to that applied to the wall of the artery via external applanation. This condition is referred to herein as a condition of "zero transmural pressure". During the applanation sweep illustrated in FIGS. 4a and 4b, a point is reached at which the external pressure applied to the exterior of the artery wall is just offset by the internal pressure within the artery. Until this point is reached, no significant reduction in flow area (and resulting attendant changes in velocity, velocity gradient, volumetric flow (Q), or kinetic energy as previously described) occurs. However, as the applied pressure exceeds the arterial internal pressure, the diameter and cross-sectional area of the artery begin to be reduced, and the maximum flow velocity and velocity gradient begin to increase (region 414 of FIG. 4b). This increase in maximum velocity (and kinetic energy) is used in the present embodiment as a "marker" of the point at which the transmural pressure is roughly equilibrated.

However, as previously discussed, the circulatory system is not a static system, but rather dynamic and subject to significant intra-arterial pressure fluctuations, both due to the normal cardiac cycle, as well as other factors such as respiration (discussed below). Hence, such pressure fluctuations must also be considered when measuring hemodynamic properties, particularly intra-arterial pressure.

Referring now to FIGS. 5a-5d, the response of the circulatory system under the aforementioned dynamic pressure fluctuations is described. FIG. 5a illustrates a normal sinus cardiac rhythm 500 for a human being. Within this sinus rhythm 500 are both systolic periods 502 and diastolic periods 504 corresponding to various ventricular functions within the heart, as is well understood in the medical arts. These effectively represent maxima and minima within the sinus rhythm 500, and for the intra-arterial pressure.

FIG. 5b illustrates the displacement of the arterial wall as a function of the aforementioned sinus rhythm 500 of FIG. 5a, and the external applanation pressure applied to the artery per FIG. 5c. Two opposed arterial walls 510, 512 are illustrated in FIG. 5b for sake of clarity, although they are effectively mirror images of one another in terms of pressure response. As is well known in the art, arterial walls are typically (in the healthy human) substantially compliant vessels having significant elasticity and resiliency. Hence, as pressure within the vessel is increased, the opposing walls 510, 512 of the artery tend to deflect outward increasing the diameter of the artery, much as a balloon under inflation. Similarly, as intra-arterial pressure is reduced, the resiliency of the artery walls reduces the diameter. It is well known that human arteries cyclically expand and contract to some degree during the normal cardiac cycle.

As shown in FIG. 5b, variations in blood pressure within the artery deflect the walls of the artery outward to a maximum diameter 516 corresponding to the systolic pressure 502, and allow the artery walls to collapse to a minimum diameter 518 corresponding to the diastolic pressure 504. As the applanation pressure applied to the exterior of the artery (FIG. 5c) increases, the previously described condition of zero transmural pressure is reached successively for both the systolic and diastolic pressures. Specifically, with increasing applanation pressure, zero transmural pressure at the diastolic (lower pressure) condition 520 is achieved first, followed by zero transmural pressure at the systolic (higher pressure) condition 522. Considering the diastolic condition 520 first, as applanation pressure is increased beyond the zero transmural pressure condition, the effective diameter (and flow area) of the artery begins to progressively decrease, resulting in the increase in flow gradient and peak blood velocity and kinetic energy as previously described. As applanation pressure increases well above the diastolic pressure, the artery more completely closes during the diastolic portion of the cardiac cycle at point 527. Similarly, with increasing applanation pressure, the diameter of the artery at the systolic condition 522 also begins to decrease, with similar results, until the artery is completely collapsed under both diastolic portions 527 and systolic portions 529 of the cardiac cycle. Based on the foregoing behavior, two curves may be constructed (FIG. 5d) relating the variation in maximum blood velocity and percent flow area reduction (applanation pressure), both for the diastolic condition 520 and the systolic condition 522. Note that the velocity "peak" 524 of the systolic condition 522 occurs at a higher level of applanation than the corresponding peak 526 for the diastolic condition 520, since greater external pressure must be applied to collapse the artery in the former as opposed to the latter. It is further noted that at pressures falling between the systolic and diastolic maxima and minima of FIG. 5a, a family of curves similar to those of FIG. 5d may be constructed, such a family of curves being useful in characterizing the behavior of the artery and associated hemodynamic parameters during the entire cardiac cycle.

As with the velocity curve of FIG. 4b, the curves of FIG. 5d are useful for marking the point during the applanation sweep at which zero transmural pressure is achieved, both during the diastolic and systolic portions of the cardiac cycle (or any portion there between). The utility and application of this information is described in detail with reference to FIGS. 3d-3e herein.

While the foregoing exemplary application of compressive or applanation stress is useful in the measurement of, inter alia, blood pressure within the selected artery, it will be recognized that other types of stresses may be applied to induce response within the circulatory system. Artifacts or "markers" associated with these stresses may be utilized in a fashion generally analogous to that for the applanation stress; i.e., by correlating the presence of the markers or known relationships with certain hemodynamic conditions within the circulatory system in general or blood vessel in particular. Hence, the method of FIG. 3b is in no way limited to the use of compressive stress.

Returning again to FIG. 3b, the second step 334 of the method 330 of applying stress to the selected blood vessel comprises providing a mechanism by which such stress can be applied. In the context of applanation as described above, there is particular utility in using the aforementioned pressure transducer (used to measure the pressure waveform) as the means by which the artery is applanated, since this arrangement permits the pressure measurement to be made precisely at the point of applanation. An applanation mechanism of this type is described herein with respect to FIG. 12. However, it will be appreciated that a separate pressure transducer and applanation mechanism, or even other configurations, may be used in conjunction with the present invention.

In step 336 of FIG. 3b, the provided mechanism is utilized to apply the stress to the selected artery. In the specific case of applanation, an applanation "sweep" as previously described is applied, such that the pressure transducer is asserted at continually increasing levels of pressure against the skin of the wrist, thereby compressing the underlying artery. As with the method 320 of FIG. 3a, optimal placement and orientation of the applanation device over the artery may be determined using any variety of well understood prior art techniques, including those described in Assignee's co-pending U.S. patent application Ser. No. 09/342,549, entitled "Method And Apparatus For The Noninvasive Determination Of Arterial Blood Pressure" filed Jun. 29, 1999, and Ser. No. 09/815,982 entitled "Method and Apparatus for the Noninvasive Assessment of Hemodynamic Parameters Including Blood Vessel Location" filed contemporaneously herewith, both being incorporated herein by reference in their entirety. It is noted, however, that the foregoing method 320 maybe utilized even with non-optimal transducer placement (e.g., by manual placement by the individual administering treatment), so long as the signal coupling in such cases is adequate.

Figure 3C:
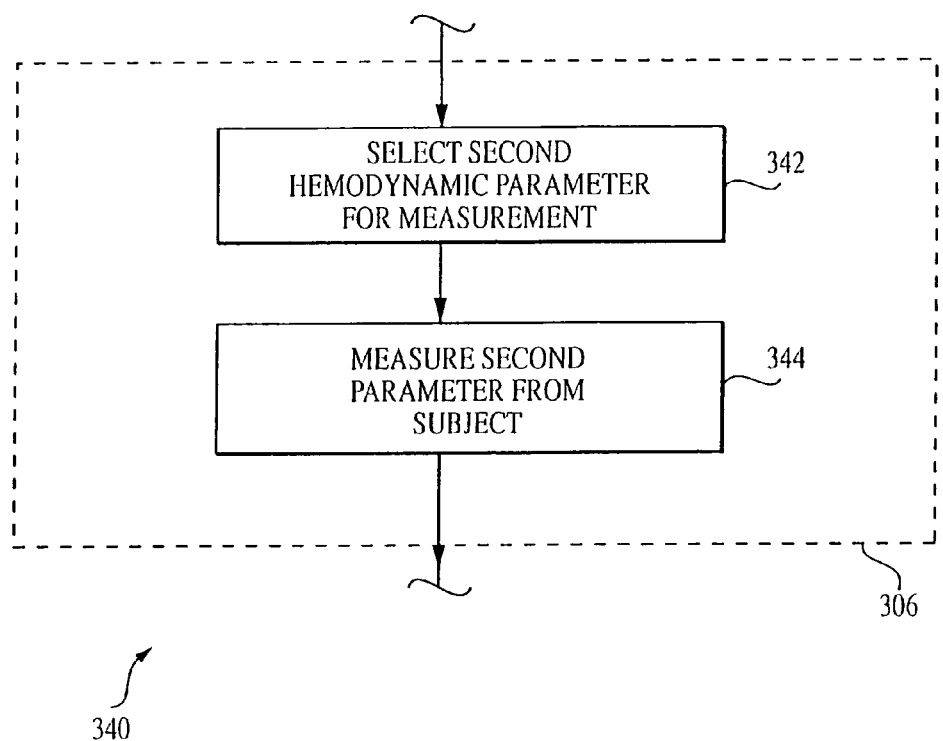

Referring now to FIG. 3c, one embodiment of the method of measuring a second hemodynamic parameter associated with the blood vessel (step 306 of FIG. 3) to facilitate derivation of a calibration function is described. In the first step 342 of the method 340, the second hemodynamic parameter to be measured is selected. Election of this parameter is in some respects coupled to the selection of the first hemodynamic parameter to be measured (FIG. 3a), as well as the selection and application of stress on the circulatory system (FIG. 3b). In the context of blood pressure measurement and the use of compressive stress (applanation) as previously described, several "secondary" hemodynamic parameters may conceivably be used to generate a calibration function, including, without limitation, blood velocity, total blood flow kinetic energy, and blood volumetric flow rate, as well as any variations or combinations thereof. Total blood flow kinetic energy is one particularly useful parameter to measure, as it contains one or more readily observable markers of the zero transmural pressure condition or other useful relationships. The total flow kinetic energy is also less prone to errors than certain other parameters, since it utilizes velocity information obtained across the whole blood vessel, as well as the amplitude information. Additionally, the peaking in the kinetic energy is more dramatic than the peaking in other parameters such as maximum velocity.

Next, in step 344, the selected "secondary" parameter is measured using an appropriate sensor or measurement technique. In the case of kinetic energy or blood velocity measurements, several well known techniques exist to generally measure these parameters non-invasively. Of particular note is the use of acoustic energy (e.g., ultrasound) to measure blood velocity. Specifically, acoustic measurement techniques generally employ the well known Doppler principle in measuring velocity, wherein the frequency shift associated with echoes reflected by the blood flowing within the blood vessel is analyzed to provide a measurement of blood velocity. Numerous different variants of acoustic blood velocity measurement techniques exist, including the use of a continuous acoustic wave (CW), and acoustic pulses (pulsed Doppler). Such techniques are well known and understood, and accordingly will not be described further here.

Similarly, acoustic measurement techniques may be used to derive a measurement of the kinetic energy of the blood flowing within the subject blood vessel. It is noted that as a result of the complex blood velocity gradient created within the blood vessel during applanation (FIG. 4a), calculation of the kinetic energy of the blood within the blood vessel as a whole is not simply proportional to the square of the maximum blood velocity described above; rather, estimation of the kinetic energy requires the application of summation or integration techniques which capture the complexity of this gradient. Such summation/integration techniques for calculating blood kinetic energy are well known in the art, and accordingly are not described further herein.

In another embodiment, the applanation (external) pressure at which the desired marker is exhibited may be determined using time-frequency methodology as described in Assignee's co-pending U.S. patent application Ser. No. 09/342,549 previously incorporated herein. Using this time-frequency methodology, the applanation pressure at which the transmural pressure equals zero can be determined by constructing time-frequency representations of the acoustic energy reflected within the artery. When the time-frequency distribution is maximized, the zero transmural pressure condition is achieved. Hence, the maximal time-frequency distribution acts as yet another marker for the purposes of the present invention.

In yet another embodiment, the so-called acoustic "A-mode" may be used to monitor the second hemodynamic parameter. In this approach, acoustic waves are generated and transmitted into the blood vessel; reflections or echoes from the transmissions are received and analyzed to determine the relationship between the time of transmission and the time of receipt. Through such analysis, the relative diameter of the artery at different points in time, and different points within the cardiac cycle, can be determined. Analogous to the well known time domain reflectometer (TDR), the A-mode technique in one embodiment utilizes reflections generated by the transition of an acoustic wave across various boundaries between materials of different acoustic properties (e.g., the "near" artery wall/tissue boundary, the "near" artery wall/blood stream boundary, the blood stream/"far" artery wall boundary, etc.). Specifically, the relative timing of these reflections is analyzed to determine the distance between the various boundaries. Knowing the propagation speed of the acoustic wave through the different media, the distance between the reflective boundaries (i.e., tissue thickness, artery diameter, etc.) can be determined. Recalling that per FIG. 5b, the deflection of the artery walls (under both systolic and diastolic portions of the cardiac cycle) varies as a function of applanation pressure, changes in the arterial diameter (and area, related thereto) may be used as "markers" of the zero transmural pressure condition, or other conditions of significance, analogous to the use of increasing maximum velocity to identify such conditions. Specifically, when the diameter of the artery jus t begins to decrease, the externally applied pressure just slightly exceeds the internal arterial pressure at that point in time.

Other techniques for assessing hemodynamic parameters using A-mode acoustics may also be employed. Such alternate techniques are discussed in greater detail with respect to FIGS. 17-39 herein.

It will further be recognized that other acoustic modalities may be employed in conjunction with the invention described herein, including for "M-mode" (motion mode) or "B-mode" (brightness mode) both of which are well known in the acoustic signal arts.

Despite the use of acoustic waves in each of the foregoing embodiments for measuring the secondary hemodynamic parameter and markers associated therewith, it will be recognized that other non-acoustic techniques may be applied to identify such markers. For example, other methods of accurately measuring arterial diameter/area, such as using interferometry, may be employed to identify the zero transmural pressure condition. All such techniques are considered to fall within the scope of the present invention.

Figure 3D:
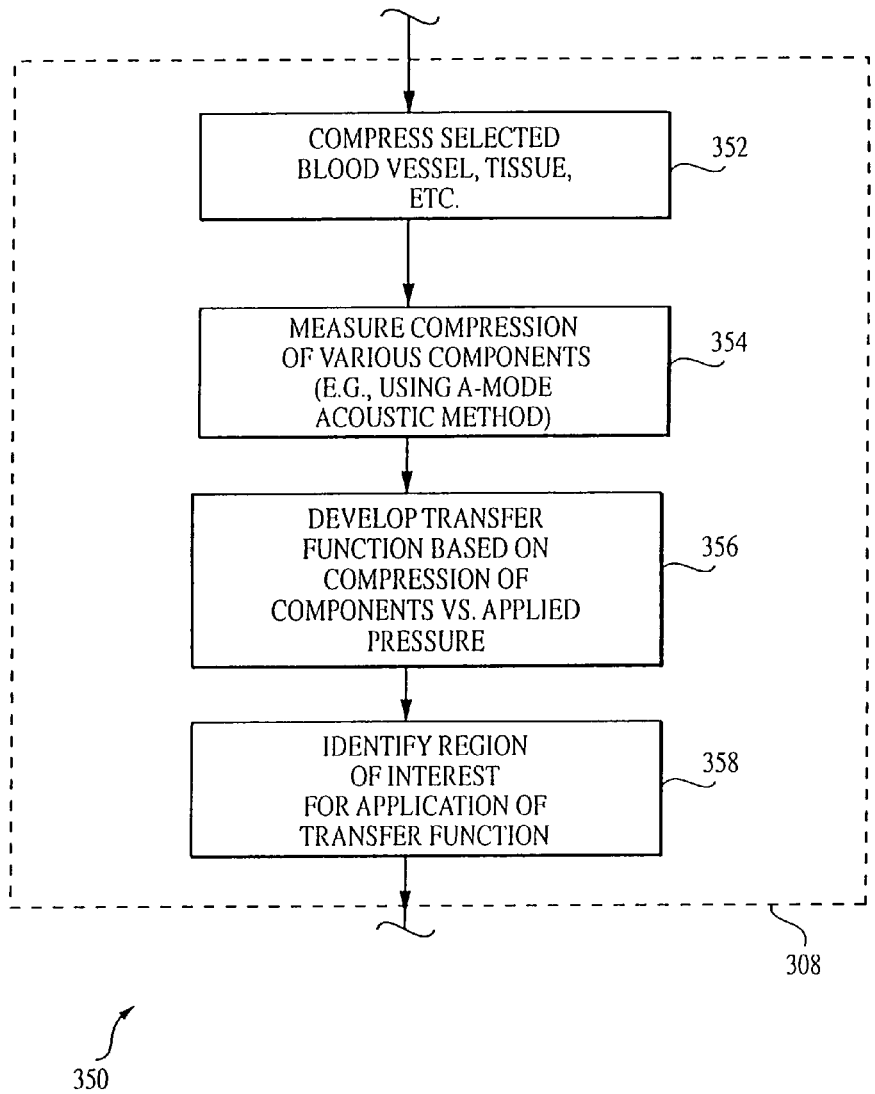

Referring now to FIG. 3d, the stressor magnitude at which the desired hemodynamic condition is achieved (e.g., applanation pressure at which zero transmural pressure is achieved) is correlated to the actual or true arterial pressure. In the simple case where there is a high degree of coupling between the applied stress and the stress actually felt by the blood vessel, the measured stress can be equated to the actual stress. Specifically, in the context of arterial blood pressure measurements where applanation (compressive) stress is applied, the pressure applied by the applanation device and sensed by the associated pressure transducer could be equated to the actual arterial pressure when the artifact or "marker" condition is observed. For example, if increasing blood kinetic energy correlates to a condition of zero or near-zero transmural pressure as previously discussed, the pressure applied against the artery wall when such increase in kinetic energy was observed would equate to true intra-arterial pressure. Hence, if the coupling between the point of pressure application (e.g., skin) and the artery wall was very high, the pressure applied at the point of application would approximate that applied to the artery wall, and therefore would also approximate the pressure within the artery.

However, as previously discussed, the tissue, tendons, and skin interposed between the artery wall and the pressure transducer in many cases create a complex relationship between the pressure applied by the transducer (or applanation mechanism) and the pressure actually felt by the artery wall. Simply stated, some of the pressure applied to the skin is used to compress this interposed material; hence, only a portion of the externally applied pressure is actually felt by the artery wall. Additionally, it is noted that tissue is also present below the blood vessel and above bone; some loss occurs in compressing this tissue as well.

Therefore, depending on the tissue compliance and degree of coupling for a given subject, a certain amount of error in the measurement of arterial pressure will be introduced when basing such a measurement on the externally applied pressure (e.g., that measured by the pressure transducer).

One prior art approach to this problem was to model the response of interposed material (for example, as a system of springs having linear force constants), and correct the pressure measured by the pressure transducer based on this model. This approach, however, is only as good as the model used; different subjects with different tissue thickness, density, and compliance values (as well as the location of the tendons and bone relative to each other and the artery) will respond differently, and these differences are not accounted for in such models. Furthermore, even for a single subject, changes in the response of the tissue and arteries of that subject may occur over time or as a function of externally induced stresses. For example, when an anesthetic is introduced into the circulatory system of the subject, a given artery may become substantially more compliant, thereby losing much of its resiliency. This change in compliance alters the relationship between actual and measured arterial pressure, and accordingly reduces the accuracy of any blood pressure estimate based thereon.

In contrast, the methodology of the present invention overcomes this significant limitation by measuring the actual response of the interposed tissue and material for each subject as opposed to generically modeling it as in the prior art. Specifically, the present invention generates a functional representation of tissue and arterial compliance based on actual compression of these components.

Figure 6:
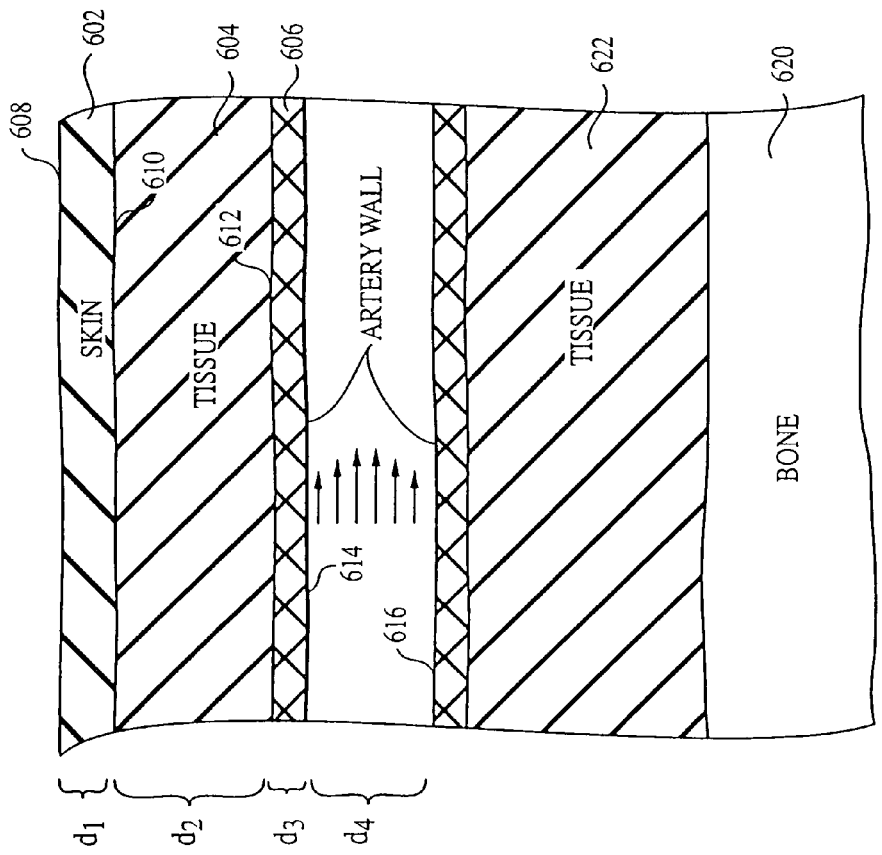
FIG. 6 is a cross-section of a portion of a typical human wrist illustrating the relationship between the artery, skin, and interposed tissue and bodily components.
Figure 7B:
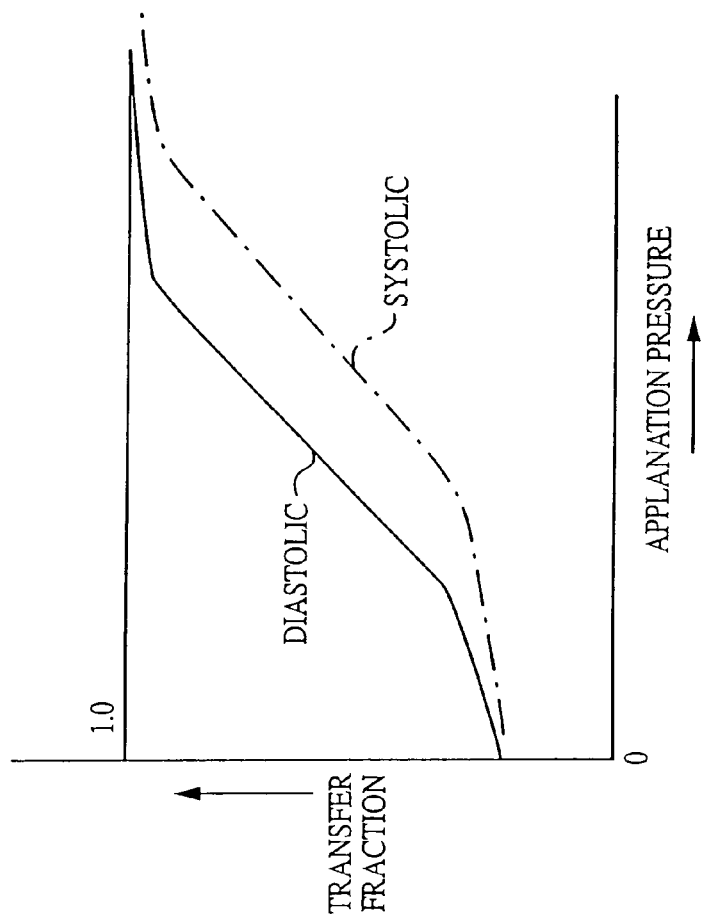
FIGS. 7a-7b are graphs illustrating an exemplary transfer function and transfer fraction, respectively, for the cross-section of FIG. 6, for both systolic and diastolic conditions.
Figure 7A:
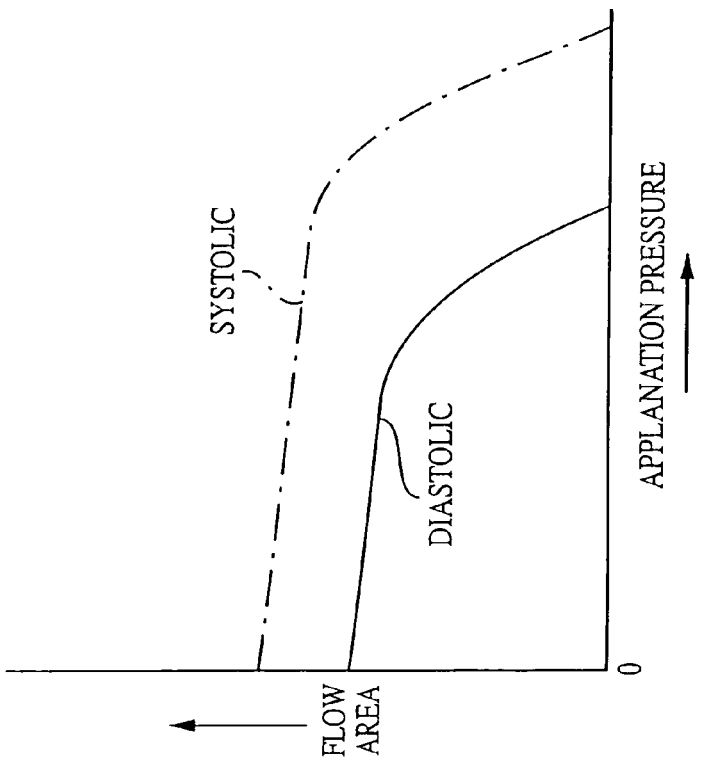

In the exemplary embodiment of the method 350 illustrated in FIG. 3d, the aforementioned "A-mode" acoustic transmission is used to monitor the compression of each of the components interposed between the applanation device and the artery interior wall. The compression of these components (step 352) proceeds generally according to their individual material properties, which are unknown and interdependent and therefore exceedingly complex to model. However, by making direct observations of the actual compression of these components, the transfer function existing between the externally applied force and the force applied at the interface of the artery wall and the pressurized fluid (blood) within the artery can be approximately determined for each individual, and for the specific location being applanated. As illustrated in FIG. 6, the region between the interior wall of the artery and the surface of the skin above the artery may be divided into several discrete regions, such as the skin 602, tissue 604, and artery wall 606. The distances $d_1$, $d_2$, $d_3$ and $d_4$ between the surface of the skin 608 and the skin/tissue boundary 610, the skin/tissue boundary and the tissue/artery boundary 612, the tissue/artery boundary and the artery/blood boundary 614, and the artery/blood boundary 614 and the blood/artery boundary 616, respectively, are measured in step 354 using A-mode acoustic transmissions which identify reflections from these boundaries, as previously described. Additionally, the relative location of bone 620 and tendon 618 have great influence on the transfer loss. In effect, a restoring spring force of sorts exists between the tendon 618 and tissue 622 and bone 620 and tissue 622. The loss of pressure transfer is at least partially associated with overcoming these restoring forces, as well as with the compliance of the tissue. Hence, during applanation (and during specific portions of the cardiac cycle), a transfer function between artery diameter (and flow area) and applied external pressure is developed per step 356. Specifically, for the diastolic and systolic portions of the cardiac cycle, different transfer functions will exist as illustrated in FIGS. 7a-7b. At low applied pressure (as measured relative to the actual intra-arterial pressure), relatively little compression of interposed tissue, underlying tissue/tendon, artery wall, etc. has occurred, and hence further increases in applied pressure generally contribute disproportionately to further compression of these components. At higher values of applied pressure, the interposed components are substantially compressed, and a relatively small fraction of any further increases in applanation pressure is used to compress the interposed and underlying components. Hence, in general, the "transfer fraction", or the ratio of transferred pressure to applied pressure, increases as a function of applied pressure, as illustrated in FIG. 7b. In the theoretical case of free-floating incompressible materials interposed between the pressurized blood in the artery and the transducer, the transfer fraction would be 1:1, indicating complete coupling.

The foregoing derived transfer function, can then be utilized to correct the error of the incomplete pressure transfer measured by the pressure sensing introduced by the interposed tissue, etc., by identifying the regions of interest per step 358. For example, if the zero transmural pressure condition within the artery during the diastolic portion of the cardiac cycle is achieved when a pressure of 60 mm Hg is measured, the true diastolic pressure will be some percentage higher, where the percentage is determined by the degree of pressure transfer loss. The transfer fraction for that monitoring location indicates the fraction or percentage of the intravascular pressure which is transferred to the surface of the pressure measuring sensor.

Note that the transfer function and/or transfer fractions may be represented and stored in any variety of different formats after measurement, such as in look-up tables in a digital random access memory as described further below with respect to the apparatus of FIG. 12. Furthermore, it will be readily appreciated that while the method 350 described above is used to determine the transfer fraction for one or more discrete pressure conditions (i.e., systolic and/or diastolic pressures), the transfer fraction may be readily determined for a range of pressures, thereby forming a transfer function as a function of pressure, as described in greater detail below. Hence, if the blood pressure of the subject does vary, the present invention utilizes this transfer function to correct the measured value of pressure within any pressure range.

Similarly, it will be recognized that methods of determining the transfer function/fraction other than the A-mode acoustic technique may be utilized, either alone or in conjunction with the A-mode technique.

Figure 8:
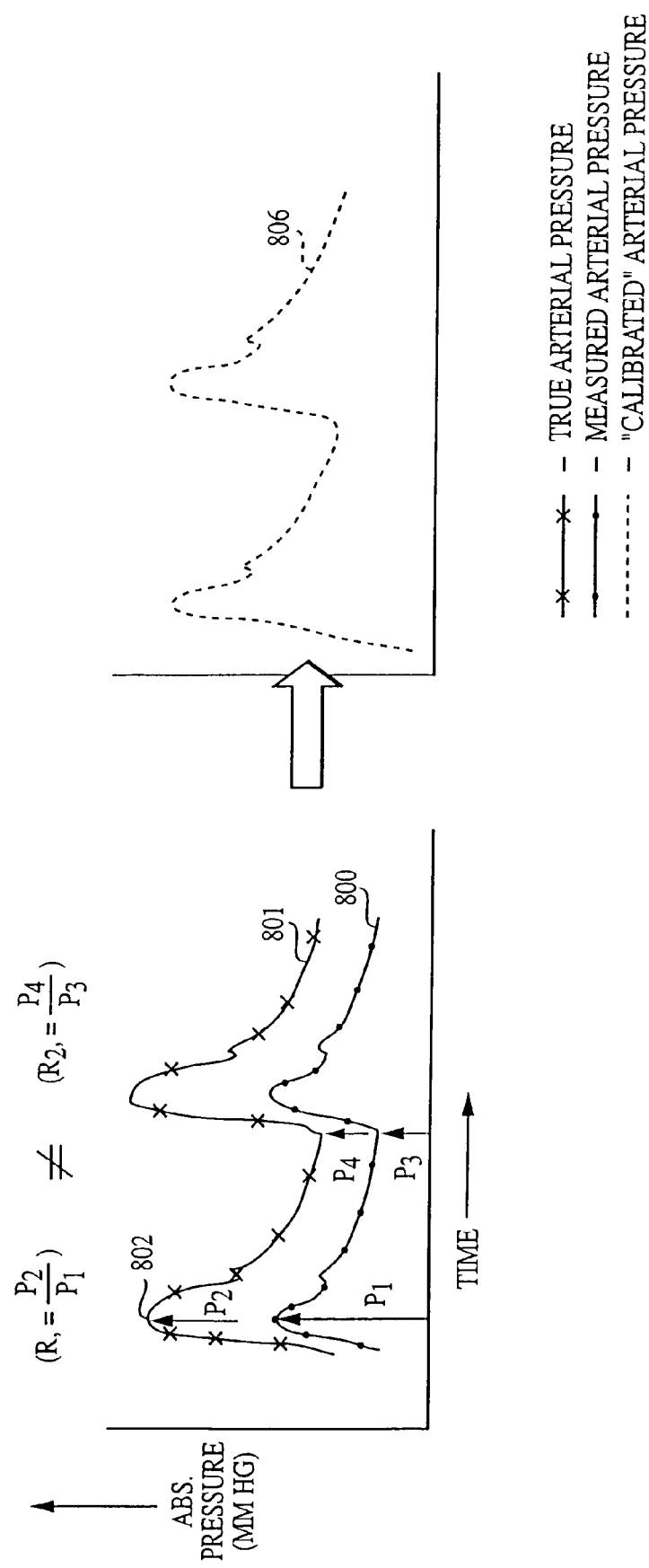
FIG. 8 is a graph of measured, actual, and scaled (calibrated) arterial pressure versus time for a typical human subject utilizing the invention.

In sum, the method 350 of FIG. 3d involves determining a transfer function/fraction as related to applied stress (e.g., pressure) for the subject and location being monitored, and calibrating the measured parameter at the designated "marker" point using the transfer function/fraction to determine the actual value of the parameter. In the case of blood pressure monitoring, this process involves applying an applanation pressure at which the kinetic energy term begins to increase (or alternatively, the maximum blood velocity begins to increase, the flow area begins to decrease, or some other desired condition is observed), and then correcting the measured value of the measured pressure using the transfer fraction to determine the actual intra-arterial pressure. When considered over the entire cardiac cycle, this method 350 produces a scaling or "stretching" function which is applied to the entire measured pressure waveform 800 to calibrate it to the true intra-arterial pressure 801, and thereby produce a "calibrated" waveform 806 as shown in FIG. 8. It is noted that depending on the portion of the measured pressure waveform being considered (e.g., diastolic portion, systolic portion, or there between), the ratio of actual or A-line intra-arterial pressure to the measured pressure will vary. This concept is graphically illustrated in FIG. 8, wherein the ratio of amplitudes at the systolic portion of the cardiac cycle $R_1$ 802 is not equal to the ratio of amplitudes at the diastolic portion $R_2$ 804.

It should be noted that while certain circumstances and individual subjects require the determination and application of a transfer function as described with respect to FIG. 3d, the general methodology of the invention may potentially be applied in some cases without a transfer function. For example, where a subject has a high degree of coupling between the skin and artery wall, the error associated with the pressure measured via the transducer placed at the skin surface may only constitute a small fraction of the total measurement, and would therefore be acceptable in certain monitoring environments. Hence, calculation and application of the transfer function is not a requirement of the present invention under all circumstances.

Figure 3E:
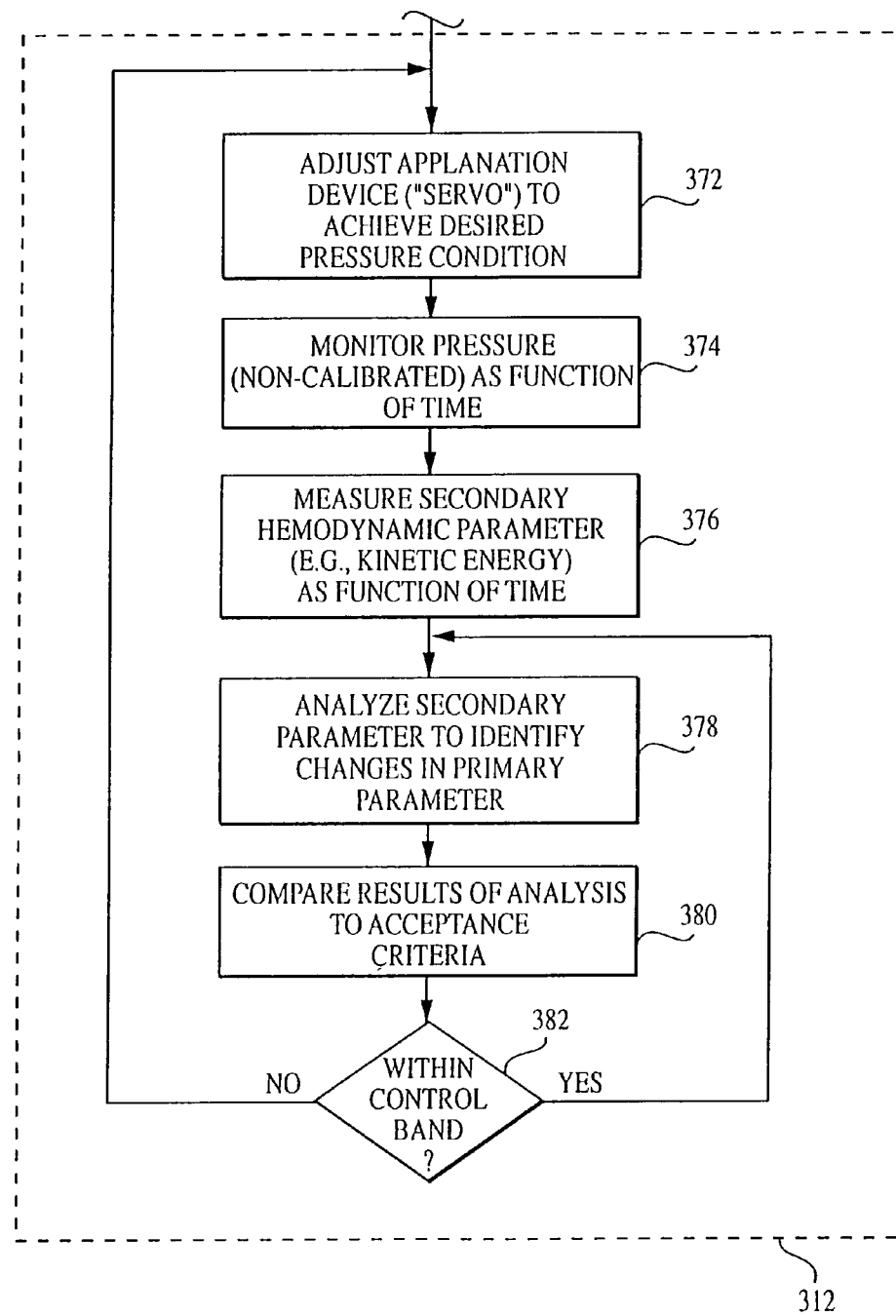

Referring now to FIG. 3e, the method of continuously calibrating the hemodynamic parameter being measured is described. As discussed with reference to FIG. 3d above, the transfer function is useful for correcting the measured pressure waveform for compression of the interposed tissue, artery wall, etc. This transfer function is obtained during an applanation sweep performed at a given monitoring location on the subject, such as the radial artery. However, to permit continuous monitoring of the subject's arterial blood pressure, a mechanism is needed whereby changes in the measured parameter can be accurately observed and scaled between calibration events (e.g., applanation sweeps).

As previously discussed, prior art calibration approaches relied on periodic calibration events (such as asculatory cuff measurements) to "continuously" calibrate the measured pressure waveform. The term "continuously" used with reference to these systems is somewhat of a misnomer, since what actually occurs is periodic (rather than continuous) updates of the scaling function. This approach presents at least one serious defect, that being the lack of calibration during the interval between periodic calibration updates. Depending on the activities of the subject being monitored, their true arterial blood pressure may vary significantly in a short period of time, and in some cases in a rapid or prompt fashion. For example, during surgery, actions by the surgeon such as artery re-section may have profound effects on the circulatory system of the subject, including their arterial blood pressure. Similarly, the difference between pre-induction (i.e., pre-anesthesia) and post-induction blood pressure values may be dramatically different, due in large part to the change of compliance within many of the arteries in the subject's body resulting from the anesthetic.

Since the prior art approaches in no way monitor the actual hemodynamic properties occurring within the artery, if such significant changes in true arterial blood pressure occur between periodic calibration events, they in many cases will go undetected. Rather, such prior art approaches typically monitor blood pressure tonometrically, these measurements being potentially very different from true arterial pressure. The prior art systems typically adjust the scaling factor or calibration to account for the measured change in tonometric blood pressure (which may or may not be close to true blood pressure). The result of this method is to produce so-called "calibrated" blood pressure values which in fact are not calibrated, but comprise a widely varying scaling component. This failure to track actual or true arterial blood pressure between calibration events can be catastrophic in cases where minute-to-minute measurements of blood pressure may be critical, such as during surgery.

The methodology of the present invention overcomes the foregoing significant limitations of the prior art by using the measured "secondary" hemodynamic parameter previously described to track changes in the first or "primary" measured hemodynamic parameter (e.g., blood pressure), as described in detail below.

In one embodiment, the kinetic energy of the blood is monitored using the aforementioned acoustic (or other) techniques while the zero transmural pressure state (or some other state determined to be of significance) is maintained within the artery, as illustrated by the method 370 of FIG. 3e. Specifically, the applanation device, which in the embodiment described below with respect to FIG. 12 also comprises the pressure and ultrasonic transducers, is "servoed" or continually modulated against the skin above the monitored artery in step 372 so as to maintain the desired pressure condition. The measured (non-calibrated) primary parameter, here pressure, is monitored as a function of time at the same time per step 374. Depending on the particular application, the modulation of step 372 may be controlled so as to maintain the transmural pressure at a specific value during the diastolic portion of the cardiac cycle, or alternatively during the systolic portion of the cycle. As yet another alternative, the applanation device may be modulated or servoed to maintain the mean transmural pressure (calculated over one or more complete cardiac cycles) at a predetermined value. Servoing may also be conducted to maintain a desired maximal blood velocity condition, or cross-sectional area condition. Many other such "target" servo values may be substituted with equal success, and the choice of such values, as well as the parametric relationship on which this value is based (e.g., the region on the maximum velocity v. flow area plots of FIG. 5d in which it is desired to operate) is solely determined by the needs of the user and the particular application in which the method is employed.

Next, in step 376, the secondary hemodynamic parameter is measured as a function of time using a suitable technique. In the present embodiment, the total kinetic energy (or maximum blood velocity) is measured using an acoustic Doppler system of the type previously described.

In step 378, the value of the secondary parameter measured in step 376 is analyzed to identify changes in the primary parameter. For example, when the applanation device is servoed to maintain zero transmural pressure in the diastolic portion of the cardiac cycle, changes in kinetic energy are used to track changes in intra-arterial blood pressure. The results of this analysis are compared to predetermined acceptance or control criteria per step 380 to determine if further adjustment of the applanation device is required (step 382).

For example, if significant increases or rates of increase in total blood flow kinetic energy were observed in steps 378-382 (thereby indicating that the applanation pressure felt by the artery wall was exceeding the true intra-arterial pressure), then the applanation pressure could be reduced so as to maintain the artery at a near-zero transmural pressure condition, as reflected by smaller increases or rates of increase in kinetic energy. It will be recognized that any type of control scheme which controls one parameter based on measurements of one or more other parameters may be used to effect the desired behavior, including fuzzy logic or PID controllers of the type well known in the control system arts.

Notwithstanding the foregoing, it will be recognized that the continuous calibration of the first hemodynamic parameter using the method of FIG. 3e may be accomplished using additional or other secondary parameters including, for example, maximal blood velocity and/or arterial cross-sectional (flow) area.

It is also again noted that in contrast to prior art approaches, the techniques of FIGS. 3-3e discussed above advantageously involve no modeling or estimation of parameters within the circulatory system of the subject being monitored; all information is derived via direct measurement of the subject at the selected monitoring location, and therefore is particularly adapted to that individual and that location.

Method of Characterizing Hemodynamic Response of Circulatory System

Figure 9:
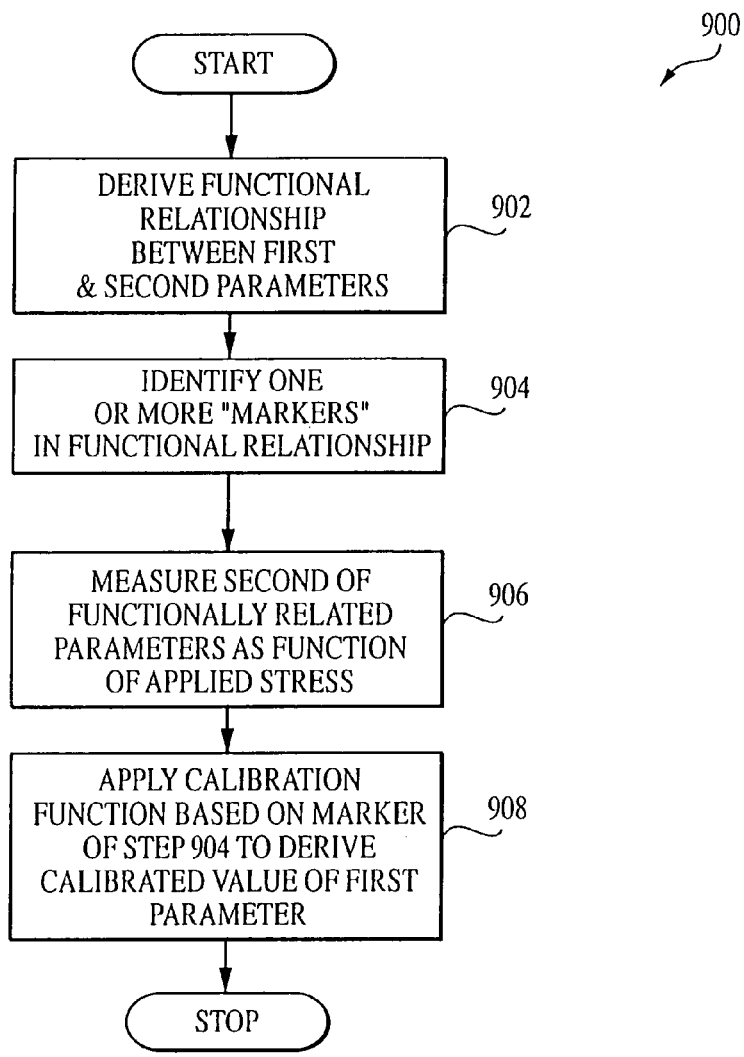
FIG. 9 is a logical flow diagram illustrating one exemplary embodiment of the method of modeling the hemodynamic response of the circulatory system of a living subject according to the invention.

Referring now to FIG. 9 a method of characterizing the hemodynamic response of the circulatory system of a living subject is disclosed. As illustrated in FIG. 9, the first step 902 of the method 900 comprises deriving a first functional relationship between first and second parameters associated with a blood vessel in relation to an applied stress. In the context of arterial blood pressure measurement, the first functional relationship derived in step 902 comprises the relationship(s) between arterial cross-sectional area (applanation pressure) and total blood flow kinetic energy as previously described herein, although it will be recognized that any number of different functional relationships may be substituted therefor. For example, the functional relationship between maximal blood velocity and flow area, velocity gradient and flow area, or volumetric blood flow (Q) and flow area, may be used if desired.

Next, in step 904, one or more artifacts or markers present within the functional relationship derived in step 902 above are identified. In the case of arterial blood pressure measurement as previously described, the artifact comprises the increasing kinetic energy or blood velocity after the condition of zero transmural pressure is achieved for the diastolic and/or systolic conditions. These artifacts comprise points for the calibration function previously described with respect to FIGS. 3c-3e herein. Alternatively, the points at which wall diameter begins to decrease at the systolic and diastolic portions of the cardiac cycle, as measured by A-mode ultrasound or other similar techniques, may constitute a marker of zero transmural pressure.

Next in step 906, one of the functionally related parameters from step 902 above is measured non-invasively as a function of the stress applied. In the above-referenced example, this measurement would comprise measuring blood velocity within the artery as a function of time (and applanation pressure), and deriving total flow kinetic energy therefrom.

Lastly, in step 908, the calibration "function" (which in theory may be as few as one data point) is applied to the measured response of a selected parameter associated with the circulatory system based on the artifact identified in step 904, thereby producing a calibrated characterization of the response of that parameter. For blood pressure, the selected parameter is tonometrically measured (i.e., non-calibrated) pressure, and the calibrated characterization comprises calibrated (or "true") arterial blood pressure determined at, inter alia, the point where the kinetic energy of the blood begins to increase.

Furthermore, the effects of potential errors (such as that due to incomplete signal transfer due to tissue compliance) may be accounted for as part of step 908 as well.

Method of Calibrating for Periodic Error Sources, Including Respiration

Figure 10:
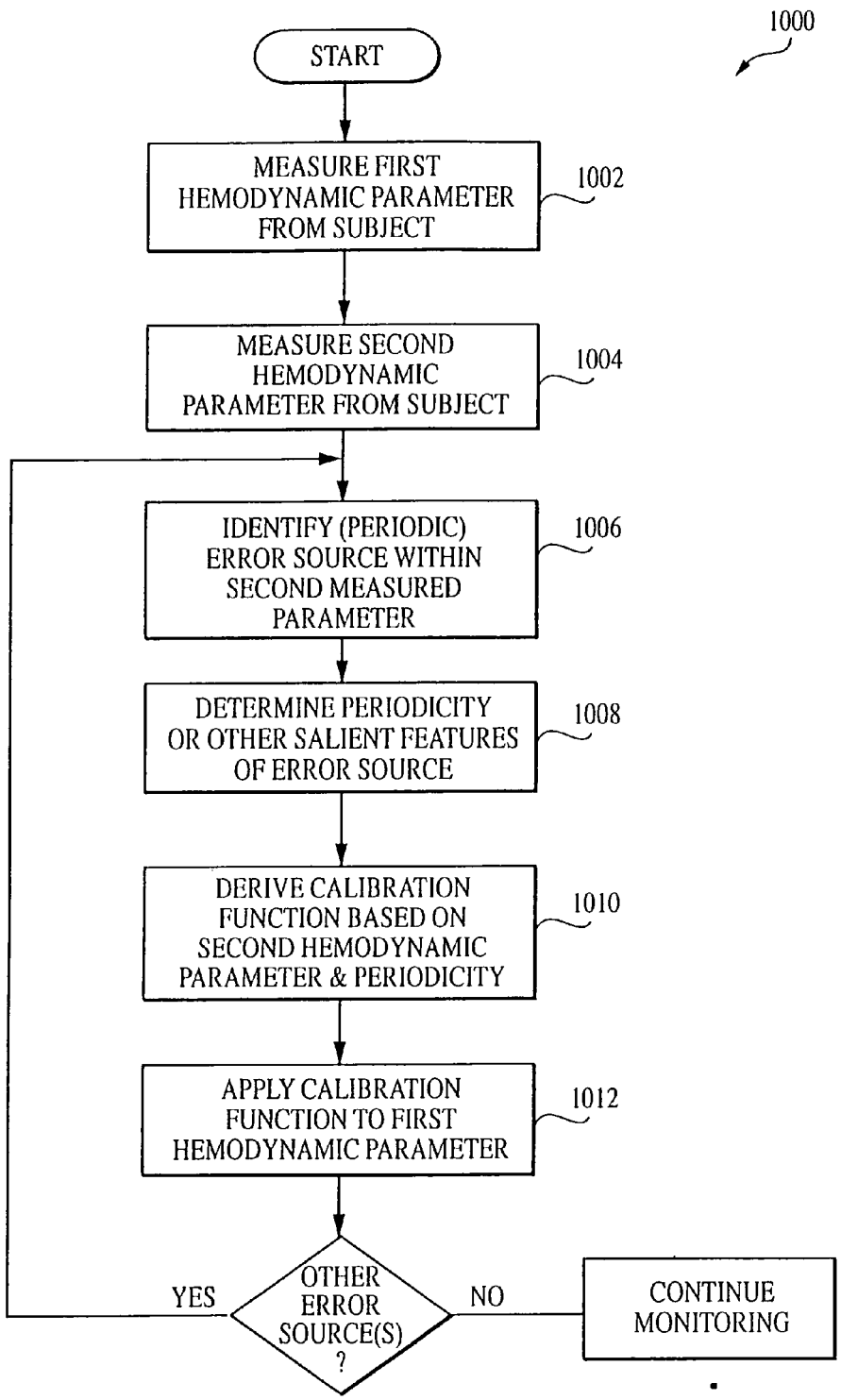
FIG. 10 is a logical flow diagram illustrating one exemplary embodiment of the method of calibrating a hemodynamic parametric measurement for respiration or other periodic error sources according to the invention.

Referring now to FIG. 10, a method of calibrating a hemodynamic parametric measurement for periodic error sources is disclosed. The first step 1002 of the method 1000 comprises measuring a first hemodynamic parameter associated with a blood vessel. As previously described, this parameter may comprise arterial blood pressure, or another parameter such as differential pressure, etc. In the case of arterial blood pressure, this parameter is the non-calibrated pressure waveform measured using the tonometric pressure transducer.

Next, in step 1004, a second hemodynamic parameter is measured on the subject, as previously described. This second hemodynamic parameter may comprise kinetic energy, maximum blood velocity, arterial diameter, flow area, etc. In one embodiment, the kinetic energy is calculated based on measurements of blood velocity made using Doppler ultrasound.

Figure 11:
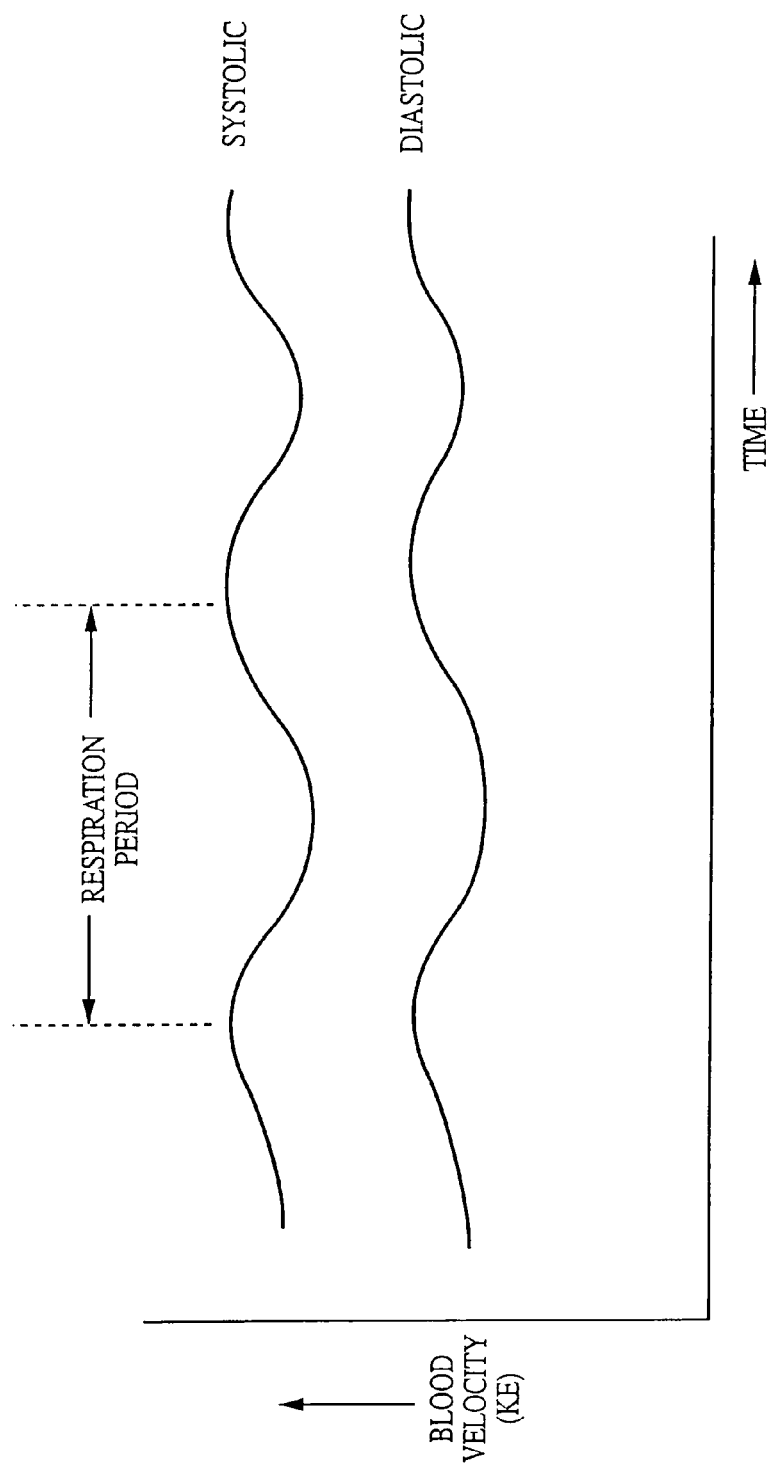
FIG. 11 is plot of the velocity and kinetic energy (KE) of blood flowing within a typical blood vessel, illustrating the effects of respiration thereon.

Next, in step 1006, periodic error sources associated with the first parameter are identified within the second parameter. In one exemplary case, the periodic error source relates to the respiration of the subject being monitored, illustrated in FIG. 11. As shown in FIG. 11, the velocity and kinetic energy of the blood flowing within the radial artery of a human being generally includes a time-variant, periodic component. This periodic behavior is due in substantial part to the respiration cycle of the subject, and occurs at much lower frequency than the typical cardiac cycle. Hence, the normal cardiac cycle 1102 can be thought to be "amplitude modulated" by the periodic respiratory variance 1104.

The origin of the respiratory periodic variance relates to the varying pressures which occurs as the diaphragm ascends and descends. With inspiration, the diaphragm should descend, increasing intra-abdominal pressure and decreasing intra-thoracic pressure. The increase in the pressure differential from the abdomen to the right atrium increases the volumetric flow back to the right atrium. With expiration, as the diaphragm ascends, the intra-abdominal pressure decreases and the intra-thoracic pressure increases. The result is more venous return to the abdomen from the lower extremities, but less return to the right atrium. The cyclical changes in volume and pressure are reflected everywhere throughout the circulatory system, since it is a closed system.

The aforementioned cyclical respiratory changes result in variant flow velocities and kinetic energies for, inter alia, the measured diastolic and systolic pressures. In a normal adult human being, anecdotal evidence obtained by the Applicant herein suggests that the magnitude of such variations may be on the order of 20 mm Hg or more in severe cases. Taken as a fraction or percentage of the systolic and diastolic pressures, this variation in pressure due to respiration may be significant, especially for the lower diastolic pressures measured when the subject is not ambulatory, such as during surgery.

These variations are accounted for in the present invention, when required, by synchronizing the derivation of the calibration function from the measurement of the secondary hemodynamic parameter (e.g., velocity, kinetic energy, or area). Specifically, in step 1008 of the method 1000, the periodicity of the respiratory variation is analyzed and determined, and this information is used to synchronize the derivation of the calibration function to a common point on the period ("carrier") respiration waveform. Identification of the respiratory component and its periodicity is accomplished using any one of a number of algorithms well known in the signal processing arts; accordingly, such algorithms will not be discussed further herein. It is noted that since the respiratory rate and/or "depth" of respiration of the subject may vary with time, thereby affecting the periodicity and magnitude of pressure/flow variations within the artery, the periodicity of the respiratory effect should be continually (or at least frequently) calculated.

Next, in step 1010, a calibration function is developed based on measurements of the secondary hemodynamic parameter taken at the periodicity prescribed by the result of step 1008. For example, a series of blood velocity measurements may be taken every 7 seconds (each measurement corresponding to the same relative point on the respiration waveform, but displaced in time), and this information used to derive kinetic energy values and a calibration or "stretching" function as described previously herein with reference to FIGS. 3-3*e*.

Lastly, in step 1012, the stretching function of step 1010 is applied to the measured (i.e., non-calibrated) waveform of step 1002. Note that by virtue of measuring the second hemodynamic parameter at a similar point relative to the respiration waveform, the effects of respiration across the entire respiration cycle are accounted for. Hence, the derived stretching function may be applied to the entire non-calibrated pressure waveform), as opposed to only those portions of the waveform corresponding to the points in time when the second parameter was actually measured. Assuming the pressure transfer to be relatively linear around the systolic pressure variations with respiration, and the diastolic pressure variations with respiration, no other correction would be necessary. An additional correction can be applied if the non-linearities are significant enough, by calculating the correction factors at a different phase of the respiration cycle. This represents a significant advantage in providing a continuously (as opposed to periodically) calibrated representation of true arterial blood pressure.

It will be appreciated that while the foregoing discussion is cast in terms of periodic error due to respiratory system effects, other types of errors, periodic or aperiodic, may be accounted for using the methodology of the present invention as illustrated in FIG. 10. For example, the effects of an arrhythmia within the heart of the subject may be identified and accounted for during derivation of the calibration function. An arrhythmia within the heart of the subject may be identified using signal processing algorithms specifically adapted for the purpose of identifying aperiodic components within waveforms, such algorithms being well known to those of ordinary skill in the signal processing arts. Numerous other types on non-periodic error components may also be identified in conjunction with the method of FIG. 10.

Apparatus for Hemodynamic Assessment

Figure 12:
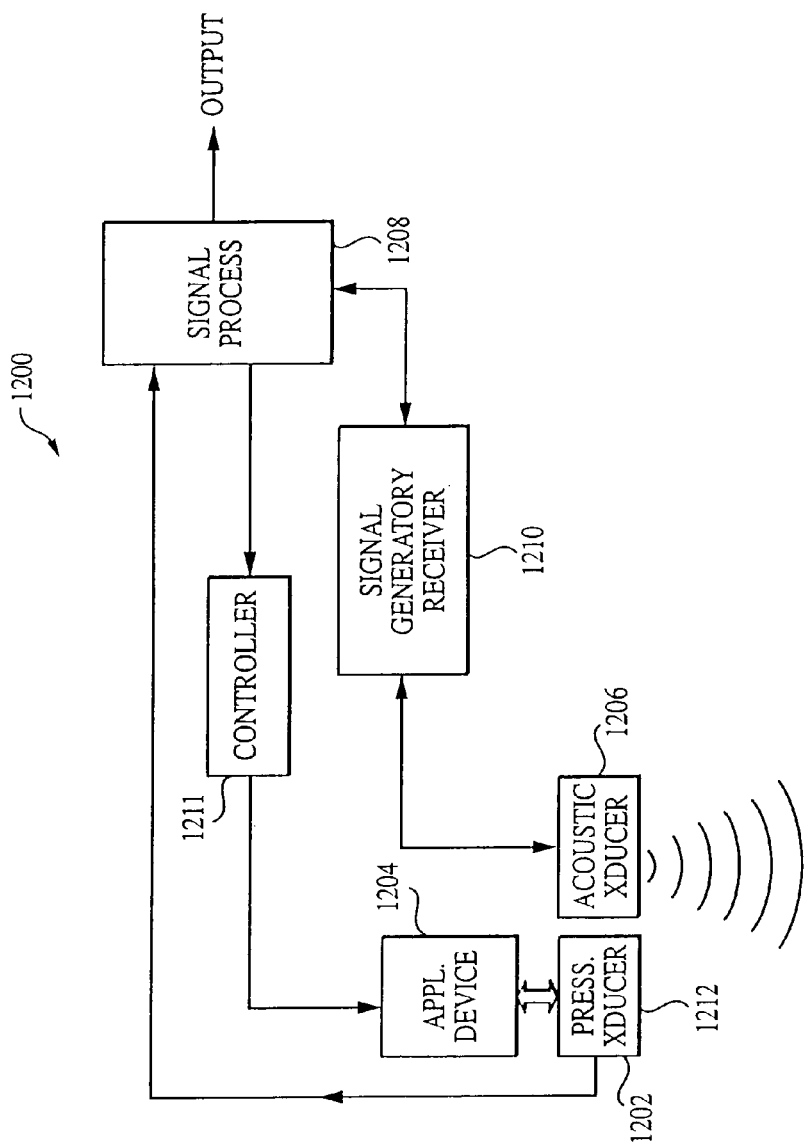
FIG. 12 is a block diagram of one exemplary embodiment of the apparatus for measuring hemodynamic properties within the blood vessel of a living subject according to the invention.

Referring now to FIG. 12, an apparatus for measuring hemodynamic properties within the blood vessel of a living subject is described. In the illustrated embodiment, the apparatus is adapted for the measurement of blood pressure within the radial artery of a human being, although it will be recognized that other hemodynamic parameters, monitoring sites, and even types of living organism may be utilized in conjunction with the invention in its broadest sense. The apparatus 1200 of FIG. 12 fundamentally comprises a pressure transducer 1202 for measuring blood pressure from the radial artery tonometrically; an applanation device 1204 coupled to the transducer 1202 for varying the degree of applanation (compression) on the artery; an acoustic transducer 1206 for generating acoustic emissions and reflections thereof, these acoustic emissions being used to derive blood velocity (and kinetic energy); a signal processor 1208 operatively connected to the pressure and acoustic transducers 1202, 1206 for analyzing the signals generated by these transducers and generating a calibration function based thereon; a signal generator/receiver 1210 used to generate acoustic signals for transmission into the artery, and receive signals from the acoustic transducer 1206; and a controller 1211 operatively coupled to the applanation device 1204 and the signal processor 1208 for controlling the degree of applanation pressure applied to the artery.

The pressure transducer 1202 is, in the present embodiment, a silicon strain gauge or piezoelectric transducer element which generates an electrical signal in functional relationship (e.g., proportional) to the pressure applied to its sensing surface 1212. Similarly, the acoustic transducer 1206 comprises a silicon strain gauge or piezoelectric (ceramic) device which is capable of both generating and receiving acoustic waves and/or pulses depending on mode. In the illustrated embodiment, the acoustic transducer 1206 is tuned to generate ultrasonic frequencies centered at 8 MHz, although other center frequencies, with varying bandwidths, may be used. The signal generator/receiver 1210 generates electrical signals or pulses which are provided to the acoustic transducer 1206 and converted into acoustic energy radiated into the blood vessel. This acoustic energy is reflected by various structures within the artery, including blood flowing therein, as well as tissue and other bodily components in proximity to the artery. These acoustic reflections (echoes) are received by the acoustic transducer 1206 and converted into electrical signals which are then converted by the signal generator/receiver 1210 to a digital form (using, e.g., an ADC) and sent to the signal processor 1208 for analysis. Depending on the type of acoustic analysis technique and mode employed, the signal processor 1208 utilizes its program (either embedded or stored in an external storage device) to analyze the received signals. For example, if the system is used to measure the maximum blood velocity, then the received echoes are analyzed for, inter alia, Doppler frequency shift. Alternatively, if the arterial diameter (area) is measured, then an analysis appropriate to the aforementioned A-mode is employed.

During a calibration "sweep", the controller 1211 controls the applanation device to applanate the artery (and interposed tissue) according to a predetermined profile. During this sweep, acoustic signals are transmitted into and received from the artery preferably in a region directly proximate the ongoing applanation of the tissue. Velocity, kinetic energy, and/or arterial diameter data is extracted and/or derived from the received echoes and recorded as a function of the applanation pressure for the selected portion(s) of the cardiac cycle. The signal processor 1208 and associated algorithms then identify one or more markers, and determine the desired applied pressure at which continuous monitoring is to occur based on the measured markers. For example, if the peak in maximum velocity shown in FIG. 4*b* were selected as the marker, the algorithms would identify this peak and identify the pressure data corresponding to this peak. During subsequent blood pressure monitoring, the controller 1211 would servo the position of the applanation device 1204 (in the present embodiment, the pressure transducer 1202) so as to maintain the target pressure, or any other value selected by the programmer/user. Subsequent changes in the measured parameter (e.g., total blood flow kinetic energy) are used to identify changes in the actual blood pressure within the artery, thereby obviating the need for a continuing series of calibration sweeps.

Optionally, the apparatus 1200 is also configured to measure the transfer function of the tissue and other bodily components interposed between the signal source and the sensor. As described with respect to FIG. 7 above, there is an incomplete or fractional transfer of energy between the blood within the artery and the pressure sensor. To address this issue, the apparatus 1200 of FIG. 12 includes a transfer function algorithm (not shown) which utilizes data obtained from A-mode analysis or other techniques relating to the relative compression of the arterial diameter and the proximate body components when applanated. Hence, during a calibration sweep, the apparatus 1200 stores A-mode or other comparable data which is used by the transfer function algorithm to determine the relative compression of the artery and components as a function of varying applanation pressure. The transfer function (e.g., change in arterial diameter as a function of applanation pressure) is generated by the algorithm and stored in any number of different ways, such as a look-up table or a mathematical function. Subsequent to the calibration sweep, as the apparatus 1200 servoes to the desired applied pressure derived from the identified marker, a correction is imposed on the measured pressure based on the transfer function. For example, if the system is servoing to a diastolic pressure of 60 mm Hg as measured by the pressure transducer 1202, the true value of the pressure in the artery will be corrected according to the transfer function to a value somewhat higher than 60 mm Hg.

Figure 13:
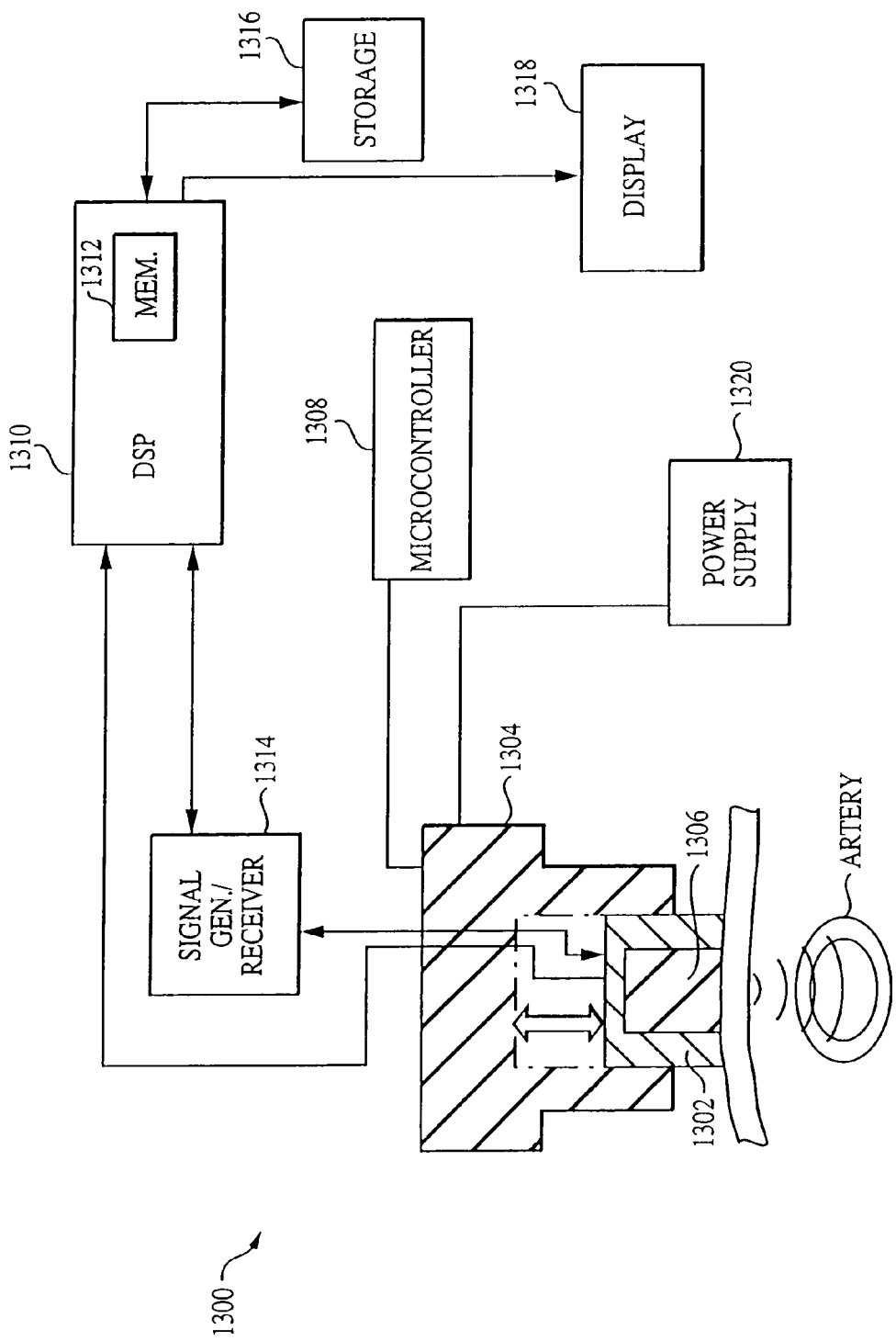
FIG. 13 is a functional block diagram of a second embodiment of the apparatus of FIG. 12 illustrating its use on the radial artery of a human being.

Referring now to FIG. 13, one specific embodiment of the apparatus for assessing hemodynamic parameters of FIG. 12 is described. In the embodiment of FIG. 13, the apparatus 1300 comprises a self-contained unit having, inter alia, a combined pressure transducer 1302 and applanation device 1304, acoustic transducer 1306, microcontroller 1308 with control micro-code (such as a fuzzy logic algorithm), digital signal processor (DSP) 1310 with embedded memory 1312 and instruction set (including calibration lookup tables), signal generator and receiver unit 1314, storage device 1316, display device 1318, and power supply 1320. In this embodiment, the microcontroller 1308 is used to control the operation of the combined pressure transducer 1302/applanation device 1304 so that an initial applanation "sweep" is performed. Specifically, the pressure transducer 1302 is placed in communication with the skin of the interior of the wrist of the subject, over the radial artery, and fastened in place as illustrated in FIG. 13. Measurement of the non-calibrated blood pressure from the radial artery is commenced, and shortly thereafter the microcontroller 1308 directs the applanation mechanism 1304 to press the transducer 1304 against the wrist of the subject with increasing pressure, thereby applanating the underlying artery. As the artery is applanated, the acoustic transducer 1306 is also pressed in communication with the skin over the artery, and the signal generator 1314 generates a series of acoustic pulses which are transmitted through the skin into the artery. As applanation of the artery continues, the signal generator/receiver unit 1314 receives echoes from the blood and other components within the artery via the acoustic transducer 1306, and generates an output signal relating to the received echoes. This output signal is processed and then digitized for subsequent analysis by the DSP or similar processing engine. Similarly, the output signal of the pressure transducer 1302 is digitized and input to the DSP. The digitized signals are then analyzed using the embedded program within the DSP, which is a machine code representation of the computer program described subsequently herein. The output of the digital signal processor is a corrected pressure waveform which is then supplied to the display device 1318 (whether in digital or analog form, depending on the type of device used) for display to the user. Optionally, the output of the DSP may be stored in one or more storage locations within the storage device 1316, and/or output to an external device.

It is noted that the apparatus 1200, 1300 described herein may be constructed in a variety of different configurations, using a variety of different components, and measuring a variety of different hemodynamic parameters. Exemplary control, signal generation/processing, and applanation mechanisms and circuitry are described in Assignee's co-pending U.S. patent application Ser. No. 09/342,549, entitled "Method And Apparatus For The Noninvasive Determination Of Arterial Blood Pressure," previously incorporated herein.

Computer Program and Related Apparatus

Figure 14B:
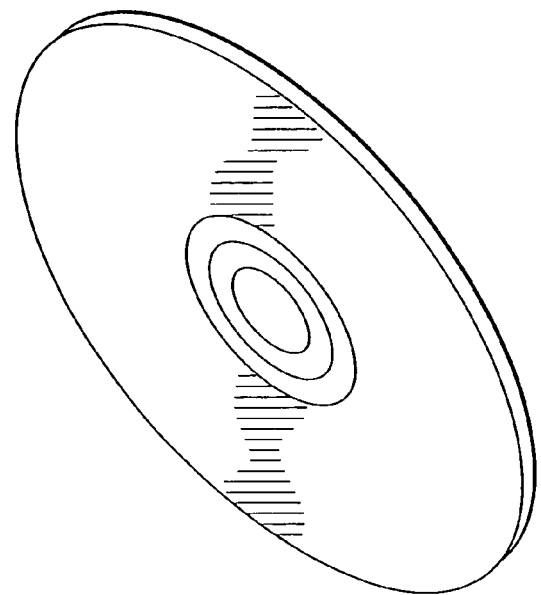
FIGS. 14a-14b are perspective views of various machine readable media having object code representations of computer programs incorporating the methods of the present invention.
Figure 14A:
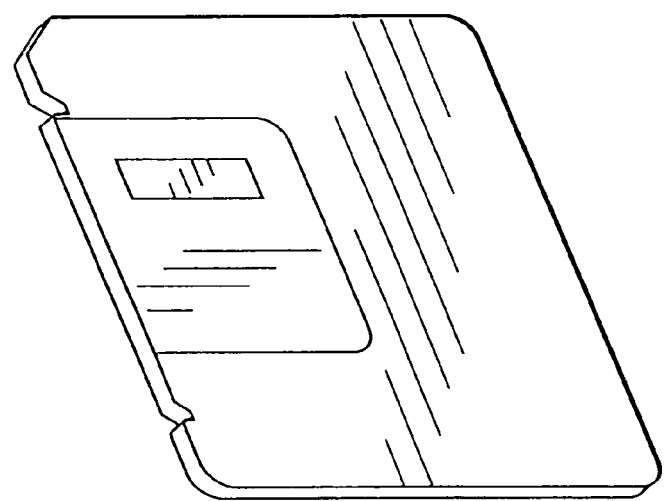

A computer program for implementing the aforementioned methods of hemodynamic assessment, modeling, and calibration is now described. In one exemplary embodiment, the computer program comprises an object ("machine") code representation of a C++ source code listing implementing the methodology of FIGS. 3-3e, 9, and 10, either individually or in combination thereof. While C++ language is used for the present embodiment, it will be appreciated that other programming languages may be used, including for example VisualBasic™, Fortran, and C+. The object code representation of the source code listing is compiled and disposed on a media storage device of the type well known in the computer arts, as illustrated in FIGS. 14a-b. Such media storage devices can include, without limitation, optical discs, CD ROMs, magnetic floppy disks or "hard" drives, tape drives, or even magnetic bubble memory. The computer program further comprises a graphical user interface (GUI) of the type well known in the programming arts, which is operatively coupled to the display and input device of the host computer or apparatus on which the program is run (described below with respect to FIG. 15).

In terms of general structure, the program is in one embodiment comprised of a series of subroutines or algorithms for implementing the hemodynamic assessment, modeling, and calibration methodology described herein based on measured parametric data provided to the host computer. In a second embodiment, the computer program comprises an assembly language/micro-coded instruction set disposed within the embedded storage device, i.e. program memory, of a digital signal processor (DSP) or microprocessor associated with the foregoing hemodynamic measurement apparatus of FIG. 12 or 13.

Figure 15:
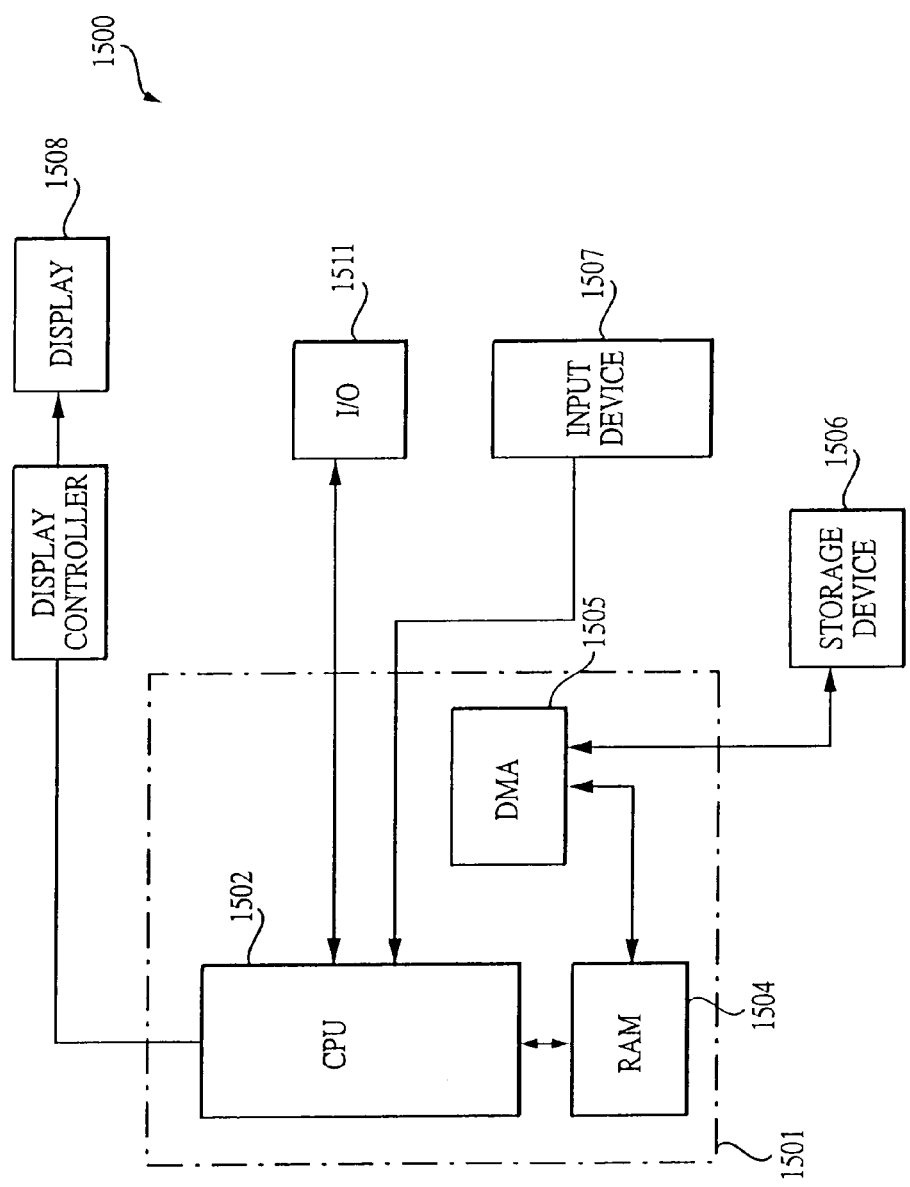
FIG. 15 is a block diagram of a first embodiment of the apparatus for analyzing parametric data according to the invention.

Referring now to FIG. 15, one embodiment of an apparatus capable of analyzing parametric data and generating calibrated values of hemodynamic parameters as disclosed herein is described. The computing device 1500 comprises a motherboard 1501 having a central processing unit (CPU) 1502, random access memory (RAM) 1504, and memory controller (such as a direct memory access controller) 1505. A storage device 1506 (such as a hard disk drive or CD-ROM), input device 1507 (such as a keyboard or mouse), and display device 1508 (such as a CRT, plasma, or TFT display), as well as buses necessary to support the operation of the host and peripheral components, are also provided. A serial or parallel I/O port 1511 is also included for the transfer of data and/or control signals to and from the apparatus 1500.

The aforementioned computer program useful for assessing hemodynamic parameters is stored in the form of a machine-readable object code representation in the RAM 1504 and/or storage device 1506 for use by the CPU 1502 during parametric assessment. The user (not shown) assesses the hemodynamic parameters of interest by selecting one or more functional modes for the computer program and associated measuring equipment via the program displays and the input device 1507 during system operation. Specifically, in the case of arterial blood pressure measurement, the user places the necessary parametric sensors on the selected blood vessel of the subject, and configures the computer program to accept data output by the sensors either continuously or at a predetermined interval. The computer program performs the previously described analysis if the signals provided to the apparatus 1500, and generates a calibrated signal to be displayed on a display device, or on the systems own display device. A look-up table or similar mechanism is stored within the computer memory or storage device to facilitate calibration, as previously described with respect to FIG. 12, Such calibrated measurements generated by the program are also optionally stored in the storage device 1506 for later retrieval, or output to an external device such as a printer, data storage unit, other peripheral component via a serial or parallel port 1512 if desired. Furthermore, the apparatus 1500 may be networked to another computing device or database via network interface card (NIC) or similar interface (not shown) whereby the data generated by the apparatus 1600 may be remotely analyzed or stored. Transmission to such remote devices may be accomplished using a variety of well understood methods, such as by local area network (LAN), intranet, Internet, fiber-optic systems, or radio frequency (wireless) devices.

In yet another embodiment, the apparatus comprises a personal computing device (such as a personal digital assistant, or PDA), which is adapted to receive input data from the pressure and acoustic sensors and analyze the data to produce a corrected measurement of blood pressure. It will also be recognized that other portable devices, such as laptop computers, calculators, and personal organizers, may be configured to run the computer program of the present invention. Furthermore, a variety of different methods of transmitting the input sensor data to these device may be used, including networked computers, or even wireless data links.

Method of Providing Treatment

Figure 16:
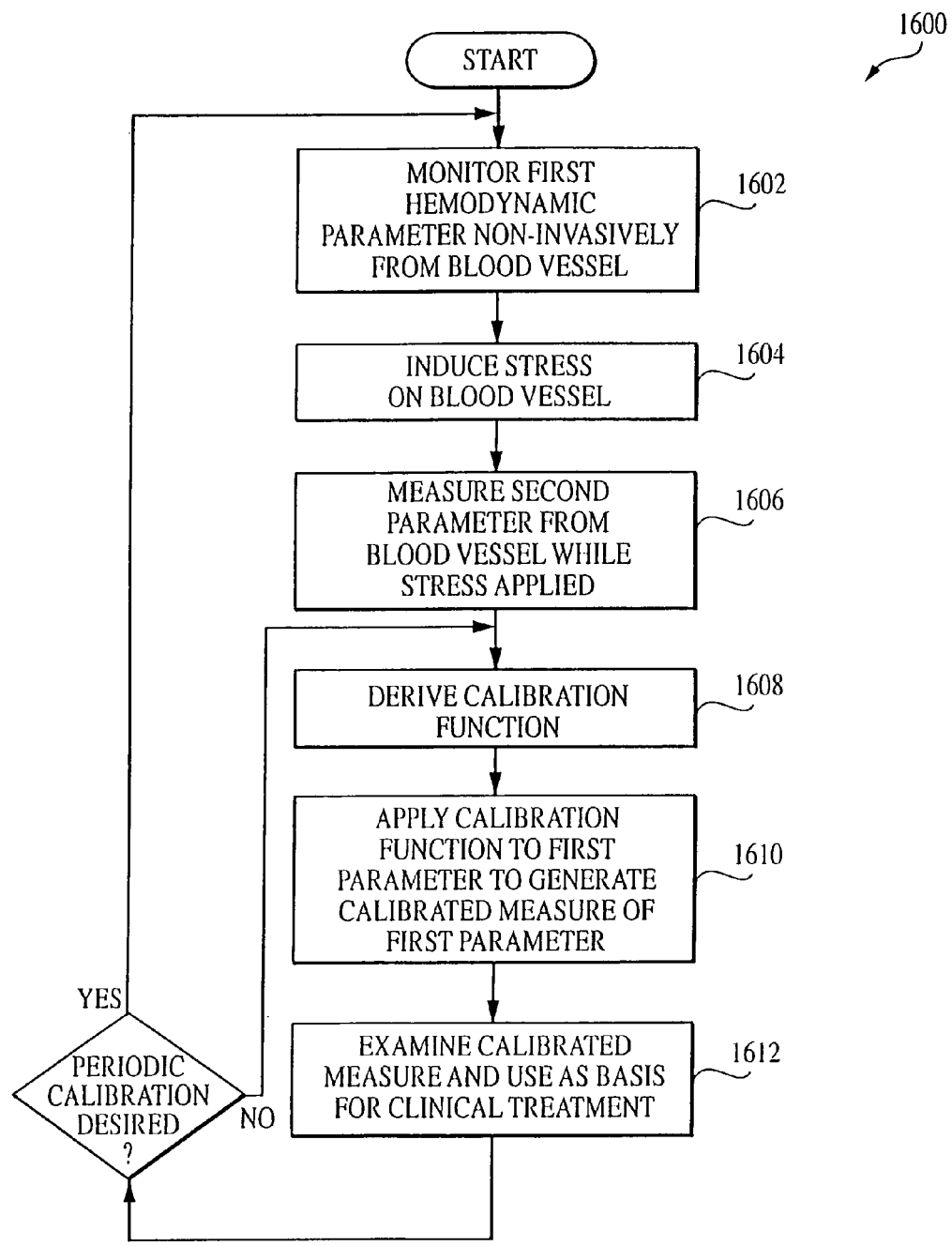
FIG. 16 is a logical flow diagram illustrating one exemplary embodiment of the method of providing treatment to a subject using the aforementioned methods.

Referring now to FIG. 16, a method of providing treatment to a subject using the aforementioned method of assessing hemodynamic parameters is disclosed. As illustrated in FIG. 16, the first step 1602 of the method 1600 comprises monitoring an non-calibrated hemodynamic parameter non-invasively. In the case of blood pressure, an exemplary pressure transducer applied to the radial artery is used as described with respect to FIG. 3a herein.

Next, in step 1604 of FIG. 16, a stress is induced on the blood vessel which alters its hemodynamic properties (at least locally), thereby inducing changes in other parameters associated with the vessel or circulatory system as a whole. As previously discussed with respect to FIG. 3b herein, this stress comprises in one embodiment applanating or variably compressing the blood vessel as a function of time, thereby inducing changes in, inter alia, the volumetric flow (Q), velocity (v), and kinetic energy (KE) of the blood in the region of the applanation. It is again noted, however, that other stressors may conceivably be applied which may affect similar or other hemodynamic properties.

Next, in step 1606, a second parameter associated with the blood vessel is measured in order to facilitate derivation of a calibration function in step 1608 below. As discussed with respect to FIG. 3c herein, the second parameter in one embodiment comprises total blood flow kinetic energy or maximum blood velocity since these parameter exhibits certain easily identified "artifacts" as a function of the application of the stressor in step 1604. Other parameters which exhibit the same or other artifacts may be used to derive the calibration function however.

In step 1608 of FIG. 16, a calibration metric or function is next derived based on the parametric information derived in step 1606. Specifically, one or more artifacts or markers are identified within the parametric data, these artifacts indicating when certain relationships between the actual and measured values of the first parameter of step 1602 above exist. As discussed with reference to FIGS. 3-3e herein, one embodiment of the process of deriving a calibration function comprises (i) measuring kinetic energy or maximum blood velocity profiles proximate to the area of the applied stressor (applanation), and identifying regions of increasing velocity or kinetic energy within these profiles as a function of the applanation (correlated to percentage reduction of cross-sectional area of the blood vessel); and (ii) measuring a transfer function for the tissue and other bodily components in the region of pressure measurement.

In step 1610 of the method of FIG. 16, the calibration function derived in step 1608 is applied to the measurement of the first parameter of step 1602 to generate a corrected or calibrated measurement. Note that if the first parameter is measured continuously (or periodically) as a function of time, the correction function of step 1608 may be continuously or periodically applied as appropriate, or alternatively the second hemodynamic parameter may be monitored (such as during pressure servoing as previously described) to indicate changes in the calibration function.

Lastly, in step 1612, the calibrated measurement of the first parameter is used as the basis for providing treatment to the subject. For example, in the case of blood pressure measurements, the calibrated systolic and diastolic blood pressure values are generated and displayed or otherwise provided to the health care provider in real time, such as during surgery. Alternatively, such calibrated measurements may be collected over an extended period of time and analyzed for long term trends in the condition or response of the circulatory system of the subject.

Alternate "Backscatter" Embodiment

As previously discussed, backscattered acoustic energy (such as "A-mode" ultrasonic energy) may be used to determine hemodynamic parameters including, for example arterial diameter and end diastolic blood pressure. As used herein, the term "A-mode" encompasses both traditional A-mode (i.e., display of amplitude versus depth (time) via repeatedly scanned lines) and other related modalities such as M-mode (i.e., grayscale image distributed over temporal dimension) and B-mode (i.e., "steered" grayscale image representative of depth (time) versus width), such alternate modalities being well known to those of ordinary skill in the ultrasound arts. Hence, it will be recognized that while the following discussion is cast in terms of traditional A-mode, the other associated modalities may be employed as well.

FIGS. 17-37 illustrate yet another embodiment of the method and apparatus for measuring hemodynamic parameters according to the present invention. This embodiment uses A-mode ultrasonic energy to determine arterial wall positions based on analysis of the resulting waveform of the reflected energy, the wall positions being used to aid in the identification of "markers" or artifacts within the sensed pressure waveform(s) which are correlated to blood pressure measurements. The A-mode ultrasonic energy of the present embodiment advantageously complements the Doppler spectral modalities previously described herein, but may also be used alone if desired, thereby providing both the system designer and ultimate end users of the apparatus with greatly enhanced flexibility in both design and operation. Specifically, at least three different operating schemes are contemplated by the present invention, including: (i) A-mode detection alone; (ii) Doppler-based detection alone; and (iii) a combination of the A-mode and Doppler modalities together. While not required, such use of complementary modalities as in (iii) advantageously enhances the reliability and robustness of results obtained with the instrument.

It has been observed by the Assignee hereof that as the blood vessel is increasingly compressed (applanated), various of such hemodynamic markers occur within the sensed pressure waveform. In one aspect, certain "flat spots" within the end diastolic portion of the waveform occur, wherein the change in sensed pressure as a function of time is low (or at least lower than surrounding portions of the waveform). These flat spots correlate to various phenomena within the tissue surrounding the blood vessel, and the blood vessel itself, including overcoming the hoop stress associated with the walls of the blood vessel. As previously referenced herein, the hoop stress associated with a substantially cylindrical hollow body such as the human radial artery acts as a retarding force to further compression. Stated differently, a finite force (or pressure, over a given area) must be applied to the outer surface of the blood vessel before the cross-section of the blood vessel begins to significantly deform; beyond this point of deformation, a proportionately small additional force is required to further deform the blood vessel. Hence, once overcome, the hoop stress component is effectively eliminated, thereby creating a state where pressure applied to the blood vessel wall externally can equilibrate with that applied by the pressurized lumen (e.g., blood) flowing within the blood vessel to maintain the cross-section of the vessel essentially constant (zero transmural pressure). This condition is significant in that once the hoop stress has been overcome, the intra-vessel pressure is in effect directly transmitted across the artery wall. The point along the applanation profile at which such flattening (i.e., zero transmural pressure) condition exists, however, will vary from individual to individual, and from species to species, and from location to location for a single individual. Therefore, additional techniques are required to accurately isolate the point on the pressure waveform where the desired transmural pressure condition exists.

One such technique (described in greater detail below) is to detect the front and rear walls of the blood vessel under evaluation, this information being used to directly determine the reduction in diameter of the blood vessel. As has been previously shown, the reduction of blood vessel diameter can be directly related to certain systolic and diastolic pressure conditions, and correlated to the occurrence of certain of the aforementioned hemodynamic markers.

Lumen and Wall Detection

The methodology of the present invention advantageously employs A-mode ultrasonic energy to detect the position of the lumen and the front and back walls of the blood vessel. As used herein, the terms "front" and "back" infer no specific spatial orientation, but simply refer to the order in which the walls of the blood vessel are encountered during direct propagation by a moving ultrasonic wavefront emanated from an ultrasonic source. Hence, what may be the "front" wall when measuring hemodynamic properties in one transducer orientation may comprise the "rear" wall in another transducer orientation. Unique to the present invention is also the use of lumen detection as a means of front and back wall detection; i.e., due to the comparatively lower backscatter of ultrasonic energy by the lumen as compared to other blood vessel components, the position of the lumen may be readily identified from the backscattered energy, and the front and rear vessel walls identified relative thereto.

Figure 17:
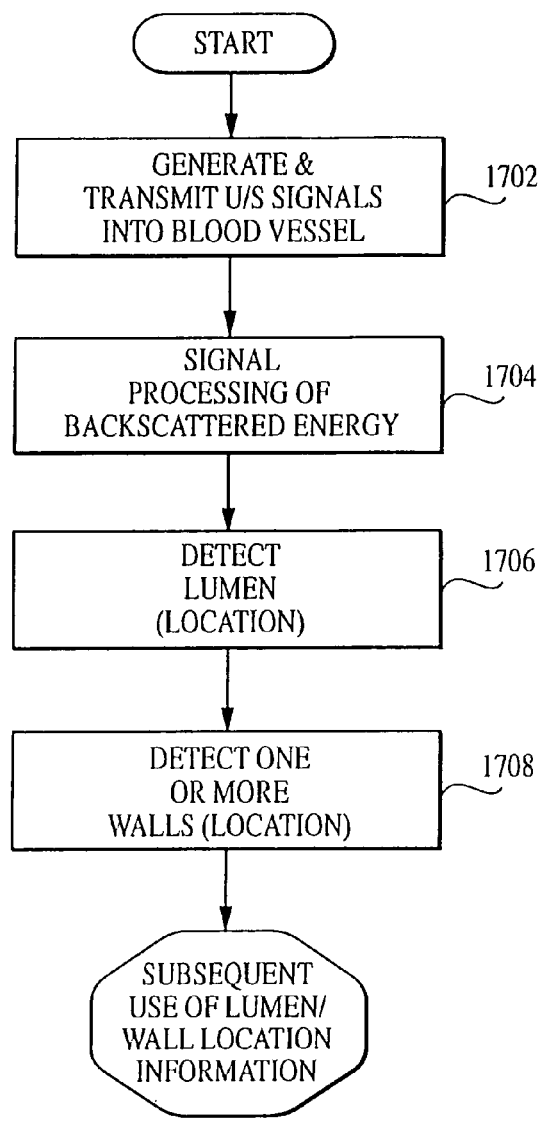
FIG. 17 is a logical block diagram illustrating one exemplary embodiment of the general method of lumen and wall detection according to the present invention.

FIG. 17 illustrates the general methodology of using backscattered ultrasonic energy for lumen and wall detection according to the invention. The ultrasonic energy is generated by the apparatus (e.g., the ultrasonic transducer 1206 of the system 1200 of FIG. 12) and transmitted directly through the subject's skin into the underlying tissue, and ultimately through the blood vessel of interest (step 1702). In the present context, the term "tissue" is meant to include all components present in the vicinity of the blood vessel being examined, including any interposed skin, musculature, tendons, veins, as well as the blood vessel (e.g., artery) wall and lumen itself. Signal processing is next performed on the received backscattered energy (step 1704) in order to aid in subsequent lumen and wall detection.

The processed signals are then analyzed per step 1706 to detect the location of the lumen therein. Specifically, the processed backscattered energy signals are analyzed to identify the occurrence of a backscattered energy "minimum" within a range of depths consistent with the depth of the blood vessel under consideration in the species/age range being evaluated. The position of this minimum is assumed to coincide with lumen existing within the blood vessel being evaluated.

One or both blood vessel walls are then detected in step 1708 using the lumen detected in step 1706 as a starting point for the analysis. The signals associated with the front and back blood vessel walls are detected by searching forward and backward from the identified location of the lumen within the artery. When the backscattered energy associated with the search in the backward direction (towards the transducer) satisfies one or more criteria, such as exceeding the mean lumen power or estimated level of the blood signal by a prescribed amount or factor (described below in greater detail), the front wall is detected and the location of the signal along the line is interpreted as the location of the front wall. Similarly, when the reflected energy associated with the search in the forward direction satisfies the relevant back wall criteria, the back wall is detected and the location of the signal along the line is interpreted as the location of the back wall. Various methodologies for wall detection are described in detail below with respect to FIGS. 29*a* and 29*b*.

Figure 17A:
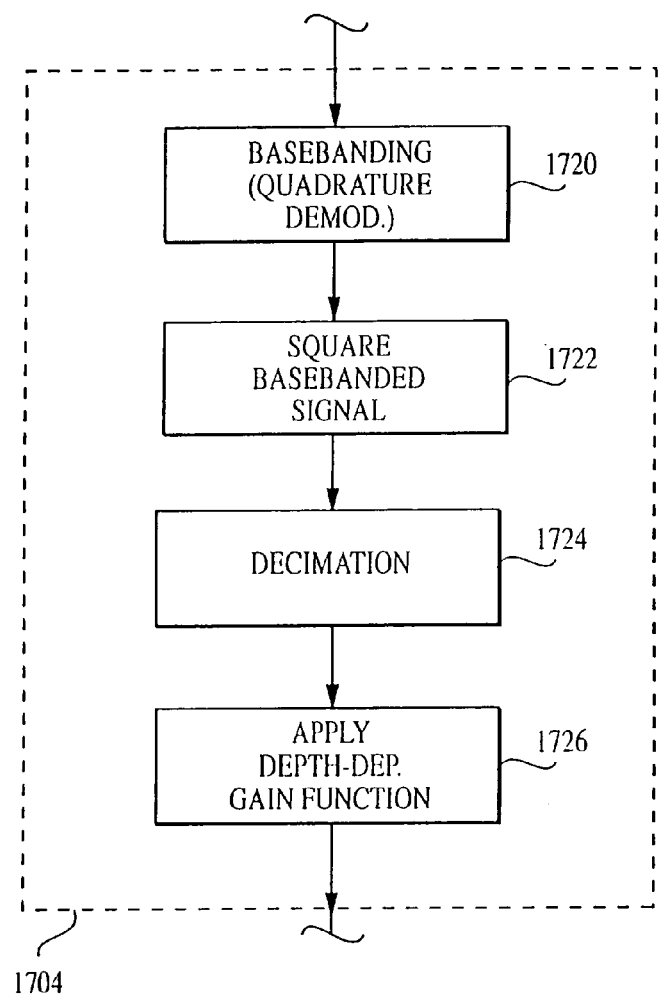
FIG. 17a is a logical block diagram illustrating one exemplary embodiment of the method of processing A-mode signals per the method of FIG. 17.

As shown in FIG. 17*a*, one embodiment of the signal processing (step 1704) associated with the basic A-mode lumen and wall detection approach of FIG. comprises basebanding (quadrature demodulation) the "raw" backscattered A-mode signal (step 1720), squaring the basebanded A-mode signal (step 1722), thereby producing the "envelope-squared" data, and decimation to a predetermined sampling rate (e.g. 2 MHz) per step 1724. The depth-dependent gain (e.g., TGC) is next applied to the envelope-squared data per step 1726 to adjust for propagation loss. These signal processing steps are described in greater detail in the following paragraphs.

Figure 18:
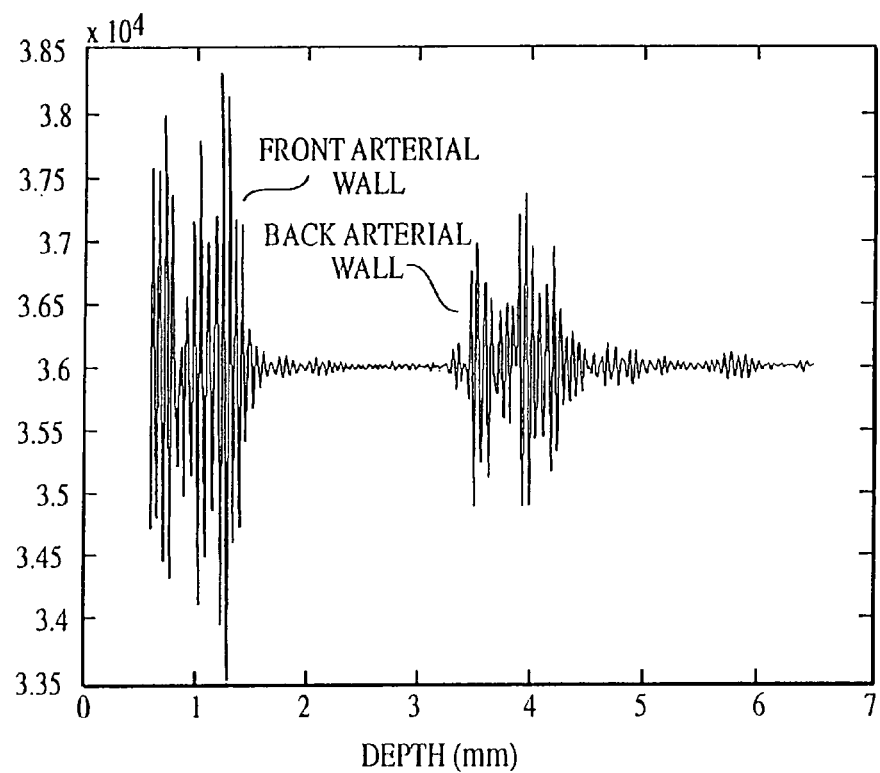
FIG. 18 is a graphical representation of a "raw" A-mode signal as a function of depth within the tissue of the subject being monitored.

FIG. 18 is a plot of the A-mode signal amplitude associated with the radial artery of a living subject, referred to as 'raw' A-mode data herein, versus time. It will be noted that the time axis of FIG. 18 has been converted to depth based on the propagation speed of the ultrasonic energy through the tissue. This conversion is performed since depth is considered a more readily interpreted quantity than time for the purposes of the invention, although it will be appreciated that time (or even other representations such as time-scale) may be used with equal success.

One important feature demonstrated in FIG. 18 is the level or amplitude of the A-mode signal as a function of depth. As illustrated in FIG. 18, there is an obvious range, from about 1.5 mm to 3.35 mm in this example, in which the signal level is quite low. This low signal amplitude is attributable to the low backscattering of energy associated with the blood (lumen) flowing the in blood vessel under examination.

Figure 19:
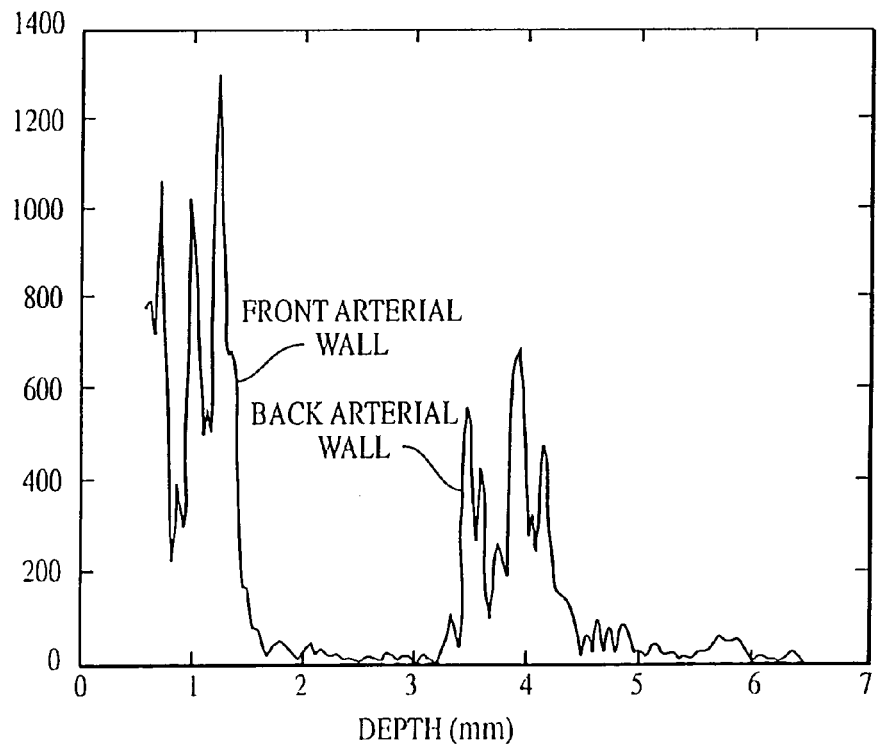
FIG. 19 is graphical representation of the envelope derived from the raw A-mode data of FIG. 18.
Figure 21:
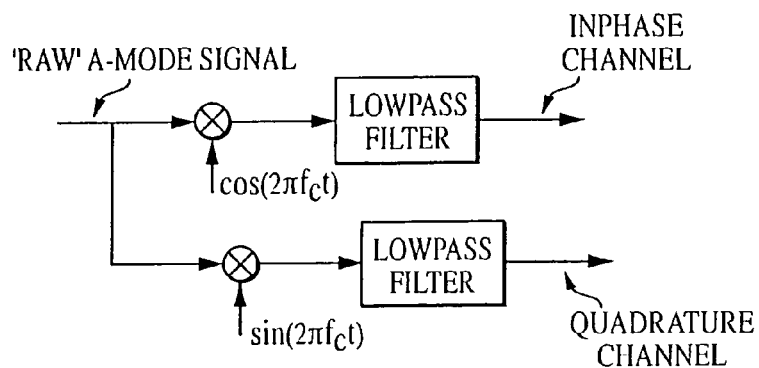
FIG. 21 is a block diagram illustrating the method of quadrature demodulation of the A-mode signal according to the present invention.

In addition, the 16 MHz center frequency used for this example is clearly depicted in FIG. 18. Since the center frequency conveys no information relevant to the location of the arterial walls, the first step of signal processing is to remove the center frequency. This process is denoted as quadrature demodulation (or envelope detection), identified as step 1720 in FIG. 17a. The envelope detected signal associated with the exemplary A-mode signal of FIG. 18 is shown in FIG. 19.

Figure 20:
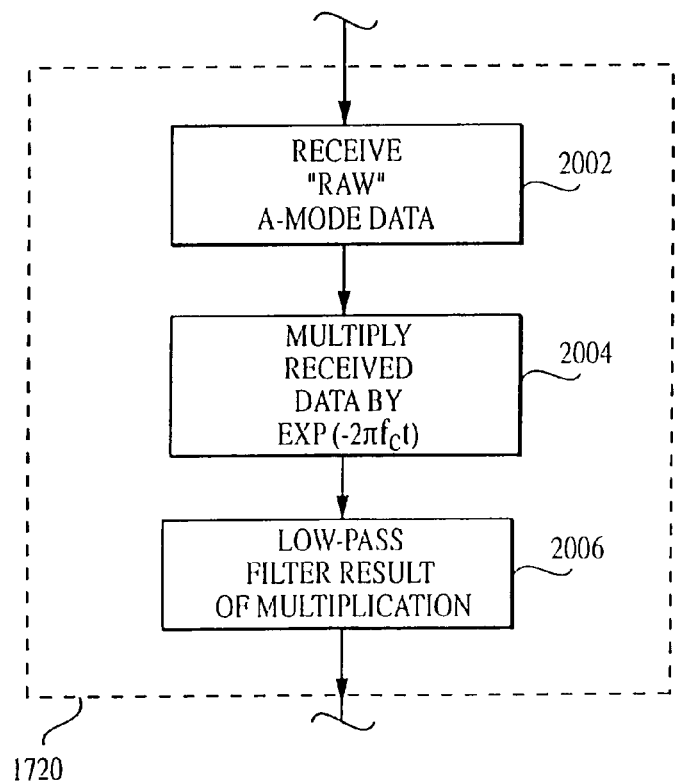
FIG. 20 is a logical flow diagram illustrating the general methodology of quadrature demodulation and A-mode signal filtering according to the invention.

Quadrature demodulation as used in the present embodiment generally comprises multiplication of the A-mode signal by the sine and cosine functions, and lowpass filtering. The purpose of quadrature demodulation is to baseband the A-mode signal, through the removal of the transmit carrier frequency. This method is generally illustrated in FIG. 20. As shown in FIG. 20, quadrature demodulation consists of multiplication of the received backscattered "raw" A-mode signal by the complex exponential, $\exp(-2\pi f_c t)$ where $f_c$ denotes the transmit center frequency of the signal (step 2004). This produces a series of values representing sum and difference frequencies of the complex exponential function and raw A-mode signal. Next, the resulting signal is lowpass filtered (step 2006) to retain only the difference (baseband) frequency components. Since the exponential function is complex, both an in-phase and quadrature channel are produced, designated I and Q, respectively. This process is graphically depicted in FIG. 21.

In the illustrated embodiment, the frequency of the sinusoids is 16 MHz, corresponding to the center frequency, $f_c$, of the A-mode signal. The sampling interval of the sinusoids is equal to that of the digitized A-mode signal that is sampled at an effective rate of 64 MHz. Multiplication by the sine and cosine produces the following:

$$Y_{sin}(nT) = a(nT)\sin(2\pi f_c nT) \qquad \text{(Eqn. 2)}$$

$$Y_{cos}(nT) = a(nT)\cos(2\pi f_c nT) \qquad \text{(Eqn. 3)}$$

Where $a(nT)$ denote the 'raw' A-mode signal with sampling interval $T=1/F_s$, and $F_s$ denotes the sample rate (e.g., 64 MHz). This multiplication is performed for the entire duration of the A-mode line. The in-phase and quadrature components, $X_I(nT_D)$ and $X_Q(nT_D)$ respectively, are produced by lowpass filtering $Y_{cos}(nT)$ and $Y_{sin}(nT)$. Here, $T_D$ denotes the decimated sampling interval.

Figure 22:
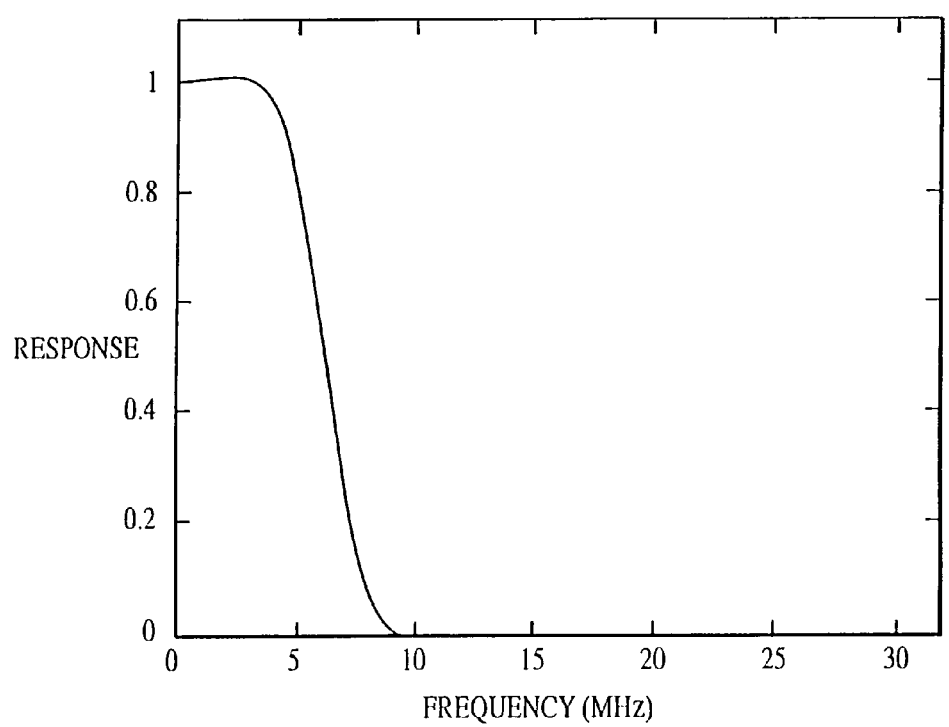
FIG. 22 is a graphical representation of the frequency response of one exemplary embodiment of the lowpass finite impulse response (FIR) filter of the present invention.

Lowpass filtering (step 2006 of FIG. 20) is accomplished in the illustrated embodiment with a finite impulse response (FIR) filter consisting of 37 coefficients. The filter is designed with a passband cutoff of 6 MHz corresponding to an A-mode transducer with 80% bandwidth. This provides for a decimation in sampling by a factor of four. That is, the filter output is produced at a rate of 16 MHz ($=T_D$). The frequency response is shown in FIG. 22. The coefficients associated with this exemplary low-pass design are shown in FIG. 23.

Note that for the illustrated case, the filter output advantageously need only be sampled at a rate of approximately 16 MHz in comparison with the original "raw" A-mode signal that is sampled at an effective rate of 64 MHz.

In the present embodiment of the invention, the magnitude of the complex envelope previously described is the only component required for subsequent processing, although other components of the processed or unprocessed A-mode signal may be used for other purposes if desired. Note that obtaining the magnitude of the complex envelope requires taking the square root of the sum of the squares of the lowpass filtered results. That is, since the result is complex, the magnitude equals the square root of the sum of the in-phase component squared and the quadrature component squared, as shown in Eqn. 4:

$$|E_{sq}(nT_D)| = \sqrt{X_I^2(nT_D) + X_Q^2(nT_D)} \qquad \text{(Eqn. 4)}$$

Figure 24:
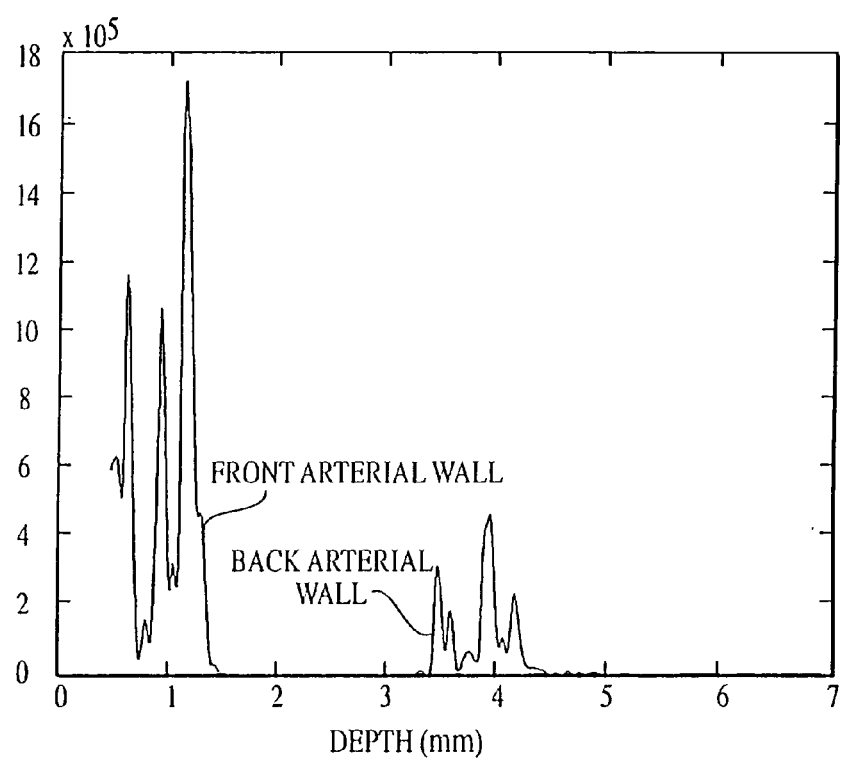
FIG. 24 is a graphical representation of the envelope-squared waveform derived from the A-mode signal of FIG. 18.

However, rather than calculate the magnitude of the envelope, the subsequent signal processing may be applied to the non-square-rooted signal, referred to herein as the "envelope-squared." This latter approach alleviates the need to perform the square root operation, thereby simplifying the resulting algorithmic implementation somewhat. The envelope-squared waveform is depicted in FIG. 24.

The envelope-squared, $E_{sq}(nT_D)$, is derived from the in-phase and quadrature components. This is computed as set forth in Eqn. 5:

$$E_{sq}(nT_D) = X_I^2(nT_D) + X_Q^2(nT_D) \qquad \text{(Eqn. 5)}$$

Figure 25:
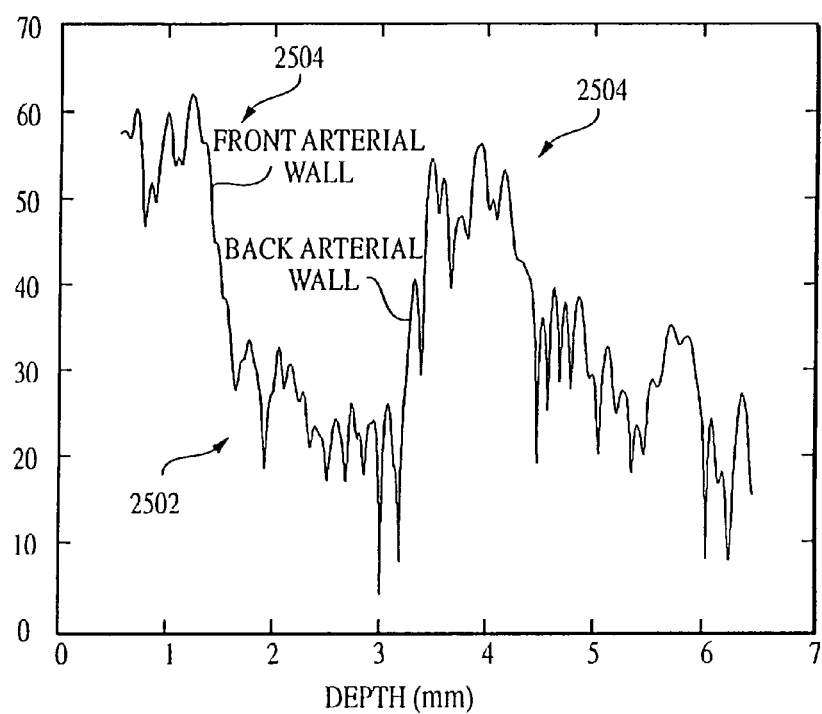
FIG. 25 is a graphical representation of the logarithm (base 10) of the envelope-squared waveform of FIG. 24.

In order to better assess the level of the signal associated with the lumen within the confines of the arterial walls, the logarithm (base 10) of the envelope-squared signal is obtained as shown in FIG. 25. Note that the level of the signal 2502 associated with the lumen is very roughly 30 dB below the signal 2504 associated with backscatter from the arterial walls.

It will be recognized, however, that in certain applications, "false" lumen detection might occur if the lumen detection methodology were based solely on the absolute value of the A-mode signal level. For example, lumen detection criterion based on the absolute signal level alone might erroneously detect lumen where there is none, or conversely miss lumen where it is actually present. Such false detections can arise from a variety of factors including, for example, backscatter and reflections from tissue (veins, musculature, etc) interposed between the transducer element and the blood vessel, movement of the subject during measurement, and the like. Hence, as described in greater detail below, the methodology of the present invention further examines signal artifacts proximate to those produced by the lumen in order to confirm the veracity of any given lumen detection, and positively locate both the lumen and contiguous vessel walls.

A non-linear depth-dependent gain (step 1726 of FIG. 17a) is also applied to the envelope to account for the attenuation to the acoustic A-mode signal as it propagates through the skin, tissue and blood vessels. This depth-dependent gain is often referred to as Time Gain Compensation, or TGC; time and depth being implicitly related in this application as previously described. The expression for the gain is given by Eqn. 6 below:

$$\text{gain} = \text{depth} \qquad \text{(Eqn. 6)}$$

Here the depth is assumed to be in millimeters, and the gain is applied to the envelope-squared. It will be recognized, however, that other gain functions may readily be applied either in place or in concert with that of Eqn. 6 above. Such gain functions may be empirically determined, such as through clinical testing, or determined via other means such as mathematical derivation or anecdotal or historical sampling of the A-mode signal or other parameters related thereto.

Figure 26:
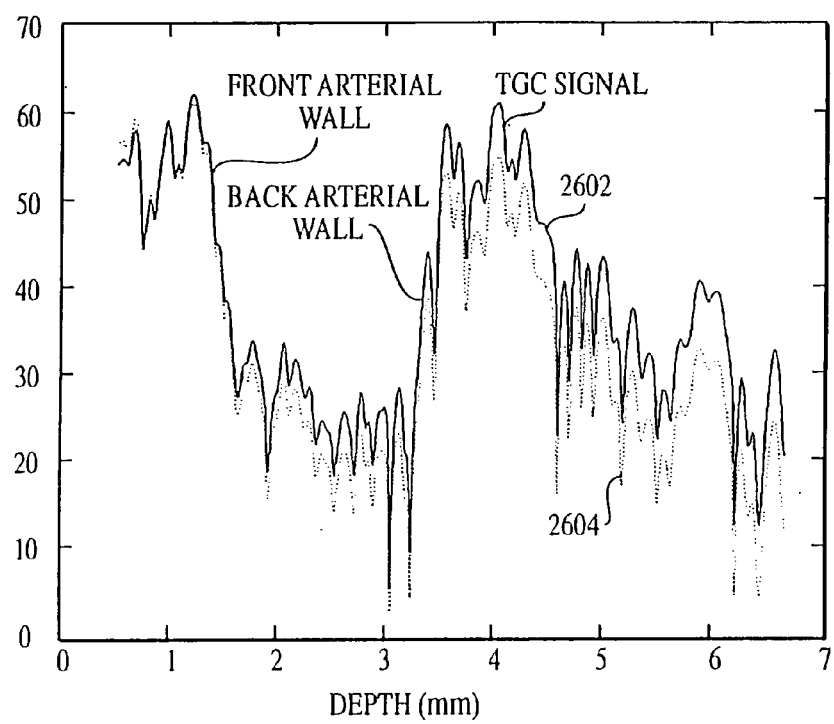
FIG. 26 is a graphical representation of the application of the gain function (TGC) to the envelope-squared of the A-mode signal of FIG. 24.

The application of the gain function to the envelope-squared of the A-mode signal is depicted in FIG. 26. Note that in FIG. 26, the solid curve 2602 corresponds to the A-mode signal with TGC applied, while the dashed curve 2604 corresponds to the A-mode signal without TGC.

It will further be recognized that while the foregoing discussion is cast in terms of signal processing including quadrature demodulation, envelope-squared calculation, and filtering, other types of signal processing and conditioning techniques may be employed consistent with the invention.

Figure 27A:
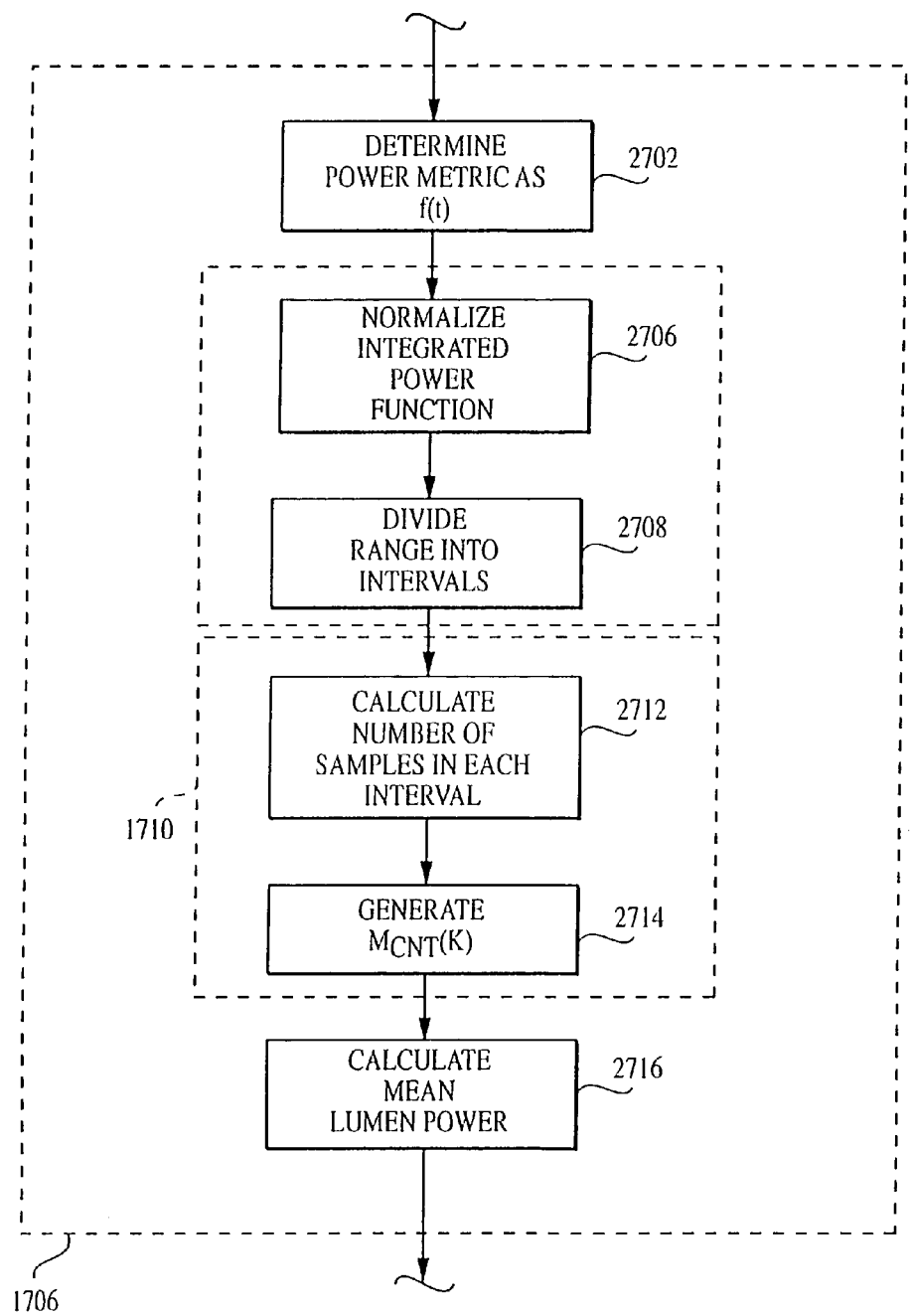
FIG. 27a is a logical flow diagram illustrating the "plateau" method of lumen detection according to the invention.
Figure 27B:
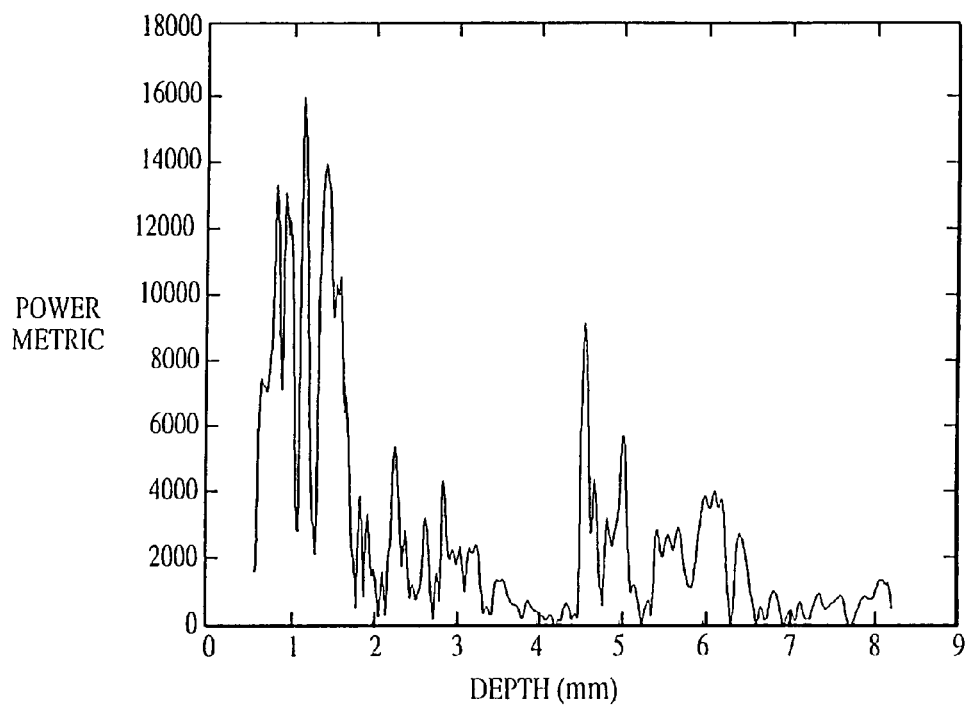
FIG. 27b is a plot illustrating measured backscattered power as a function of depth for a single A-mode line.

After completion of the signal processing, the next step 1706 of the method 1700 of FIG. 17 detects the lumen within the selected blood vessel (e.g., radial artery) for each A-mode line. In one exemplary embodiment, the lumen is detected in step 1706 according to the general methodology of FIG. 27*a* (hereinafter the "plateau" method). As illustrated in FIG. 27*a*, the plateau method 2700 of lumen detection generally comprises first determining a power metric as a function of depth (step 2702), the power metric being based on the aforementioned envelope-squared function. FIG. 27*b* illustrates backscattered power as a function of depth for a single A-mode line.

Next, the power metric is integrated according to Eqn. 7 below:

$$P_{int}(k) = P_{int}(k-1) + P(k) \quad \text{(Eqn. 7)}$$

where $P_{int}(k)$ denotes the power integrated up to the $k^{th}$ sample of the envelope-squared sequence, and $P(k)$ denotes the $k^{th}$ sample of the envelope-squared sequence.

Figure 27C:
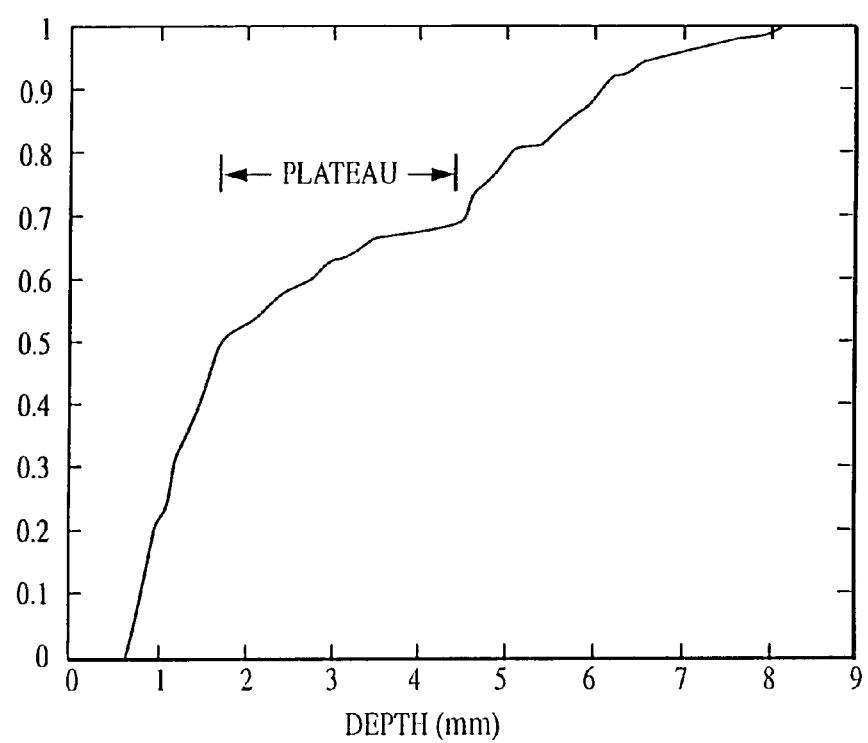

The second step 2704 of the plateau method 2700 consists of identifying the best estimate of the plateau associated with the weak backscatter from the blood within the lumen. As part of this step 2704, the integrated power function is first normalized to unity (step 2706), as is depicted in FIG. 27*c*. Next, in step 2708, the range from zero to unity is divided into a given number of intervals (e.g., eighty equal intervals in the present embodiment; that is, intervals of 0.0125 such that the first interval is 0 to 0.0125, the second from 0.0125 to 0.0250, and so forth). It will be recognized that other numbers of intervals and in fact, non-equal intervals (such as those determined by a function such as a logarithm) may be used as well if desired.

Figure 27D:
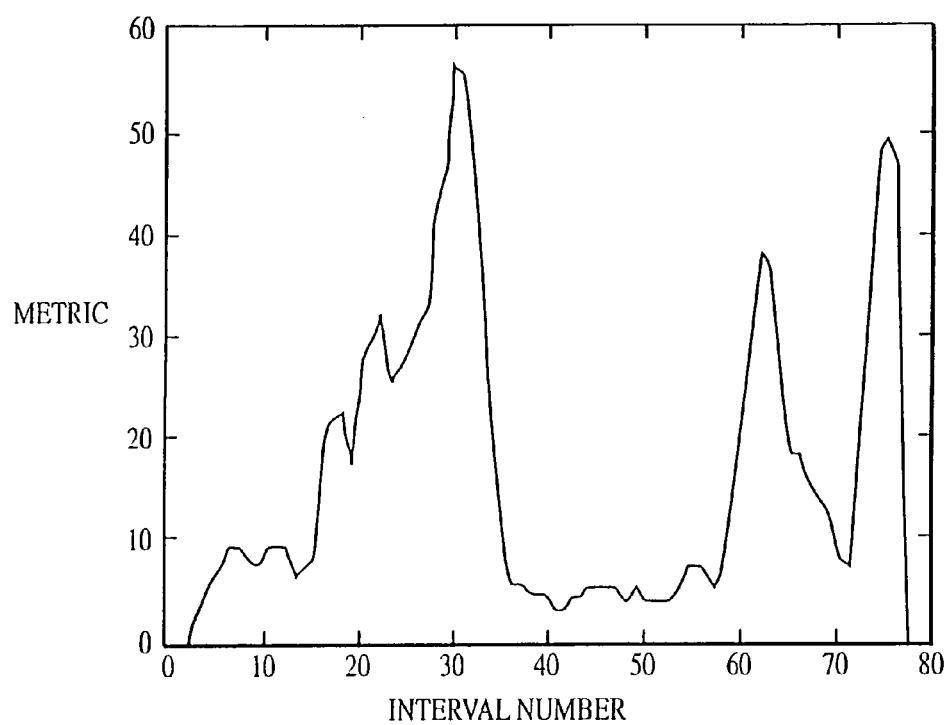

Next, the plateau is detected per step 2710. First, the number of samples occurring within each interval of normalized power is computed (step 2712). The rationale behind this computation is that when the power is low, corresponding to the backscatter from blood for example, many values must be integrated to cross from one integral to the next. Hence, an interval containing many samples is indicative of a plateau (and the lumen). In the illustrated embodiment of FIG. 27*a*, a test consisting of the number of points contained in three consecutive intervals is applied (step 2714), such that the metric is as shown in Eqn. 8 below:

$$M_{cnt}(k) = \sum_{n=k-2}^{k} m(n) \quad \text{(Eqn. 8)}$$

where $M_{cnt}(k)$ denotes the sum of the counts in three consecutive intervals ending with the $k^{th}$ interval, and $m(n)$ denotes the number of samples in the $n^{th}$ interval. This metric is shown in FIG. 27*d* for A-mode line number 50 for a lateral sweep of the radial artery. Note the relatively large peaks 2730 in the intervals above interval number 60. These generally correspond to the low power occurring at deeper depths, which can often times result in false detection of the lumen.

An additional term was added to the foregoing metric to ensure that the plateau owing to low power towards the deeper depths does not trigger a false lumen detection. Specifically, the metric includes the requirement that the three consecutive intervals must be followed by an interval with a low count corresponding to the back arterial wall. Hence, the modified metric is given by Eqn. 9:

$$M_{cnt}(k) = \sum_{n=k-2}^{k} m(n) + \frac{1}{3} \sum_{n=k-2}^{k} m(n) \left( \frac{\frac{1}{3} \sum_{n=k-2}^{k} m(n)}{m(k+2)} \right)^2 \quad \text{(Eqn. 9)}$$

Figure 27E:
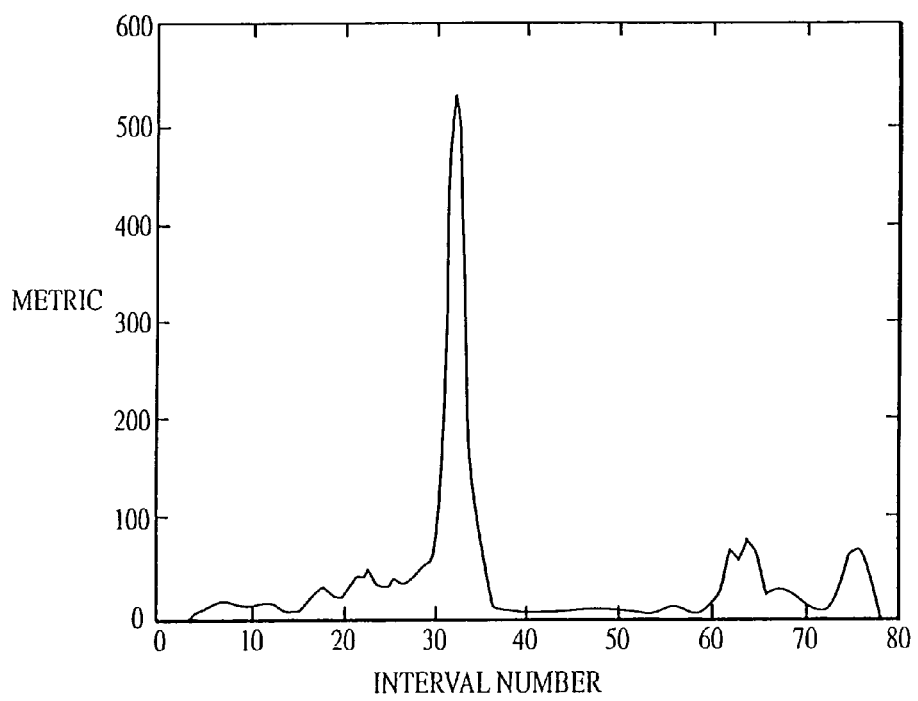
FIG. 27e is a graphical representation of the normalized plateau detection metric for a single A-mode line.

Note that the count, m(k+2), two intervals ahead of the group of three consecutive intervals, is incorporated into Eqn. 9. A plot of this metric for a single A-mode line is shown in FIG. 27*e* for the normalized integrated power of the present example.

Detection of the peak results in the identification of the three consecutive intervals most likely to correspond to the lumen. The total count of samples in all intervals prior to the three intervals corresponding to the peak identifies the depth of the lumen. However, in one exemplary embodiment, the sample point within the A-mode line associated with the lumen for the purpose of the subsequent arterial wall search is derived from the total number of samples in all intervals from the first interval up to (and including) the first interval in the three successive intervals. Hence, the sample associated with the lumen for the given A-mode line is estimated per Eqn. 10:

$$L = \sum_{k=1}^{K-2} m(k) \quad \text{(Eqn. 10)}$$

where L denotes the number of samples prior to the lumen area, and K denotes the "pointer" to the third of the three consecutive intervals for which the peak was detected.

In addition, an estimate of the mean of the lumen power may be derived from the power contained in one or more of the three consecutive intervals (step 2716). For example, in one exemplary approach, mean lumen power is determined from the second of the three consecutive intervals by simply averaging the sample values of the envelope-squared that correspond to this interval. This estimate of the lumen backscattered power is subsequently used in conjunction with the estimated position of the detected lumen to detect the arterial walls, as described in greater detail below.

It is noted that plateaus in the integrated power profile may result from other sources. Specifically, in the case of the human radial artery, such plateaus may also be induced by the presence of one or more veins located between the applanation device and the blood vessel of interest, or by the presence of cysts or other growths. While more common, plateaus due to veins are generally quite small in comparison to the "true" plateau of interest associated with compression of the radial artery, due largely to the comparatively smaller vein diameter (and wall thickness). Furthermore, the methodology of the present invention effectively overcomes this issue by conducting measurements of blood vessel diameter (and integrated backscattered power) at applanation pressures above the level necessary to collapse the comparatively thin-walled veins. Such collapse of the veins generally occurs at pressures well below that necessary to significantly affect the diameter of the larger blood vessel (e.g., radial artery), thereby allowing for an elegant solution to the problem of potentially "false" plateaus due to veins.

In contrast to veins, cyst or growth-related artifacts generally occur only in a very small fraction of the population, and are frequently spatially localized to the extent that relocation of the transducer at another location over the artery will eliminate any effects resulting there from. Additionally, the cystic areas do not have corresponding pulse pressure or motion components related to pulse pressure, and hence can be readily identified and screened using any number of signal processing techniques well known to those of ordinary skill.

In a second embodiment, detection of the lumen in step 1706 of FIG. 17 is accomplished by computing the average power within a predetermined distance (e.g., 1 mm) interval along the A-mode line, hereinafter referred to as the "interval" method. The 1 mm interval corresponds to a time interval along the A-mode line of 1.33 usec, assuming the speed of propagation is 1500 met/sec and is derived from Eqn. 11:

$$D = ct/2 \qquad \text{(Eqn. 11)}$$

where:
D=depth,
c=speed of propagation,
t=time of propagation

The factor of 2 in Eqn. 11 accounts for bi-directional acoustic wave propagation. For a sampling rate of 16 MHz as previously described, 1.33 usec corresponds to approximately 22 samples along the de-sampled A-mode line.

The 1 mm interval for power calculation was selected in the illustrated embodiment based on the observation by the Assignee hereof that the diameter of the blood vessel under examination (e.g., radial artery) will exceed 1 mm in essentially all of the adult human population; hence, the power calculation is reasonably assured to constitute signal attributable only to the lumen. However, it will be recognized that this interval may be adjusted based on factors such as measurement of non-adult populations, use of other blood vessels, and/or use of the technique on other species. It is also noted that the 1 mm interval referenced above also advantageously provides a 'reasonable' number of samples to average for an estimate of the A-mode signal power.

For a sampling rate of 16 MHz, the aforementioned 1 mm interval corresponds to a time interval of 1.33 usec, or approximately 22 samples. The estimate of power at time $nT_D$, $P_{1mm}(nT_D)$, is computed according to Eqn. 12:

$$P_{1mm}(nT_D) = \sum_{k=1}^{22} E_{sq}[(n-11+k)T_D] \qquad \text{(Eqn. 12)}$$

Figure 28A:
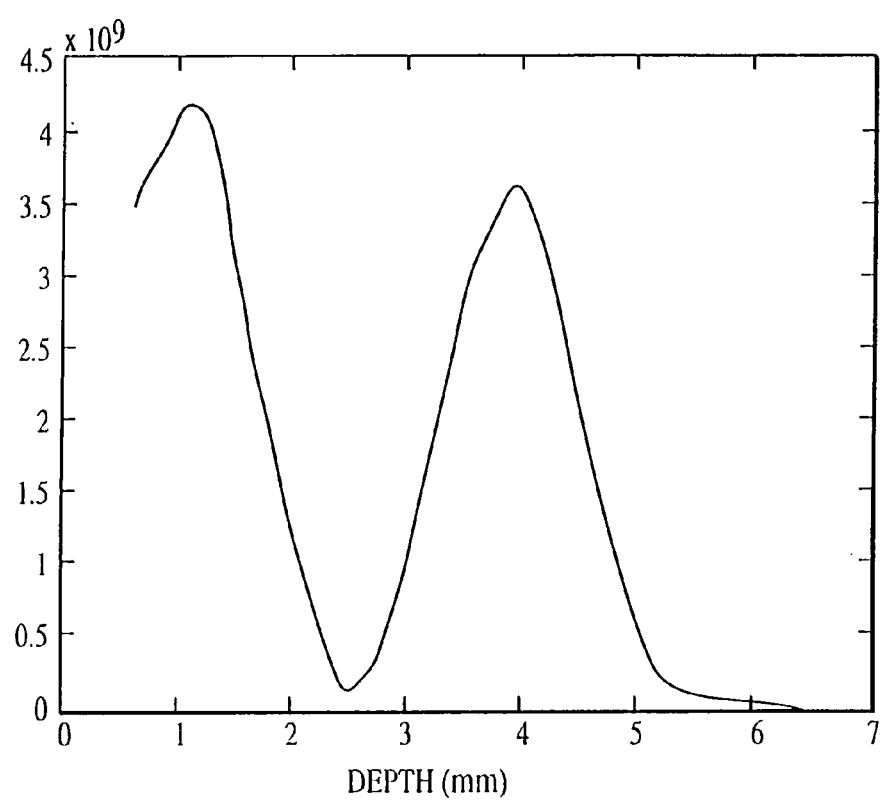
FIG. 28a is a graphical representation of the power profile (1 mm interval) along the TGC-corrected A-mode line of FIG. 26.

An exemplary plot of the acoustic power in a 1 mm interval along the line of TGC corrected A-mode data is depicted in FIG. 28a.

The location of the lumen (e.g., blood) within the confines of the radial artery is detected as the first minimum in the 1 mm average power calculation. The search for this minimum begins at a predetermined point along the A-mode line, (e.g. 1 mm), and continues to a second predetermined depth, chosen in the present illustration as 7 mm. This range of 1 mm to 7 mm was selected based on the observation that the front wall of the radial artery (i.e., that wall first encountered by the acoustic energy radiated from the transducer) will occur within this interval in essentially all of the adult human population. It will also be noted that the aforementioned minimum is clearly distinguishable in the plot of FIG. 28a, thereby advantageously allowing for ready detection in an A-mode signal of good quality (i.e., low noise level and other artifacts). The detection of minima within electronic signals may be accomplished by any number of techniques well known in the electronic arts, and accordingly is not described further herein.

Figure 28B:
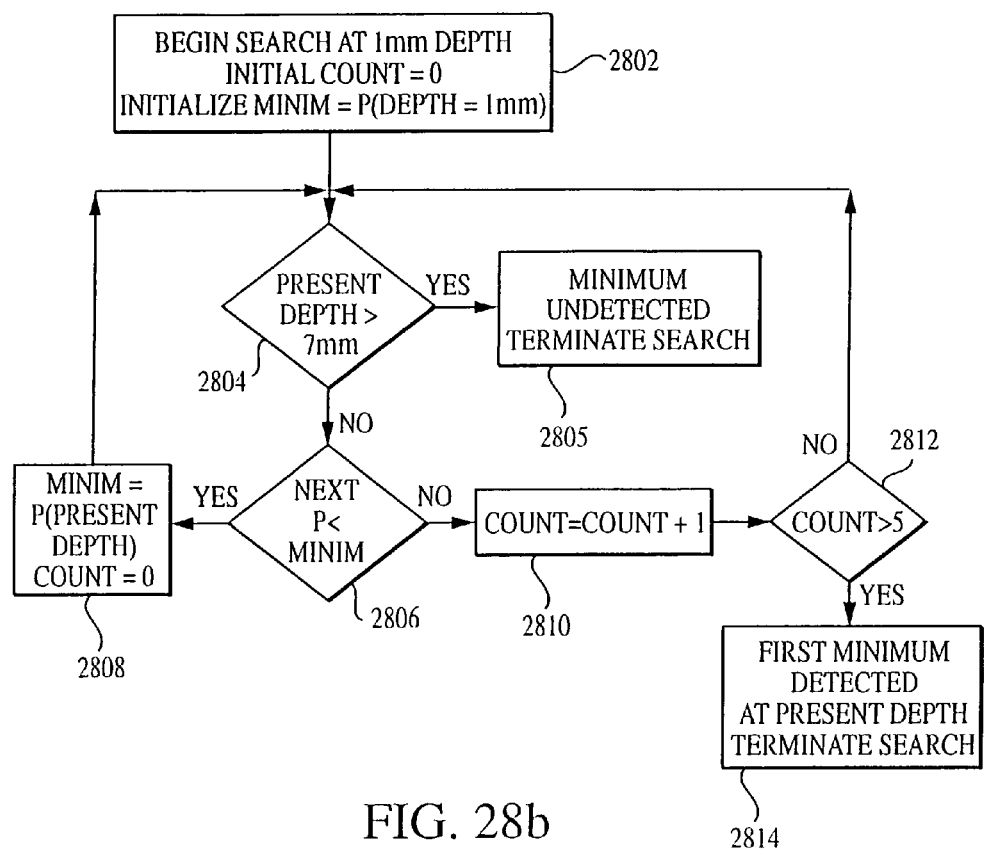
FIG. 28b is a logical flow chart illustrating the "interval" methodology of lumen detection using A-mode signals according to the invention.
Figure 28C:
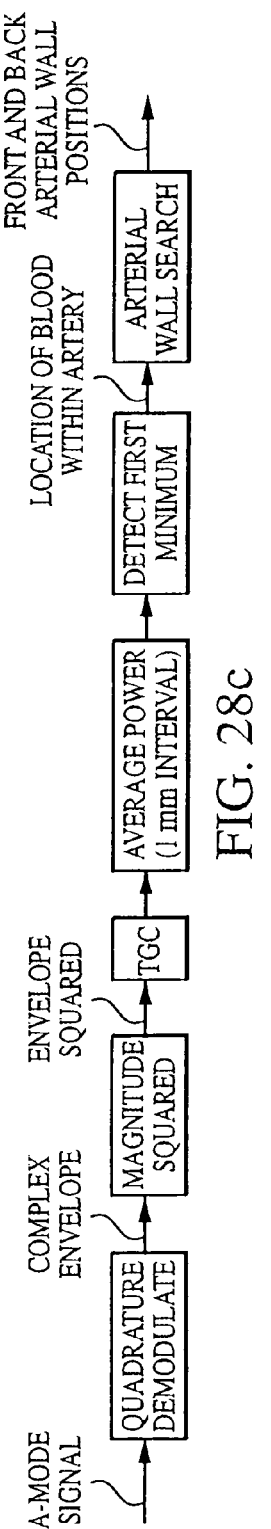
FIG. 28c is a functional block diagram illustrating one exemplary embodiment of the methodology of FIG. 28b.

FIG. 28b graphically illustrates lumen detection using the aforementioned "interval" method. As illustrated in FIG. 28b, lumen detection comprises beginning the search for the artery wall at the pre-selected depth, 1 mm in the present case (step 2802). The minimum power is initialized at the power for depth=1 mm. Next, the relationship to the maximum specified depth (e.g., 7 mm in the foregoing example) is determined per step 2804. If the maximum depth has been exceeded, the minimum has not been detected, and the search is terminated (and optionally restarted) per step 2805. If the maximum specified depth has not been exceeded in step 2804, the next power sample is analyzed per step 2806. If less than the minimum value, the minimum is reset to the power level P associated with the sample of the current depth, and the count reset to zero (step 2808). Conversely, if the next power sample is not less than the current minimum, then the count is incremented by one (step 2810), and the integer number of the count analyzed (step 2812) to determine its relationship to a predetermined count limit parameter (e.g., 5 in the illustrated embodiment). If the current count exceeds the count limit parameter, the first minimum is assumed to have been detected at the current depth, and the search is terminated (step 2814). If not, steps 2804 through 2814 are repeated again as applicable. FIG. 28c further illustrates this process with respect to one exemplary signal processing architecture.

During the foregoing procedure, the level of the A-mode signal associated with backscatter from lumen, $E_{sq}$(blood), can be easily estimated once the region of lumen has been identified. The estimate is computed as a simple average over samples of the envelope-squared over a range centered at the depth for which lumen has been detected. The average is computed according to the exemplary relationship of Eqn. 13:

$$E_{sq}(\text{blood}) = \frac{1}{15} \sum_{k=1}^{15} E_{sq}[(N_{blood} - 7 + k)T_D] \qquad \text{(Eqn. 13)}$$

where $N_{blood}$ denotes the index of the envelope squared corresponding to the depth of blood detection. Note that in Eqn. 13, the average is computed over fifteen samples of the envelope squared, although it will be recognized that other values may be substituted depending on the particular application.

After the lumen has been detected using, e.g., either the plateau or interval methods, the front and back arterial walls are detected, and the spatial positions thereof (i.e., depths relative to the sensor unit) are estimated. Specifically, the front arterial wall is assumed to occur between the sensor unit and the depth of the detected lumen and in particular, generally in the vicinity where the A-mode signal is decreasing to the integrated power or signal level associated with the lumen. This assumption is founded on the knowledge that the lumen of the blood vessel is immediately adjacent the wall (i.e., on its far side with respect to the transducer). Similarly, the back arterial wall is assumed to occur at a depth greater than that of the lumen signal, and generally in the vicinity where the integrated power or signal level rises sharply above the level associated with the lumen. These changes in the A-mode integrated power or signal level corresponding to the front and back wall of the artery are readily observable, for example, in the TGC A-mode data.

In a first exemplary embodiment (FIG. 29a), the method of wall detection utilizes (i) the detected position within the lumen from which to begin the search for the arterial walls, and (ii) the estimate of the mean lumen power from which to derive detection thresholds as described with respect to FIG. 27a above. The detected position of the lumen along the A-mode line serves as the start for the search for the back wall. Starting from this position (step 2902), the integrated power is computed by summing consecutive samples of the square of the envelope of the A-mode signal (step 2904). The formulation is given by Eqn. 14:

$$P_{bk}(m) = \sum_{k=K_{st}}^{m} P(k) \qquad \text{(Eqn. 14)}$$

where $P_{bk}(m)$ denotes the integrated power in the direction of the back wall starting at sample $K_{st}$ up to sample m, and P(k) denotes the $k^{th}$ sample of the square of the envelope of the A-mode signal. When $P_{bk}(m)$ exceeds the prescribed threshold, the back wall is assumed detected and the corresponding sample value, m, denotes the depth of the back wall (step 2906). Note that the sample number along the A-mode line and depth are related; the actual depth is derived from the sample number as shown in Eqn 15:

$$D = cN_{samp}/2F_s \qquad \text{(Eqn. 15)}$$

where c denotes the speed of propagation, $N_{samp}$ denotes the sample number, and $F_s$ denotes the sampling rate associated with the envelope-squared sequence.

The front wall is detected in much the same manner as the back wall. Starting from the same position used for the back wall, the integrated power is computed by summing consecutive samples of the square of the envelope of the A-mode signal in the direction of the front wall. Hence, the samples are taken in descending order from sample $K_{st}$. When the integrated power exceeds the prescribed threshold, the front wall is assumed detected and the corresponding sample value determines the depth of the front wall.

Figure 29A:
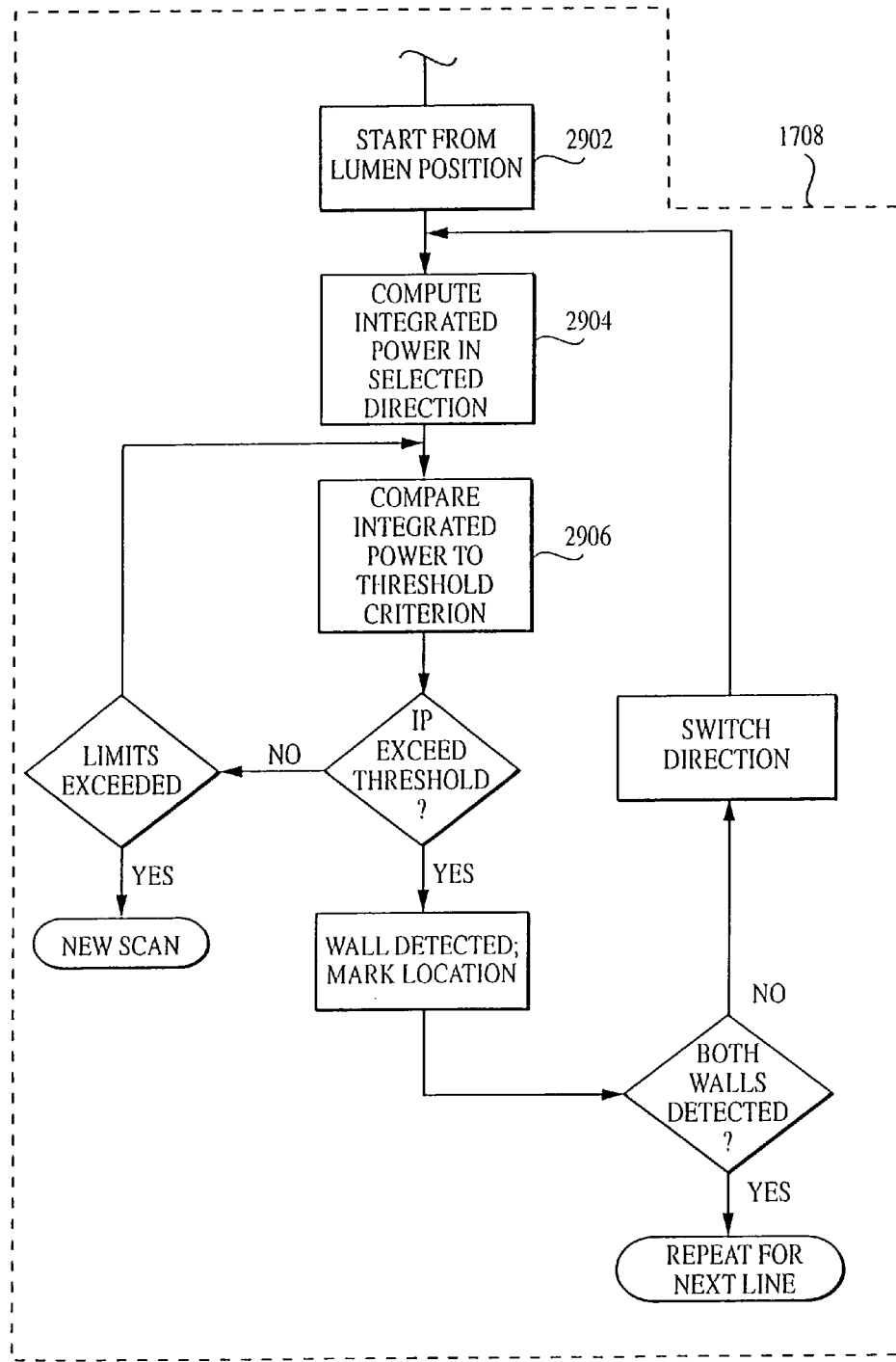
FIG. 29a is a logical flow chart illustrating a first exemplary methodology of front and back wall detection based on integrated power calculation.

In the embodiment of FIG. 29*a*, a front wall threshold equal to 500 times the aforementioned lumen mean power, and a back wall threshold equal to 50 times the lumen mean power, are utilized. These values were determined empirically by the Assignee hereof with a specific depth-dependent gain (e.g., TGC) function. It will be recognized, however, that other threshold values and types of criteria may be used. For example, variable thresholds whose value varies as a function of other parameters (e.g., clutter in the lumen, or attenuation in interposed tissue) may be substituted. Furthermore, it will be recognized that the relationship between the front and back wall threshold criteria may or may not respect a predetermined relationship. For example, the front wall threshold may be determined as a function of the back wall threshold, or alternatively be completely independent there from. Other variations are possible; see for example the discussion of scoring and weighting below.

Furthermore, to facilitate the processing, inter-line averaging of the A-mode lines as is well known in the signal processing arts may be performed prior to lumen and wall detection. This technique can be used to improve performance and robustness of the system, both in terms of lumen detection and arterial wall depth estimation.

In an alternative embodiment of the method for detecting the arterial walls (FIG. 29*b*), the amplitude of the envelope squared, $E_{sq}(nT_D)$, is compared to the estimated signal level associated with backscatter from blood, $E_{sq}(blood)$. This is distinguished from the integral power calculation approach previously described. As before, the search for the front wall is in the direction towards the transducer element, that is, in the direction of decreasing depth. When the amplitude of the envelope-squared satisfies a designated criterion (e.g., exceeds four times the estimated signal level), this amplitude is attributed to backscatter from the front wall. The depth of this occurrence is designated to be the location of the front wall, subject to optional subsequent confirmatory processing, if desired. Note that alternatively (or simultaneously), criterion other than that relating to the amplitude of the envelope-squared variable may be employed.

The search for the back wall is performed in a similar manner to that described for the front wall. Specifically, the search begins at the depth of the detected lumen, but proceeds in the direction of increasing depth (i.e., away from the ultrasonic transducer). As with the front wall, when the amplitude of the envelope-squared exceeds satisfies a designated criterion, this amplitude is attributed to backscatter from the back wall. The depth of this occurrence is assumed to be the location of the back wall.

Figure 29B:
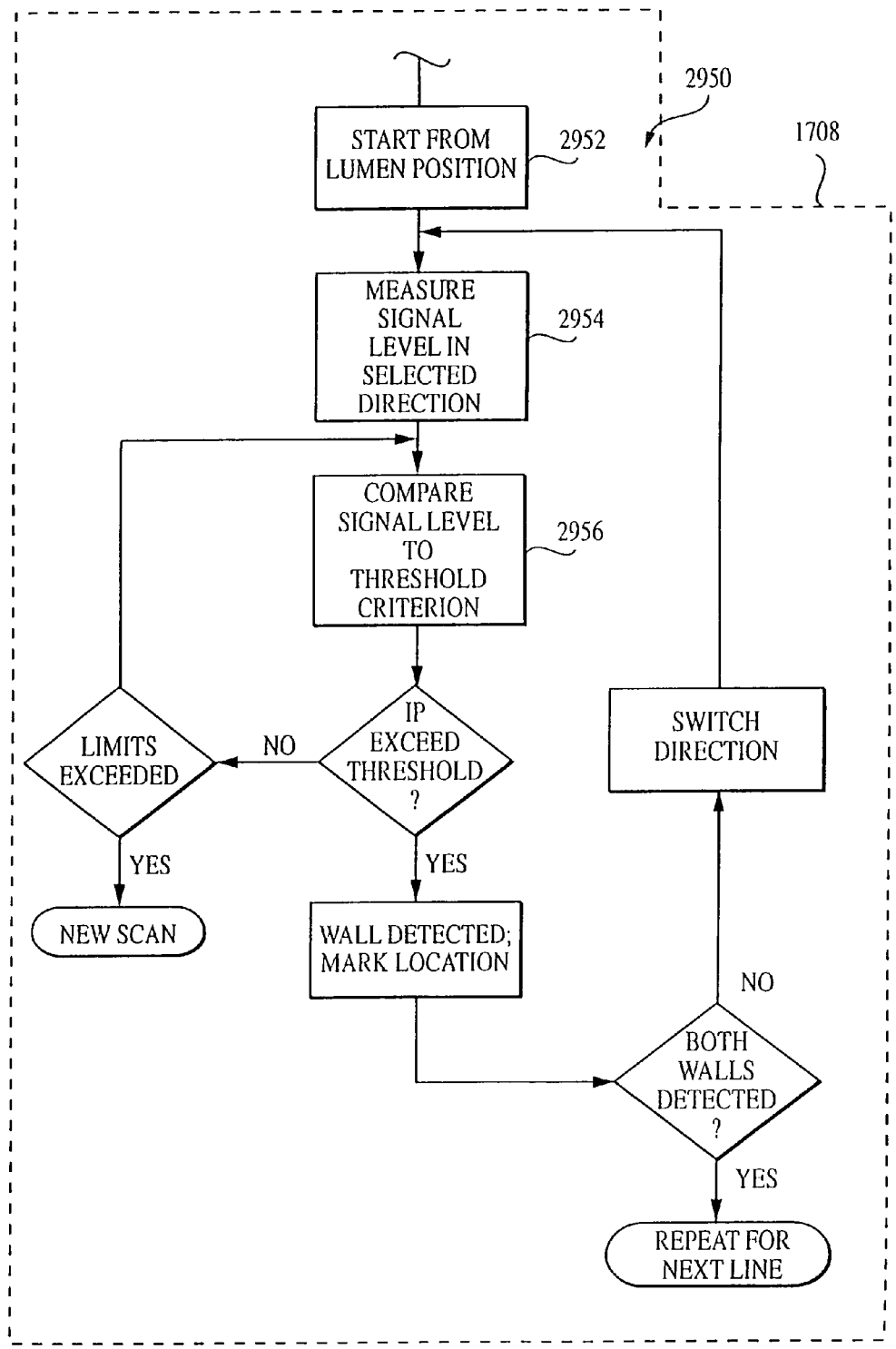
FIG. 29b is a logical flow chart illustrating a second exemplary methodology of front and back wall detection based on envelope-squared signal level determination.
Figure 30:
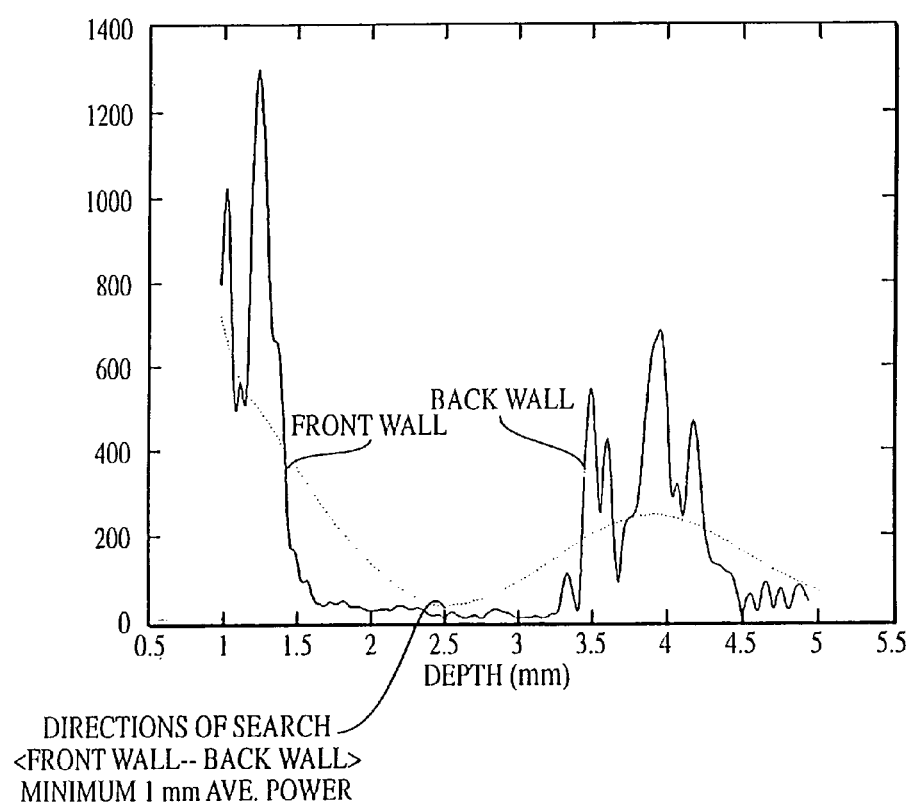
FIG. 30 is a graphical representation of the relationship between the average power calculation and the front and back wall artifacts present in the typical A-mode envelope according to the method of FIG. 29b.

Accordingly, a simple search algorithm may be used in conjunction with the signal level (envelope-squared) methodology to identify the locations associated with the front and back arterial walls when the A-mode data is of "reasonable" quality. Specifically, as shown in FIG. 29*b*, the method 2950 comprises first comparing the A-mode signal level to the signal level of the lumen in both (i) the direction toward the transducer, and (ii) in the direction away from the transducer, starting at the depth where the lumen signal was detected (step 2952). The signal level is measured in the selected direction (step 2954); when the signal level is found to meet one or more predetermined criteria (e.g., the signal level of (i) or (ii) above being "n" times as great as the signal level associated with the lumen), the signal is assumed to correspond to the arterial wall (step 2956). The point along the A-mode line towards the transducer at which this criterion is met is denoted as the location of the front arterial wall, and similarly, the point along the A-mode line away from the transducer at which this criterion is met is denoted as the location of the back arterial wall. This is graphically depicted in FIG. 30, which illustrates the relationship between the average power calculation 3002 and the front and back wall artifacts 3004, 3006 present in the A-mode envelope 3008.

Figure 31:
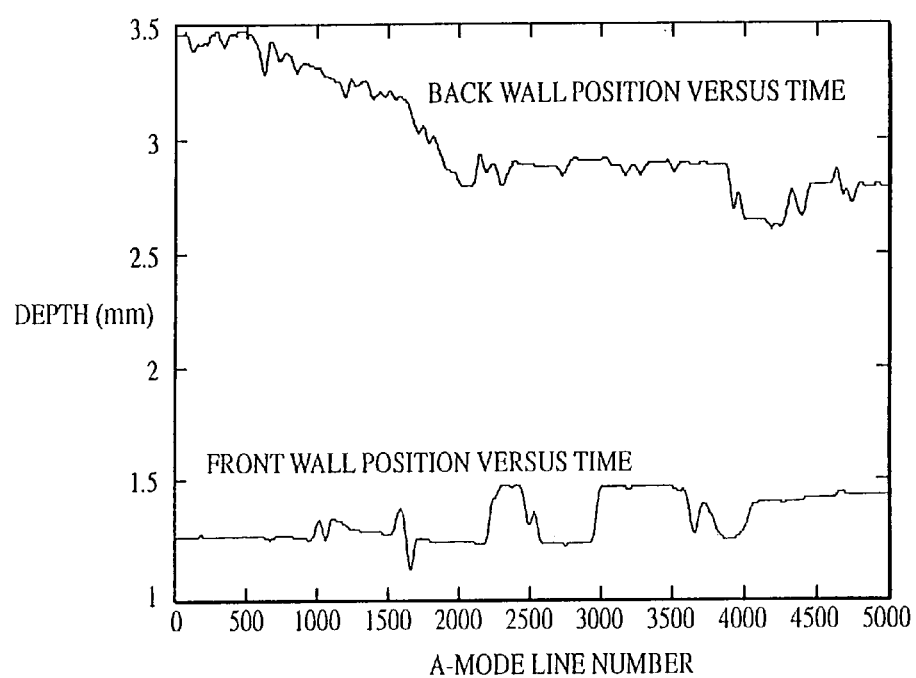
FIG. 31 is a graphical representation of the positions of the front and back walls of an exemplary blood vessel as a function of time (based on a sampling of 5000 A-mode signal lines) using the method of FIG. 29b.

Note that the processes of computing the envelope-squared, determining the corresponding average power in the designated interval (e.g., 1 mm) and the lumen signal, and detection of the front and back arterial walls, is performed in the present embodiment on an A-mode "line-by-line" basis. The arterial wall positions determined in this manner for an exemplary A-mode data set consisting of 5000 lines is shown in FIG. 31. However, such line-by-line analysis may be substituted with other analytical approaches or increments, such as for example portions of a line, or groupings of multiple lines (whether contiguous or otherwise), or line averaging.

Once the relative wall positions are determined, the diameter of the blood vessel may be simply determined by taking the difference in depth between the rear and front walls. For example, if the rear wall occurs at a depth of 3.5 mm, and the front wall at a depth of 1.5 mm, the diameter of the blood vessel can be estimated at (3.5 mm–1.5 mm)=2.0 mm. This determination is made in one embodiment using smoothed wall position estimates (i.e., those which are mathematically averaged of smoothed using other signal processing techniques) which are derived as previously described herein.

It will be appreciated that while the foregoing exemplary methodologies of wall detection (e.g., integrated power and envelope-squared signal level) are described in terms of both front and back walls of the blood vessel, either the front or back wall detection approaches may be applied separately and/or in isolation. For example, if it is determined that for a certain subject being evaluated (or group of subjects having some common characteristic) that the front wall artifact is particularly weak or otherwise unreliable, back wall detection may be weighted more substantially in compensation. Similarly, if the clutter in the blood vessel under examination is significant, the more affected wall may be selectively de-emphasized in terms of weighting. Other such modifications may also be employed depending on the particular application.

Additionally, it will be recognized that the integrated power threshold and envelope-squared signal level approaches may be used either alone or in combination, or other methods (e.g., so-called "boxcar" averaging of the type well known in the signal processing arts) may be employed. For example, parallel computation of envelope-squared signal level and integrated power may be performed, and the calculated values compared to the applicable threshold criteria (e.g., 4 times lumen signal level, and 500 times mean lumen power, respectively). The results of these comparisons may then be used to determine the relative reliability or confidence in the wall detection, such as by calculation of a "confidence level" metric which can be subsequently used by system and/or user. If the wall detection scores for both the integrated power and envelope-squared approaches are high, the resulting confidence metric is high; if the wall detection scores for one technique is high and the other low, then the value of the confidence metric is reduced, and subsequent confirmatory processing is indicated.

Furthermore, it will be appreciated that in the context of wall detection as a whole, various forms of scoring or weighting known in the signal processing arts may be used in substitution for, or conjunction with, the aforementioned criteria. Such techniques advantageously increases the robustness of the system under actual clinical use. For example, in one alternative embodiment, A-mode signals having an envelope-squared or integrated power value meeting or exceeding a discrete value (e.g., 4 times estimated signal level in the case of signal level, or 500 times the mean lumen power in the case of the integration approach) are assigned a score of "1.0". Signals having a value less that this discrete value are assigned scores based on their relationship to a window function w(x), such that values falling below a predetermined threshold (e.g., 2 times estimated signal level, or 250 times mean lumen) are given a score of 0.0, and values between the predetermined threshold and the designated criterion are assigned scores between 0.0 and 1.0 according to the function w(x).

As yet another alternative, the envelope-squared or integrated power values associated with given A-mode measurement may be weighted based on some extrinsic or intrinsic "quality factor" which is related to the quality of data sampled during that interval. As a simple example, if the subject under evaluation moves during a given series of A-mode lines, the quality of data may be reduced, and accordingly any lumen/wall detection computations performed based on this data may be artificially reduced in weighting with respect to other samples.

As yet another alternative, "locational" weighting and/or scoring may be applied, such that envelope-squared or integrated power values generated by A-mode lines corresponding to certain depths may be adjusted. For example, as previously described, the likelihood of finding the front wall of the radial artery in an adult human less than 1 mm from the surface of the skin is exceedingly low; accordingly, an envelope-squared or integrated power value derived from the first "N" A-mode lines (corresponding to the depth of 1 mm) would be heavily de-valued or even eliminated (i.e., zero-weighted).

Similarly, interval-to-interval processing may be conducted such that wall artifact determined in non-contiguous A-mode line intervals is marked as an ambiguity requiring resolution. If a front wall artifact is detected in the first 1 mm depth interval, and again in the third, it can be assumed with some level of confidence that either (i) the wall artifact detected in the first interval is the front wall, and the artifact detected in the third interval is the back wall, or (ii) the first artifact was noise, and the third-interval artifact is the true front wall signal. Such ambiguity can be resolved through any number of techniques, such as the application of the aforementioned "locational" weighting to eliminate the first artifact based on low likelihood of occurrence in the adult population, or the use of sampling of subsequent A-mode signals for those intervals.

The present methodology also includes significant smoothing/filtering of the signal where needed. Such smoothing/filtering furthermore eliminates the time variations that occur from systole to diastole, as well as beat-to-beat variations caused by respiration. Such signal smoothing/filtering is generally well understood in the signal processing arts, and accordingly is not described further herein.

It will also be recognized that the accuracy of the wall detection methodology described herein is in some ways coupled to the ability to produce narrow ultrasonic transmit and receive beams. Specifically, two-way beam response should be sufficiently narrow to fit within the lumen (i.e., the cross-sectional area of blood flow) of the blood vessel under evaluation when the ultrasonic transducer is in the vicinity of its optimal position with respect to the blood vessel. Otherwise, backscatter from the sidewalls of the blood vessel may impede detection of the lumen, and degrade the accuracy of the estimates of the spatial position of the front and back walls.

Another consideration in the evaluation of front and back wall position is the relative compliance and compressibility of the tissue during applanation. Under predominantly static wall position evaluation such as described above with respect to FIGS. 17-31, the absolute and relative positions of the blood vessel walls within the tissue do not vary significantly. However, when assessing hemodynamic parameters of a blood vessel based on such wall position determinations (discussed with respect to FIGS. 34-37 below), wherein the blood vessel and at least a portion of the surrounding tissue are compressed during applanation of the tissue as previously described with respect to FIG. 6 herein, the relative and absolute positions of the front and rear walls change.

Figure 32:
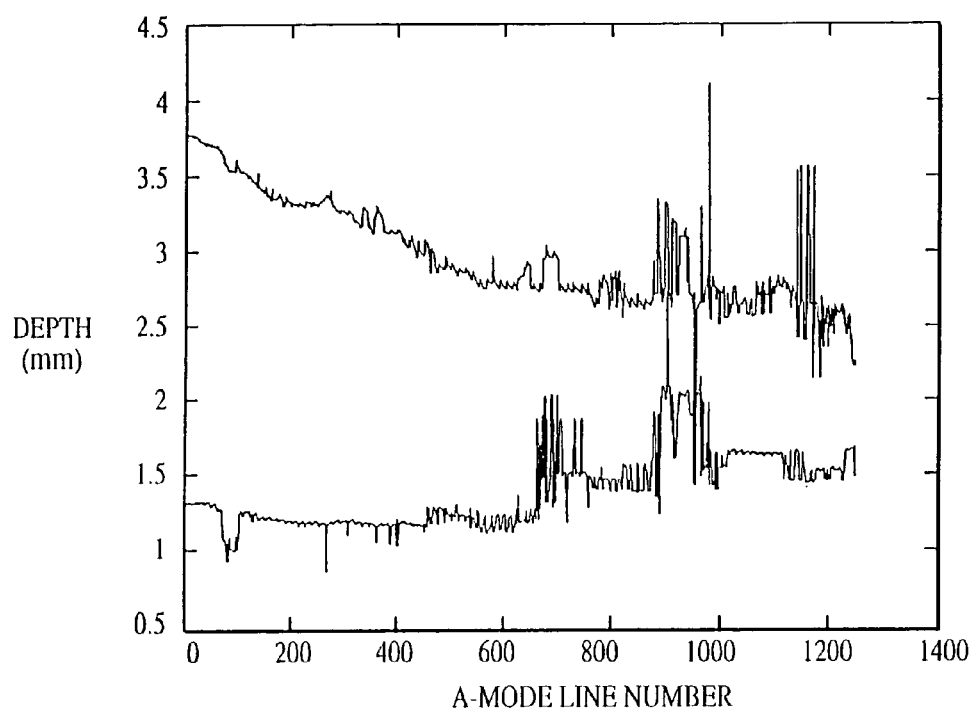
FIG. 32 is a graphical representation of the positions of the back wall of a blood vessel as a function of time during applanation by an external applanation device.
Figure 32A:
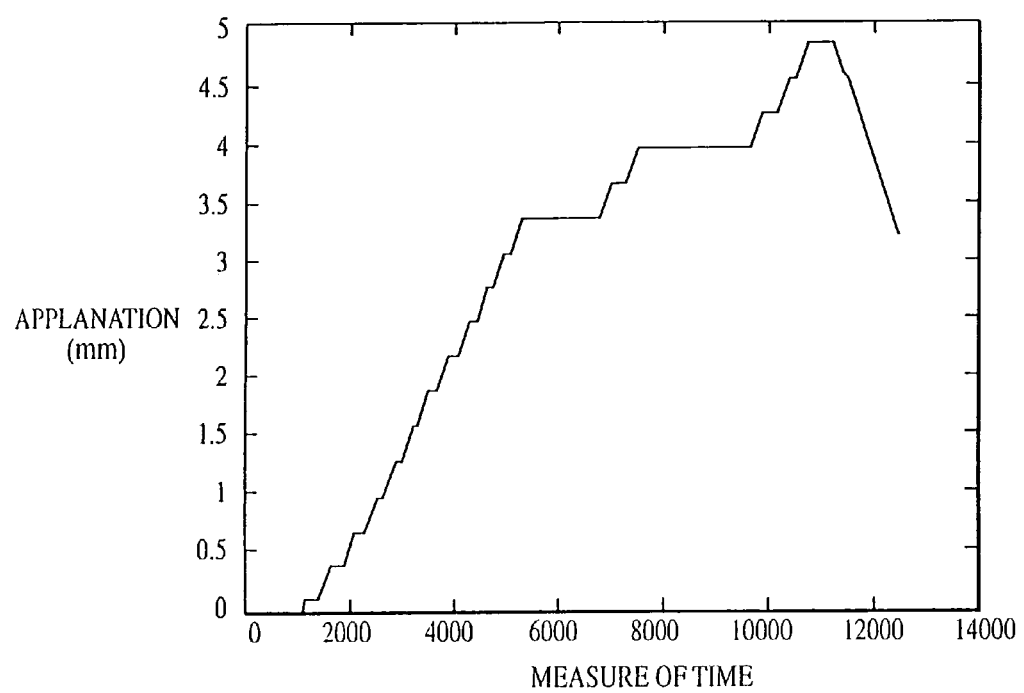
FIG. 32a is a graphical representation of the linear position of the applanation device (mm) as a function of time during applanation of a typical radial artery.
Figure 32B:
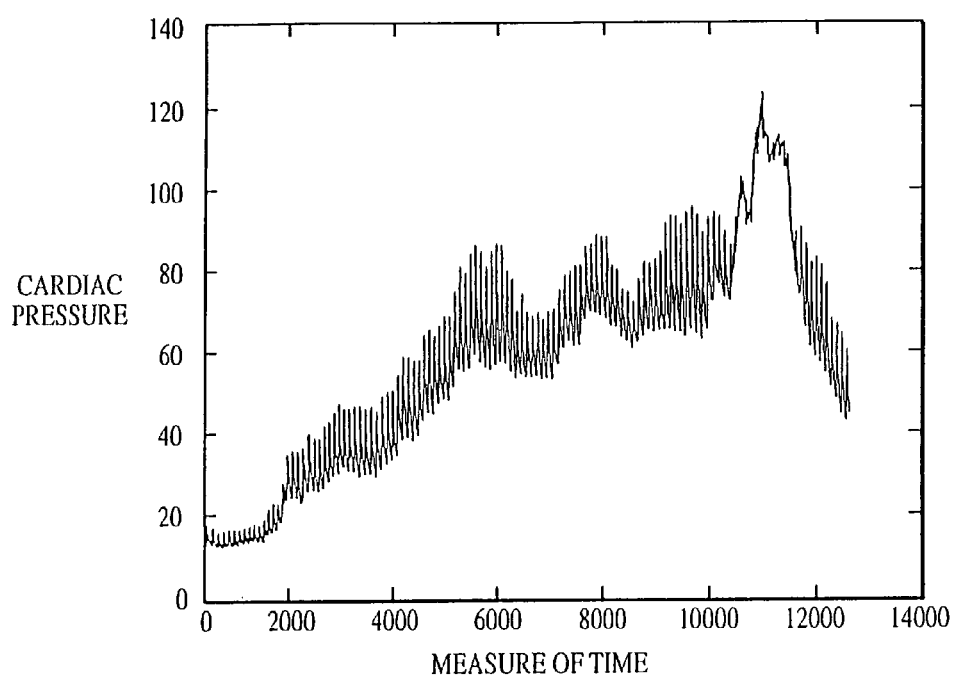
Figure 33:
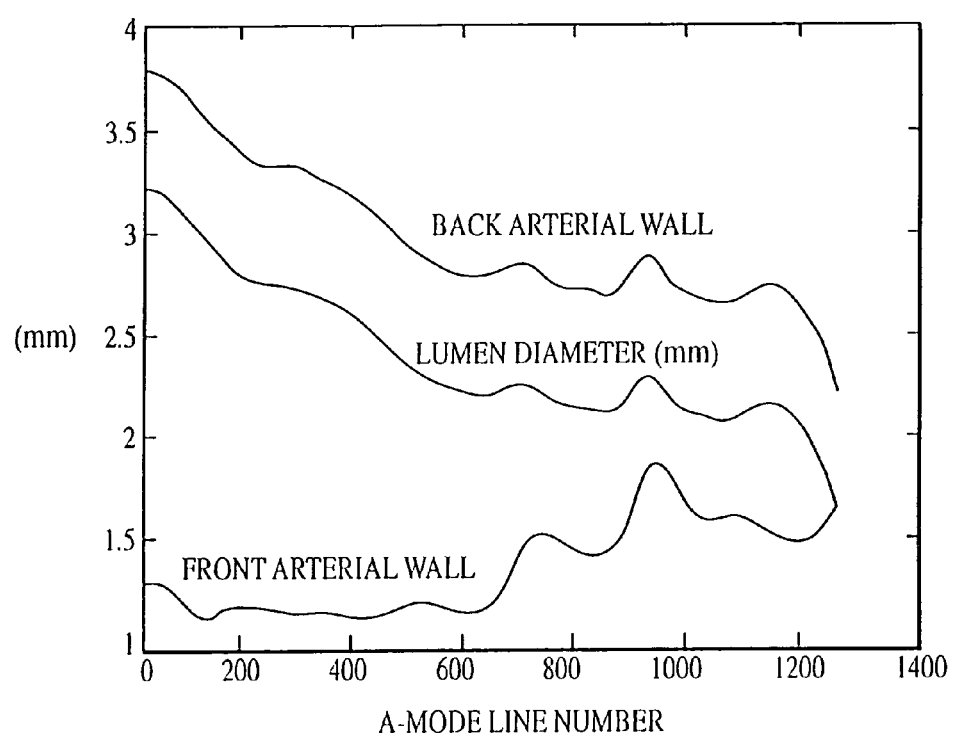
FIG. 33 is a graphical representation of the front and rear arterial wall position (depth in mm), and arterial diameter (mm), as a function of applanation.

FIG. 32, based on actual data obtained by the Assignee hereof, illustrates the foregoing problem graphically. As shown in FIG. 32, the position of the back wall 3202 of the blood vessel varies from about 4 mm in depth at zero A-mode lines (i.e., initiation of the scan), to a depth of about 3 mm after 600 A-mode lines. The variation in depth of the back wall is induced primarily by the movement of the applanation device 1204, whose linear translation (mm) varies as a function of time (FIG. 32*a*). The pressure in mm Hg registered on the pressure transducer (the actual applanating surface in contact with the tissue of the subject) is shown in FIG. 32*b*. Hence, as the applanation device and pressure transducer apply pressure to the surface of the skin atop the vessel, several effects occur: (i) the interposed tissue, including skin, musculature, and veins, compresses; (ii) the tissue behind the vessel (i.e., on the far side of the back wall) compresses; and (iii) the vessel itself compresses and overcomes its inherent hoop stress, as previously described. These three factors result in a change in the depth of the front and rear walls as shown in FIG. 32, as well as the change in diameter of the vessel. FIG. 33 graphically illustrates this change in position for the front wall 3302 and rear wall 3304 of the vessel, as well as the variation in vessel (lumen) diameter 3306 as a function of applanation. Note that the data illustrated in FIG. 33 represents smoothed data which more clearly illustrates the principles of the invention; actual or un-smoothed data is inherently more noisy.

Figure 34:
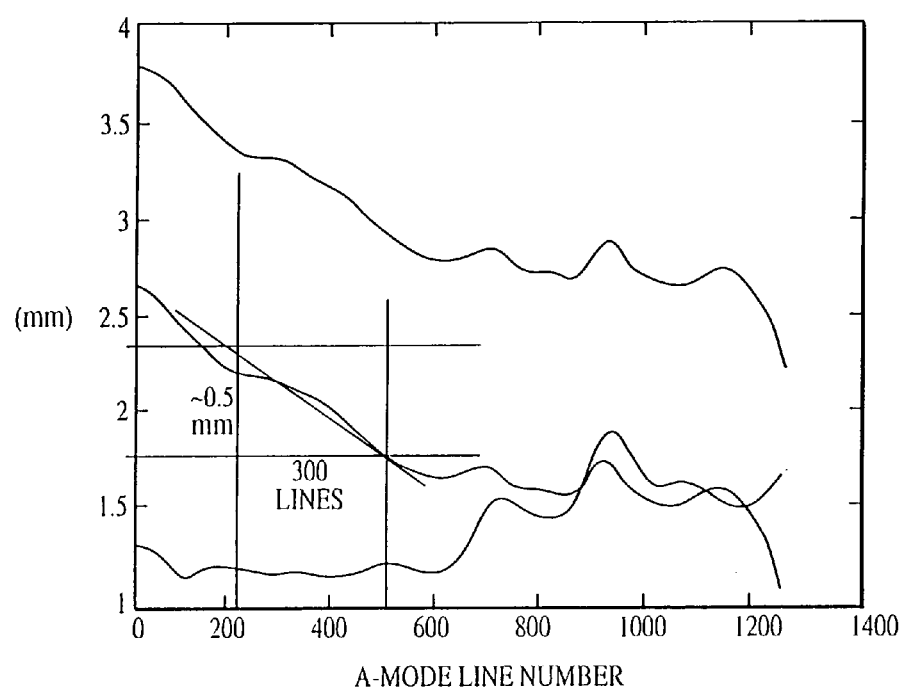
FIG. 34 is a graphical representation of the methodology of determining the rate of change of blood vessel diameter as a function of applanation according to the invention.

FIG. 34 illustrates one methodology for determining the rate of change of vessel (lumen) diameter using the front and back wall detection methods described above. The rate of change is simply calculated by taking the change in vessel diameter over a given period, and dividing by the number of A-mode lines during that same interval. This latter number may be correlated to linear change in the position of the applanation device (FIG. 33a), thereby generating a transfer function of sorts (i.e., rate of change of vessel diameter as a function of linear applanation), which describes the behavior of the tissue and blood vessel during compression.

Figure 35:
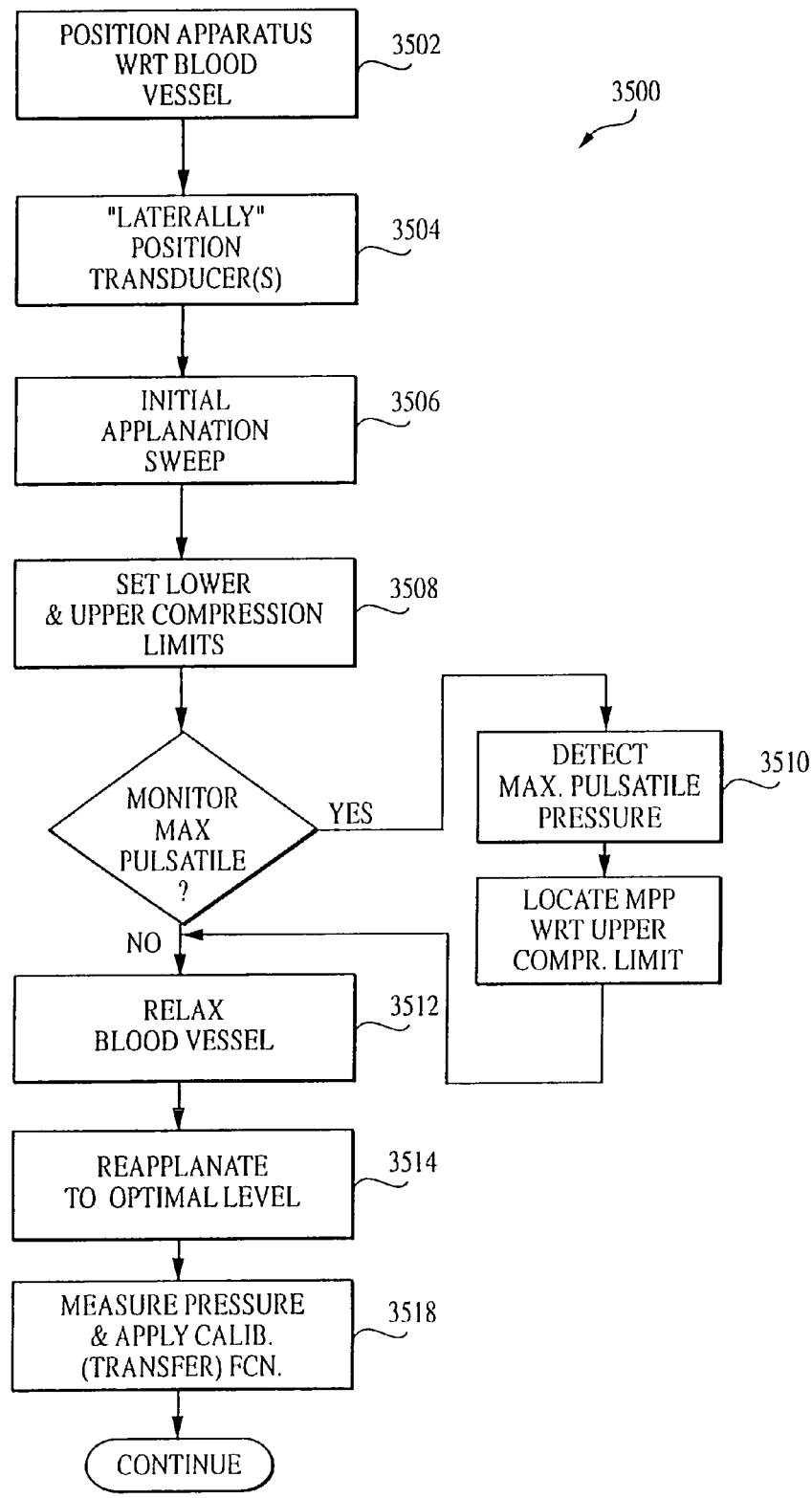
FIG. 35 is a logical flow chart illustrating one embodiment of the methodology of assessing hemodynamic parameters using lumen and wall detection according to the invention.

Method of Assessing Hemodynamic Properties Using Backscattered Ultrasonic Energy Referring now to FIG. 35, one exemplary embodiment of the method of non-invasively assessing hemodynamic properties using the aforementioned backscattered ultrasonic energy (e.g. A-mode signals) is described. It will be recognized that while the following discussion and exemplary embodiment are cast in terms of the non-invasive measurement of arterial blood pressure using the radial artery of a human being, the methods of the invention as set forth herein may be more generally applied to other hemodynamic parameters, blood vessels, and species.

As shown in FIG. 35, the method 3500 generally comprises first positioning the appropriate apparatus (such as that shown in FIG. 12 herein) generally in the region of the blood vessel to be assessed (step 3502). The site where to place the transducer(s) of the apparatus, such as the radial artery on the wrist, is generally known to the caregiver. Next, in step 3504, the apparatus is activated to laterally position the transducer(s) with respect to the blood vessel, such that optimal coupling of the apparatus to the blood vessel and interposed tissue is achieved. It will be recognized that any number of methods for lateral positioning may be used. For example, the method of lateral positioning based on observed reflection minima, described in Assignee's co-pending U.S. patent application Ser. No. 09/342,549, previously incorporated herein (including Assignee's co-pending U.S. patent application Ser. No. 09/815,982, which is a continuation-in-part of Ser. No. 09/342,549 and which is filed contemporaneously herewith and incorporated herein by reference in its entirety), may be employed either alone or in conjunction with other methods.

Note also that the act of "lateral" positioning may also include some component of longitudinal positioning (i.e., along the longitudinal axis of the blood vessel), since placement of the apparatus on the wrist/forearm of the subject is governed more by the physical attributes of the wrist, as opposed to the orientation of the blood vessel within the wrist/forearm. Specifically, in the cases where the point of measurement for the transducer(s) occurs at a location where the radial artery runs in a direction not perfectly parallel to the axis of the wrist bone, such "lateral" positioning inherently includes a longitudinal component as well. Furthermore, certain points along the blood vessel may be better suited to hemodynamic analysis (due, for example, to the existence of veins, cysts, or other components which potentially may interfere with the transmission/reflection of ultrasonic energy).

Figure 35A:
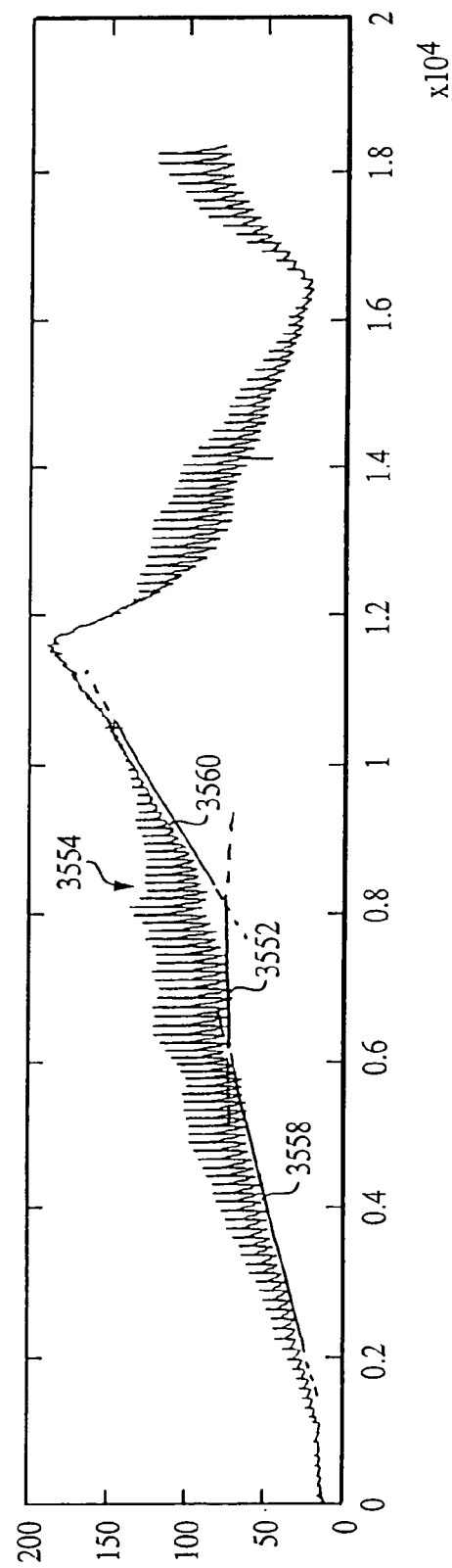
FIG. 35a is a graph of measured arterial pressure versus applanation pressure for an exemplary radial artery, indicating the "flat spot" in end-diastolic pressure.

Next, an initial calibrating applanation sweep (i.e., sweeping applied pressure from no compression through full compression or occlusion of the blood vessel) is performed in step 3506 to identify "flattening" of the slope of the end-diastolic pressure profile, therefore aiding in localizing the point(s) of interest in the pressure waveform. As shown in FIG. 35a, the flattened region 3552 of the end-diastolic waveform 3554 will generally occur between two regions 3558, 3560 of greater slope, although this may not always be readily detectable. Furthermore, it is noted that multiple flat regions may occur within a single applanation sweep.

In step 3508, the lower and upper compression limits (in the present embodiment expressed as a percentage of the diameter reduction of the blood vessel under examination) are set based on information obtained during the prior applanation sweep (step 3506). The reduction in diameter is determined by applying the techniques of front and rear blood vessel wall detection previously described with respect to FIGS. 17-34. For example, a lower limit of 25% diameter reduction and an upper limit of 50% diameter reduction (44% and 75% reduction in cross-sectional area, respectively) are used in the illustrated embodiment as lower and upper compression limits, although other values and/or indicia may be used. The lower value of 25% reduction in diameter has been experimentally determined by the Assignee hereof to equate roughly to the point where compression of the interposed and surrounding tissue has substantially occurred, and hoop stress of the blood vessel is beginning to be overcome. The upper limit of 50% reduction in diameter has been experimentally determined to correlate to the point where end-diastolic blood pressure in the blood vessel is overcome by the applied compressive force.

Additionally, it is noted that maximum pulsatile pressure will occur to the right (i.e., at later time/greater amount of blood vessel compression) of the aforementioned region of pressure waveform flattening during the applanation sweep, thereby further helping to localize the points of interest in the waveform. Specifically, other artifacts in the waveform occurring under conditions of greater compression than the maximum pulsatile pressure (the latter being readily determined by any number of means well known in the art) may be discounted, thereby narrowing the region of interest within the pressure waveform. Accordingly, maximum pulsatile pressure may optionally be monitored as well (step 3510) to further aid in setting the upper window limit on arterial compression.

After the initial applanation sweep of step 3506 is completed, and the blood vessel relaxed (3512), the vessel is again applanated to the level of compression corresponding roughly to equilibration between the applied pressure and the hoop stress of the blood vessel wall (step 3514). This level of compression is significant, in that the end diastolic pressure becomes a measure of the compressive force applied to the blood vessel, since the hoop stress component is eliminated. As previously described, this level of compression is bounded by the lower bound (e.g., 25-percent reduction in blood vessel diameter, or about a 44-percent reduction in cross-sectional area), and the upper bound (e.g., 50-percent diameter reduction, or 75-percent reduction in cross-sectional area). Hence, the optimal level of applanation, wherein the transmural pressure is equilibrated, will occur within a window of pressure formed between that associated with the lower diameter reduction bounding criterion and the upper diameter reduction bounding criterion, the window having at least a portion of the "flattened" region of the pressure profile contained therein. The pressure measured by the pressure transducer at this optimal level of applanation is used as the basis for correction via the transfer function (step 3518). One exemplary method of determining and applying the transfer function according to step 3518 is described below with respect to FIGS. 38 and 39.

It will be recognized that the pressure "window" created by the lower and upper bounding criteria may be fairly broad; accordingly, additional methods may optionally be applied to more accurately determine the optimal applanation pressure within the window. In the present embodiment, these additional methods comprise algorithmic determination of the optimal applanation level (step 3516) as described below with respect to FIG. 36.

Figure 36:
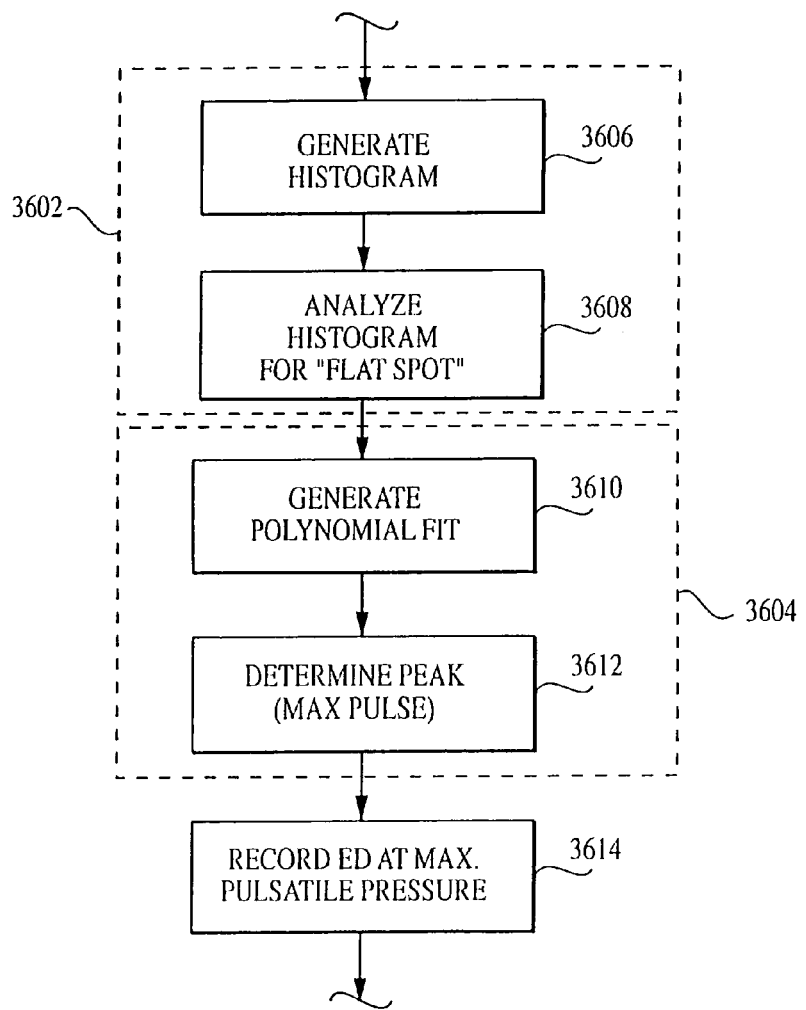
FIG. 36 is a logical flow diagram illustrating one exemplary methodology of determining optimal applanation pressure during hemodynamic measurement according to the invention.
Figure 37:
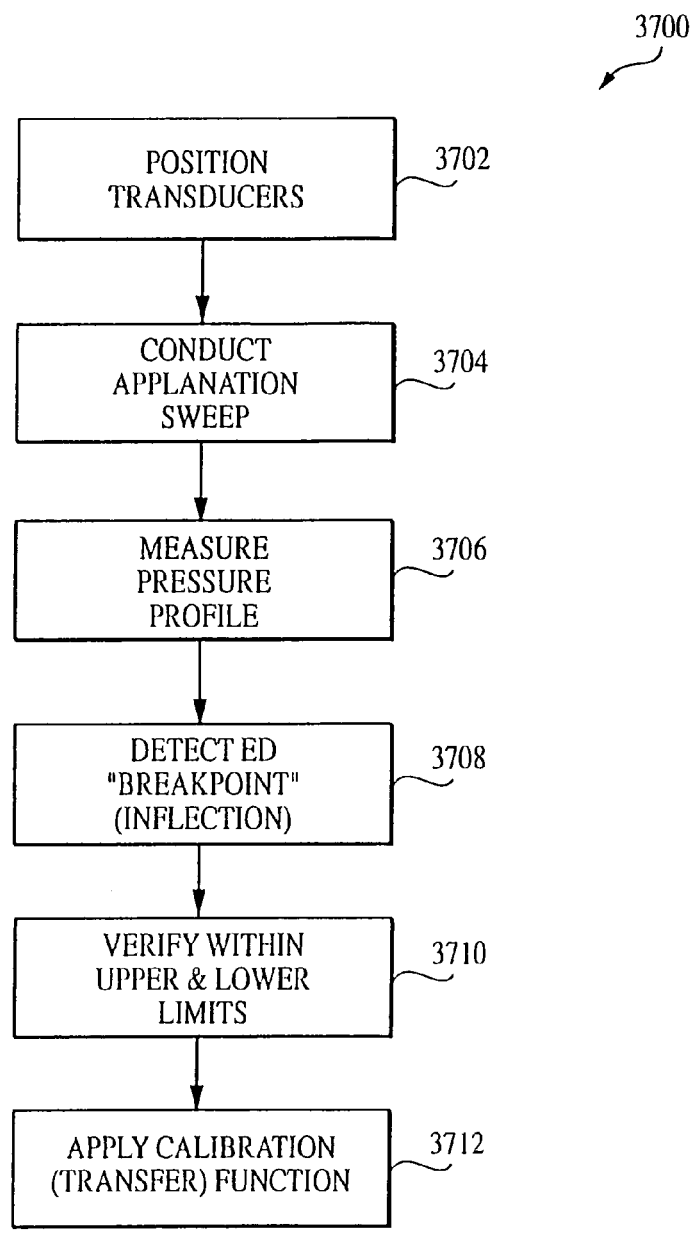
FIG. 37 is a logical flow chart illustrating an alternate embodiment of the methodology of assessing hemodynamic parameters using backscattered ultrasonic energy based on the inflection point within the diastole pressure profile.

Referring now to FIG. 36, one exemplary embodiment of the methodology of the determination of optimal applanation level (step 3516) is described. As shown in FIG. 36, the method 3600 generally comprises first identifying the "flattened" spot in the end diastolic pressure profile (step 3602). In one exemplary embodiment, a histogram derived from the end of the pressure profile over an applanation sweep is generated (step 3606). FIG. 36*a* is an exemplary histogram generated according to step 3606. Note that the largest bin values in the histogram advantageously occur at the region of the pressure profile corresponding to the flat spot in end diastolic pressure, thereby allowing for ready detection of the flat spot (step 3608).

Next, in step 3604, the end-diastolic pressure is determined at the maximum pulsatile pressure. The maximum pulse pressure is determined in the illustrated embodiment using a high order polynomial fit (step 3610) to the pulse pressure data, then determining the peak there from (step 3612). This approach helps minimize noise in the pulse pressure readings, including respiratory effects. The end diastolic pressure which occurs at the maximum pulsatile pressure is then recorded (step 3614).

Note that these two indicators of end diastolic pressure (i.e., the "flat spot" and the maximum pulsatile pressure) can be used separately or in conjunction with one another as desired. Furthermore, other techniques may be substituted for, or used in combination with, one or both of these two indicators for more precise determination of the optimal applanation pressure to be maintained during hemodynamic measurement.

In an alternate embodiment of the method of assessing hemodynamic parameters (shown in FIG. 37), the method 3700 comprises positioning the transducer(s) over the blood vessel (step 3702), and then subsequently applanating the blood vessel (step 3704) while monitoring the pressure waveform (step 3706). The point of inflection (e.g., change in slope) of the end diastolic pressure waveform is then identified per step 3708. Such inflection may be identified automatically using an algorithm adapted to identify the change in slope related to the end diastolic pressure values in the waveform, or alternatively by manual means; e.g., by visual inspection of the waveform by a trained technician. The aforementioned limiting criteria (e.g., 25% blood vessel diameter reduction nominal lower limit, and 50% diameter reduction upper limit) are applied in step 3710 to further localize the point of interest within the waveform.

Transfer Function

Figure 38:
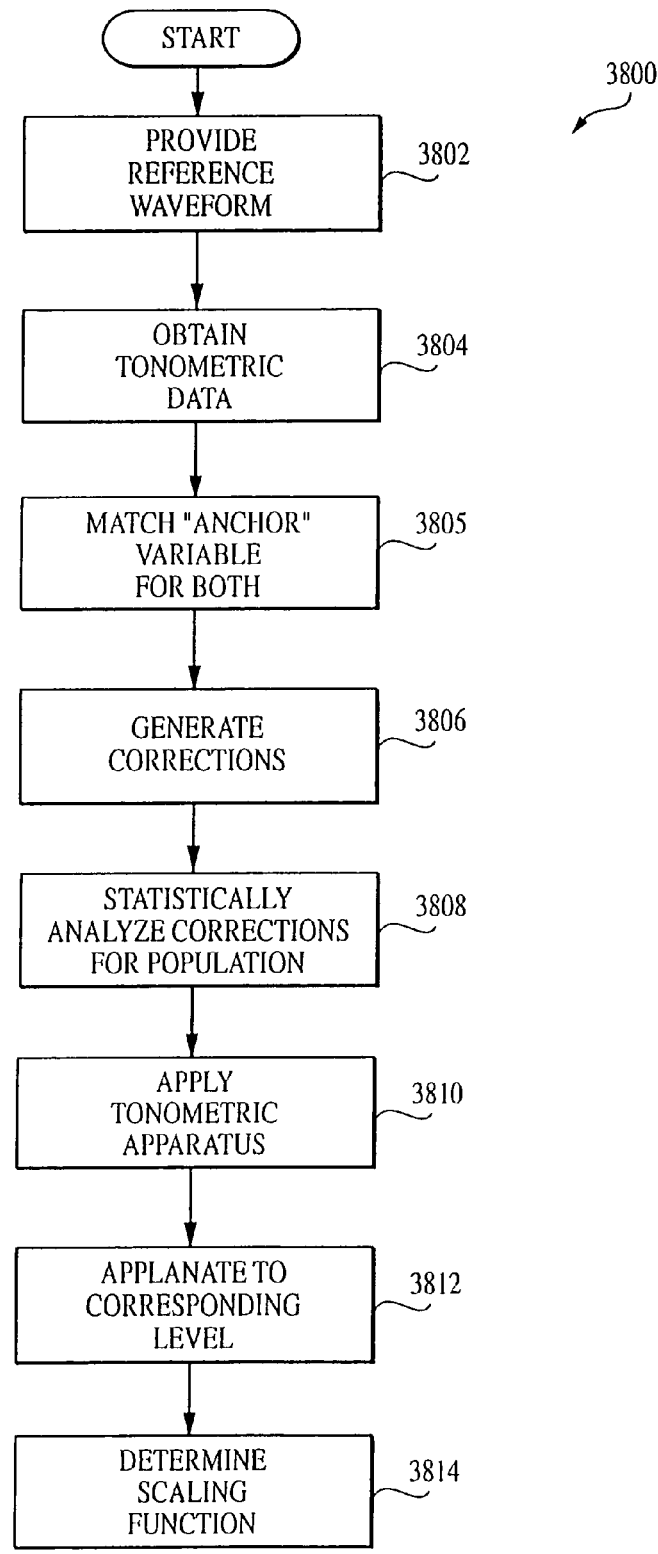
FIG. 38 is a logical flow diagram illustrating one exemplary embodiment of the method of scaling the measured pressure to account for tissue loss.
Figure 39:
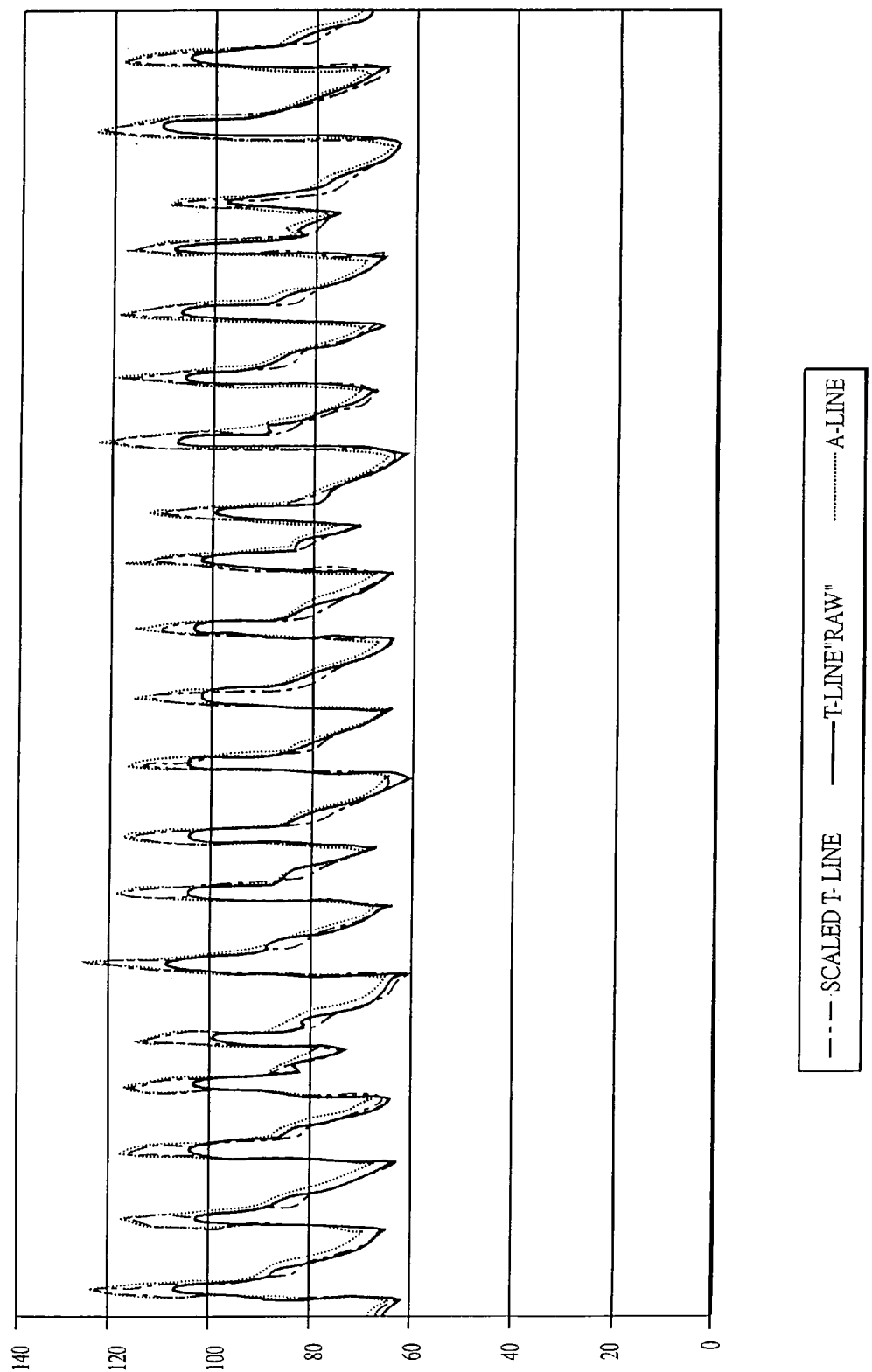
FIG. 39 is a graphical representation of the method of FIG. 38.

Referring now to FIGS. 38 and 39, one exemplary embodiment of the method of determining and applying the scaling (transfer) function to the measured value of the hemodynamic parameter (step 3518 of FIG. 35) is described.

It will be recognized that while the following discussion is cast in terms of a scaling or transfer function for use with measured arterial blood pressure values, the methodology may be more generally applied to other hemodynamic parameters or waveforms measured using the approach of FIG. 35 or otherwise. For example, if it is determined that the application of a stress to the circulatory system of a subject results in a condition of interest (e.g., pressure measured tonometrically during applanation to a certain percentage reduction in arterial diameter correlates to end-diastolic pressure), the methodology described herein may be used to determine the scaling necessary to correct the measured value for tissue compliance and other effects.

Furthermore, while the methodology of FIG. 38 generally comprises an empirically-based technique dependent on a population of data, the present invention contemplates the use of other non-empirical approaches in place of or in conjunction with the method of FIG. 38, all such variations and combinations falling within the scope of the claims appended hereto. Accordingly, the method of FIG. 38 is merely exemplary in nature.

The method 3800 of hemodynamic parametric scaling according to FIG. 38 generally comprises using empirical reference data in order to derive corrections which are subsequently applied to in situ measurements of blood pressure obtained from the subject under examination. Stress is applied to the blood vessel being measured so as to match or "anchor" one variable of interest (e.g., end-diastolic pressure) between the empirical reference data and the in situ measurement. The derived corrections for other non-anchored variables (e.g., systolic and mean blood pressure) are then applied to the corresponding portions of the in situ waveform of the subject under evaluation in order to obtain a corrected waveform which is effectively equivalent to the actual intra-arterial pressure.

As shown in FIG. 38, the method 3800 comprises first providing a determining a reference value or waveform of the desired parameter (e.g., arterial blood pressure) apart from the methods previously described herein (step 3802). In one embodiment, reference blood pressure data is obtained from a plurality of living subjects via an "A-line" invasive catheter device of the type well known in the medical arts. The A-line device is generally accepted as an accurate means of determining true arterial blood pressure (waveforms), but disadvantageously requires insertion of its catheter probe into the circulatory system of the subject. Tonometric pressure data for the same patient is simultaneously obtained (step 3804); this tonometric measurement comprises applanating the blood vessel of the subject such that the tonometrically measured value of the "anchor" variable (here end-diastolic pressure) is as closely matched as possible to the actual end-diastolic pressure as determined by the A-line.

In one simple embodiment, the applanation level is progressively increased until the anchor variable of the waveform measured by the tonometric pressure transducer (and graphically displayed on a display device such as a cathode ray tube (CRT) or similar) matches, as closely as practical, the value of the same variable of the A-line. Matching is accomplished by the operator primarily by visual means, such as contemporaneous overlapping display of the waveforms, or minimization of the difference in two numerical values displayed on the display device. The operator then adjusts applanation level for the best level of matching possible.

In another embodiment, the applanation is controlled by an algorithm which automatically computes, on a periodic or continuous basis, the anchor variable of interest from both the A-line and tonometric waveforms, and attempts to match them as closely as possible using scoring metrics. For example, a scoring metric which is related to the difference in end-diastolic pressure during discrete time intervals may be used to evaluate the quality of "fit" between the waveforms, the metric being used as an input to the applanation motor control circuitry previously described so as to modulate pressure to minimize the value of the metric during the selected time interval(s). Such curve-fitting metrics are well known to those of ordinary skill in the signal processing arts, and accordingly are not described further herein.

After matching of the anchor variable and collection of data, the two sets of data are analyzed to provide a characterization of the relationship between the true arterial pressure (i.e., the A-line value) and the tonometrically obtained pressure for that individual per step 3806. Differences between the reference values and those derived from a tonometric device result from transfer loss due to, inter alia, compression of interposed tissue during tonometric measurement. Specifically, in the illustrated embodiment, corrections for systolic and mean arterial blood pressure are calculated based the fact that the end-diastolic pressures within the two waveforms were matched. These corrections or differences are then statistically analyzed in light of similar data from all other subjects for which empirical data has been collected to determine "mean" systolic and "mean" mean correction factors (step 3808). It has been empirically determined by the Assignee hereof, based on a sampling of the radial arteries of several hundred patients, that the mean error between A-line and tonometric measurement over all patients studied for systolic pressure was −13.6%, and the mean error for the mean pressure was −5.6%. In essence, these figures indicate that the reference device (i.e. A-line) was nominally higher by about 14% for systolic readings and about 6% higher for mean readings, when the tonometric transducer was applanated such that the end-diastolic value was matched to the reference value as previously described.

After the correction factors for the parameters of interest have been obtained per step 3808, the non-invasive hemodynamic assessment apparatus of the present invention is applied to the blood vessel of interest of the subject under evaluation; e.g., on the radial artery, per step 3810. Stress is next applied to the blood vessel in step 3812. Specifically, the stress is applied in order to induce changes in the hemodynamic properties within the blood vessel to a point generally where the "anchor" variable of interest (end-diastolic pressure in the present embodiment) most achieves a desired value bearing some known relationship to the actual value of the anchor variable. In the present context, this application of stress comprises applanating the blood vessel using the non-invasive (tonometric) applanation device previously described herein while non-invasively measuring the pressure waveform of the blood vessel, the degree of applanation being determined by the relationship of the anchor variable within the measured pressure waveform to the actual value.

Next, in step 3814, a scaling or transfer function is determined from the foregoing data for the subject being evaluated. In one embodiment, the transfer function is obtained by solving the following three simultaneous equations for a curve fit polynomial, based on the input values of uncorrected pressure and "corrected" pressure:

$$P_{sc}=k_1P_{su}^2+k_2P_{su}+k_3 \quad \text{(Eqn. 16)}$$

$$P_{mc}=k_1P_{mu}^2+k_2P_{mu}+k_3 \quad \text{(Eqn. 17)}$$

$$P_{dc}=k_1P_{du}^2+k_2P_{du}+k_3 \quad \text{(Eqn. 18)}$$

Where:
$P_{sc}$, $P_{dc}$, $P_{sc}$=systolic, diastolic and mean "corrected" (scaled) pressures respectively; and
$P_{su}$, $P_{du}$, $P_{mu}$=systolic, diastolic and mean uncorrected (original) pressures respectively.

By solving for constants $k_1$, $k_2$ and $k_3$, a polynomial curve is generated which can advantageously scale the tonometrically obtained waveform for the present subject for all values of pressure, and therefore provide a scaled output given that the input waveform is matched (by the methods previously described herein, or other techniques) to the end-diastolic value, or to any end-diastolic point with known relationship to the actual value.

FIG. 39 is a graphical representation of the foregoing process.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. An apparatus for locating a blood vessel having a lumen, said apparatus comprising:
    a transducer element adapted to transmit acoustic energy into said blood vessel; and
    a processor element adapted to:
        determine a power of backscatter energy from said transmitted energy as a function of depth within said blood vessel;
        identify at least one artifact associated with a location of said lumen;
        compute a power function in a first dimension relative to said location; and
        compute a power function in a second dimension relative to said location;
    wherein said computations substantially determine a location of said blood vessel.

2. The apparatus of claim 1, wherein said identification is performed via a method that identifies at least one plateau.

3. The apparatus of claim 1, wherein said identification is performed via a method that specifies at least one interval.

4. A method of locating a blood vessel having a lumen, comprising:
    transmitting acoustic energy into said blood vessel via a transducer;
    receiving a signal related to backscattered energy derived from said transmitted acoustic energy at said transducer; and
    processing said backscattered energy to identify at least one artifact associated with said lumen at a processor associated with said transducer, said at least one artifact comprising a substantially flat portion of a power profile corresponding to said lumen.

5. The method of claim 4, wherein said identification of said substantially flat portion comprises:
- determining a power metric as a function of depth;
- integrating said power metric and normalizing said integrated power metric; and
- detecting a plateau associated with said lumen based at least in part on said acts of determining and integrating.

6. Apparatus adapted to detect the location of a blood vessel, comprising:
- an acoustic transducer;
- a signal transceiver operatively coupled to said acoustic transducer; and
- a processor operatively coupled to said signal transceiver, said processor adapted to perform computations on data received by said signal transceiver in order to compute the location of said blood vessel;
- wherein said processor is further adapted to;
  - baseband said received acoustic energy data; and
  - square said basebanded data to produce envelope-squared data.

7. The apparatus of claim 6, wherein said acoustic transducer comprises an ultrasonic transducer.

8. The apparatus of claim 6, wherein said processor basebands said received acoustic energy data by:
- multiplication of the received acoustic energy data by a sine and cosine function; and
- application of a lowpass filter to said multiplied data to produce said basebanded data.

9. The apparatus of claim 6, wherein said processor is further adapted to decimate said envelope-squared data to a predetermined sampling rate, and apply a depth-dependent gain to said decimated envelope-squared data.

10. The apparatus of claim 9, wherein said depth-dependent gain is non-linear.

11. An apparatus for locating a position of a blood vessel having a lumen, said apparatus comprising:
- a means for transmitting acoustic energy into said blood vessel;
- a means for determining power of backscatter energy from said transmitted energy as a function of depth within said blood vessel;
- a means for identifying at least one artifact associated with a location of said lumen; and
- a means for calculating:
  - a power function in a first dimension relative to said location; and
  - a power function in a second dimension relative to said location;
- wherein said means for calculating are utilized to substantially determine a location of said blood vessel.

12. The apparatus of claim 11, wherein said means for identifying at least one artifact comprise means for identifying at least one plateau.

13. The apparatus of claim 11, wherein said means for identifying at least one artifact comprise means for identifying at least one interval.

14. A method of locating a blood vessel having a lumen, comprising:
- transmitting acoustic energy into said blood vessel via a transducer;
- receiving, at said transducer, backscattered energy produced from said transmitted acoustic energy; and
- processing, at a processor in signal communication with said transducer, said received backscattered energy to identify at least one artifact associated with said lumen;
- wherein said identification of said at least one artifact comprises identification of a substantially flat portion of a power profile corresponding to said lumen.

15. The method of claim 14, wherein said identification of said substantially flat portion comprises:
- determining a power metric as a function of depth;
- integrating said power metric and normalizing said integrated power metric; and
- detecting a plateau associated with said lumen based at least in part on results from said acts of determining and integrating.

16. The method of claim 15, wherein:
- said identification of said substantially flat portion further comprises dividing said normalized integrated power metric into a number of intervals; and
- said detecting said plateau is based at least in part on said acts of determining, integrating and dividing.

17. The method of claim 16, wherein said dividing is performed in substantially equally spaced intervals.

18. The method of claim 16, wherein said dividing is performed in substantially non-equally spaced intervals.

19. The method of claim 14, wherein said processing is performed using an interval-based method.

* * * * *